(12) United States Patent
Ebright et al.

(10) Patent No.: US 8,461,314 B2
(45) Date of Patent: Jun. 11, 2013

(54) NUCLEIC ACID SEQUENCES FOR BIOSYNTHESIS OF NON-MCCJ25-RELATED LARIAT PEPTIDES

(75) Inventors: Richard H. Ebright, North Brunswick, NJ (US); Konstantin Severinov, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 486 days.

(21) Appl. No.: 12/594,152

(22) PCT Filed: Sep. 20, 2007

(86) PCT No.: PCT/US2007/079032
§ 371 (c)(1),
(2), (4) Date: Jun. 21, 2010

(87) PCT Pub. No.: WO2008/121154
PCT Pub. Date: Oct. 9, 2008

(65) Prior Publication Data
US 2010/0261171 A1    Oct. 14, 2010

Related U.S. Application Data

(60) Provisional application No. 60/921,136, filed on Mar. 31, 2007.

(51) Int. Cl.
*A61K 38/12* (2006.01)
*C07H 21/02* (2006.01)
*A61K 38/00* (2006.01)

(52) U.S. Cl.
USPC ........ 536/23.1; 514/21.1; 514/21.3; 514/19.9

(58) Field of Classification Search
None
See application file for complete search history.

(56) References Cited

U.S. PATENT DOCUMENTS

| | | | | |
|---|---|---|---|---|
| 5,824,795 A * | 10/1998 | Popoff et al. | ................. | 536/24.3 |
| 2001/0049830 A1 * | 12/2001 | Goodman et al. | ............ | 800/278 |
| 2011/0201040 A1 * | 8/2011 | Ebright et al. | .................. | 435/29 |

* cited by examiner

Primary Examiner — Manjunath Rao
Assistant Examiner — Samuel Liu
(74) Attorney, Agent, or Firm — Davidson, Davidson & Kappel, LLC

(57) ABSTRACT

A nucleic acid sequence is provided, encoding at least one of a precursor of a lariat peptide, a processing factor of a lariat peptide, and an export factor of a lariat peptide, wherein the lariat peptide is a non-MccJ25 lariat peptide according to general structural formula (I) Also provided are biosynthesis systems useful for the synthesis of peptides according to formula (I), and methods of detecting and identifying nucleic acid sequences encoding the disclosed proteins.

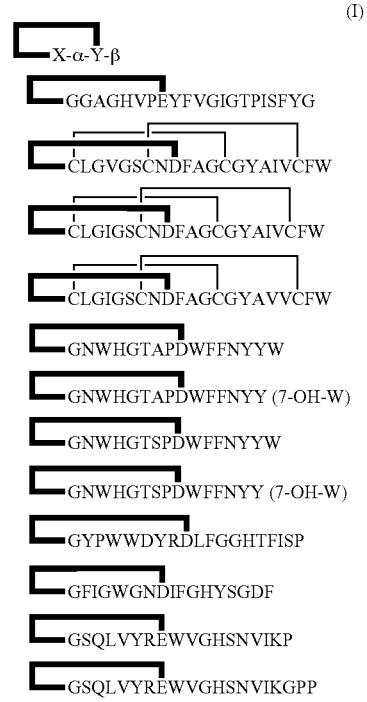

24 Claims, 2 Drawing Sheets

FIG. 1

Prior Art

| | |
|---|---|
| microcin J25 (MccJ25) | GGAGHVPEYFVGIGTPISFYG |
| siamycin I | CLGVGSCNDFAGCGYAIVCFW |
| siamycin II | CLGIGSCNDFAGCGYAIVCFW |
| siamycin III | CLGIGSCNDFAGCGYAVVCFW |
| RES-701-1 | GNWHGTAPDWFFNYYW |
| RES-701-2 | GNWHGTAPDWFFNYY(7-OH-W) |
| RES-701-3 | GNWHGTSPDWFFNYYW |
| RES-701-4 | GNWHGTSPDWFFNYY(7-OH-W) |
| propeptin | GYPWWDYRDLFGGHTFISP |
| anantin | GFIGWGNDIFGHYSGDF |
| lariatin A | GSQLVYREWVGHSNVIKP |
| lariatin B | GSQLVYREWVGHSNVIKGPP |

NUCLEIC ACID SEQUENCES FOR BIOSYNTHESIS OF NON-MCCJ25-RELATED LARIAT PEPTIDES

CROSS-REFERENCE TO RELATED APPLICATIONS

This application is a National Phase Application of PCT/US2007/079032 filed on Sep. 20, 2007, which claims the benefit of U.S. Provisional Application No. 60/921,136, filed Mar. 31, 2007, the entire contents of which are incorporated herein by reference.

GOVERNMENT SUPPORT

This invention was supported by U.S. Government funds (NIH-R01-GM41376 and NIH R01-GM6453). Therefore, the Government may have rights to this invention.

BACKGROUND ART

Lariat-Peptide MccJ25

The antibacterial peptide microcin J25 (MccJ25) inhibits bacterial RNA polymerase by binding within, and obstructing, the secondary channel of bacterial RNA polymerase (WO 2004/023093; Mukhopadhyay et al. (2004) *Mol. Cell* 14, 739-751; Adelman, et al. (2004) *Mol. Cell* 14, 753-762). MccJ25 has the sequence $Gly_1$-$Gly_2$-$Ala_3$-$Gly_4$-$His_5$-$Pro_6$-$Val_7$-$Glu_8$-$Tyr_9$-$Phe_{10}$-$Val_{11}$-$Gly_{12}$-$Ile_{13}$-$Gly_{14}$-$Thr_{15}$-$Pro_{16}$-$Ile_{17}$-$Ser_{18}$-$Phe_{19}$-$Tyr_{20}$-$Gly_{21}$ cyclic(8→1) peptide (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483; FIG. 1, line 1).

MccJ25 has an unusual "lariat-peptide" covalent structure (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483; FIG. 1, line 1). MccJ25 is 21 amino acids in length and consists of an 8-residue cyclic segment—with a backbone-sidechain amide linkage between the backbone nitrogen atom of residue $Gly_1$ and the side-chain carboxyl group of $Glu_8$—followed by a 13-residue linear segment.

MccJ25 further has an unusual "lariat-protoknot" three-dimensional structure (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483; FIG. 2). In the three-dimensional structure of MccJ25, the linear segment of the lariat loops back and penetrates and threads through the cycle of the lariat, essentially as a thread through the eye of a needle. The linear segment is irreversibly locked in place and trapped within the cycle by steric constraints imposed by the aromatic sidechains of $Phe_{19}$ and $Tyr_{20}$, which bracket the cycle, with the aromatic sidechain of $Phe_{19}$ being on located on one face of the cycle and the aromatic sidechain of $Tyr_{20}$ being located on the other face of the cycle.

The lariat-peptide/lariat-protoknot structure of MccJ25, with irreversible trapping of the linear segment of the lariat within the cycle of the lariat, results in exceptional resistance to denaturation (complete resistance to tested thermal and chemical denaturants; Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483) and exceptional resistance to proteolysis (complete resistance to tested mesophilic endo- and exopeptidase; Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483).

The lariat-peptide/lariat-protoknot structure of MccJ25 is generated by a MccJ25-specific biosynthetic system. MccJ25 is produced by bacterial strains harboring a plasmid-borne lariat-peptide/lariat-protoknot biosynthetic cassette, consisting of a gene for MccJ25 precursor, two genes for factors that process McJ25 precursor into mature MccJ25, and one gene for a factor that exports MccJ25 from the cell (Solbiati, et al. (1999) *J. Bacteriol.* 181, 2659-2662). The gene names and functions are as follows:

mcjA; encodes the MccJ25 precursor (McjA)
mcjB; encodes a MccJ25 processing factor (McjB)
mcjC; encodes a MccJ25 processing factor (McjC)
mcjD; encodes a MccJ25 export factor (McjD)

The MccJ25 precursor is a 58-residue peptide consisting of a 37-residue N-terminal pro-sequence (residues numbered as −37 to −1) and a 21-residue C-terminal segment having the same amino acid sequence as mature MccJ25 (residues numbered as 1 to 21) (Solbiati, et al. (1999) *J. Bacteriol* 181, 2659-2662).

Processing of the MccJ25 precursor to yield mature MccJ25 entails two reactions: (1) cleavage of the backbone-backbone amide linkage between residue −1 and residue 1, resulting in removal of the 37-residue N-terminal pro-sequence; and (2) formation of a backbone-sidechain amide linkage between the backbone nitrogen atom of residue 1 and the sidechain carboxyl of residue 8, resulting in cyclization of residues 1-8 and entrapment of residues 9-21 (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483). The MccJ25 processing factor McjC exhibits amino acid sequence similarity to amidotransferases of the Asn-synthase/Gln-hydrolase class, which catalyze transfer of ammonia or an amine from an amide donor to a carboxyl acceptor (Bayro, et al. (2003) *J. Am. Chem. Soc.* 125, 12382-12383). It has been proposed that McjC participates in both reactions in processing of the MccJ25 precursor to yield mature MccJ25, acting on pre-folded MccJ25 precursor to catalyze transfer of the backbone nitrogen atom, also known as the α-amino group, of residue 1 from the backbone amide linkage between residue −1 and residue 1 to the sidechain carboxyl of residue 8 (Bayro, et al. (2003) *J. Am. Chem. Soc.* 125, 12382-12383).

It has not been possible to date to re-create the lariat-peptide/lariat-protoknot structure of MccJ25 without use of the above-described MccJ25-specific biosynthetic system. Attempted chemical synthesis of MccJ25 yields a product having a lariat-peptide covalent structure but not having a lariat-protoknot three-dimensional structure (i.e., not having the linear segment of the lariat looped back and penetrating and threading through the cyclic segment of the lariat; the resulting material exhibits no detectable biological activity (Rosengren, et al. (2003) *J. Am. Chem. Soc.* 125, 12464-12474; Wilson, et al. (2003) *J. Am. Chem. Soc.* 125, 12475-12483). Chemical synthesis of a linear analog of MccJ25 yields a product having neither a lariat-peptide covalent structure nor a lariat-protoknot structure; the resulting material exhibits no detectable biological activity (Rosengren, et al. (2003) *J. Am. Chem. Soc.* 125, 12464-12474; Wilson, et al. (2003) *J. Am. Chem. Soc.* 125, 12475-12483). Production of a recombinant linear analog of MccJ25, by use of a nucleic acid sequence encoding the linear analog of MccJ25 likewise yields a product having neither a lariat-peptide covalent structure nor a lariat-protoknot structure and exhibiting no detectable biological activity.

The MccJ25 lariat-peptide/lariat-protoknot biosynthetic cassette is organized as a gene cluster, with gene order mcjA, mcjB, mcjC, mcjD (Solbiati, et al. (1996) *J. Bacteriol.* 178, 3661-3663; Solbiati, et al. (1999) *J. Bacteriol.* 181, 2659-2662). The size of the MccJ25 lariat-peptide/lariat-protoknot biosynthetic cassette is ~4,500 bp.

The MccJ25 lariat-peptide/lariat-protoknot biosynthetic cassette can be expressed in an original, naturally occurring, Mcc25-producer strain, resulting in MccJ25 production (Solbiati, et al. (1996) *J. Bacteriol.* 178, 3661-3663; Solbiati, et al. (1999) *J. Bacteriol.* 181, 2659-2662).

The MccJ25 lariat-peptide/lariat-protoknot biosynthetic cassette also can be introduced into, and expressed in, a surrogate host strain, resulting in surrogate-host MccJ25 production (Solbiati, et al. (1999) *J. Bacteriol.* 181, 2659-2662; Blond, et al. (1999) *Eur. J. Biochem.* 259, 747-755).

Because the nucleotide sequence of the mcjA gene determines the amino acid sequence of the MccJ25 precursor, and because, in MccJ25 biosynthesis, the MccJ25 precursor is processed to yield mature MccJ25, a change in the nucleotide sequence of the mcjA gene ("mutation") can result in a corresponding change in the amino acid sequence of MccJ25 ("substitution"). The relationship between a mutation in the mcjA gene and a corresponding substitution in MccJ25 is determined by, and is predictable from, the universal genetic code.

Introduction of a mutation into the mcjA gene can be accomplished in straightforward fashion by use of molecular-biology and directed-evolution procedures known in the art, including, for example, random mutagenesis, site-directed mutagenesis, and gene synthesis (WO 2004/023093; U.S. application Ser. No. 11/371,736, filed Mar. 9, 2006; Mukhopadhyay, et al. (2004) *Mol. Cell* 14, 739-751; see also Sambrook, J., et al. (1989) *Molecular Cloning: A Laboratory Manual*, Cold Spring Harbor Laboratory, Cold Spring Harbor, N.Y.).

Accordingly, mcjA derivatives containing mutations, and corresponding MccJ25 derivatives containing substitutions, can be, and have been, prepared (See WO 2004/023093 and U.S. application Ser. No. 11/371,736, filed Mar. 9, 2006, the entire contents of each of which are incorporated by reference; and Mukhopadhyay, et al. (2004) *Mol. Cell* 14, 739-751). This approach is limited to production of MccJ25 derivatives containing substitutions at a subset of residue positions, since other residue positions cannot be substituted without disruption of processing or export (U.S. application Ser. No. 11/371,736, filed Mar. 9, 2006). Nevertheless, this approach provides a source of MccJ25 derivatives having different useful properties, including, for example, high affinity for a target of interest, high potency for inhibition of a reaction of interest, or suitability for site-specific incorporation of a detectable group such as a fluorochrome (WO 2004/023093; U.S. application Ser. No. 11/371,736, filed Mar. 9, 2006; Mukhopadhyay, et al. (2004) *Mol. Cell* 14, 739-751).

In the same manner, "libraries" of mcjA derivatives containing single mutations or small numbers of mutations, and corresponding "libraries" of MccJ25 derivatives containing single substitutions or small numbers of substitutions, can be, and have been, prepared (U.S. application Ser. No. 11/371,736, filed Mar. 9, 2006). This approach is limited to production of libraries of MccJ25 derivatives containing substitutions at a subset of residue positions, since other residue positions cannot be substituted without disruption of processing or export (U.S. application Ser. No. 11/371,736, filed Mar. 9, 2006). Nevertheless, this approach, optionally combined with screening of "libraries" by use of procedures known in the art, provides a further source of MccJ25 derivatives with different useful properties, including, for example, high potency for inhibition of a reaction of interest, or suitability for site-specific incorporation of a detectable group such as a fluorochrome (U.S. application Ser. No. 11/371,736, filed Mar. 9, 2006).

MccJ25 inhibits Gram-negative bacterial RNA polymerase by binding within, and obstructing, the secondary channel of Gram-negative bacterial RNA polymerase (WO 2004/023093; Mukhopadhyay et al. (2004) *Mol. Cell* 14, 739-751; Adelman, et al. (2004) *Mol. Cell* 14, 753-762). Through inhibition of Gram-negative bacterial RNA polymerase, MccJ25 exhibits antibacterial activity against certain Gram-negative bacterial species, including the Gram-negative enterics *Escherchia coli* and *Salmonella* sp. (Delgado, et al. (2001) 183, 4543-4550; Yuzenkova, et al. (2002) 277, 50867-50875). MccJ25 does not inhibit Gram-positive bacterial RNA polymerase or *Thermococcus-Deinococcus* bacterial RNA polymerase, and, accordingly, MccJ25 not inhibit Gram-positive bacterial RNA polymerase or *Thermococcus-Deinococcus* bacterial growth (Yuzenkova, et al. (2002) 277, 50867-50875).

The binding site for MccJ25 within bacterial RNA polymerase is remote from the binding site for rifamycins and from the sites of substitutions that confer resistance to rifamycins (WO 2004/023093; Mukhopadhyay et al. (2004) *Mol. Cell* 14, 739-751; Adelman, et al. (2004) *Mol. Cell* 14, 753-762). Accordingly, MccJ25 exhibits no cross-resistance with rifamycins and retains full ability to inhibit RNA polymerase derivatives resistant to rifamycins.

MccJ25, as a direct consequence of its lariat-peptide/lariat-protoknot structure, exhibits two features useful for drug design and drug discovery:

(1) MccJ25 is genetically encoded (albeit indirectly, through genetic encoding of a precursor and processing and export factors; Solbiati, et al. (1996) *J. Bacteriol.* 178, 3661-3663; Solbiati, et al. (1999) *J. Bacteriol.* 181, 2659-2662), permitting efficient production by fermentation (Blond, et al. (1999) *Eur. J. Biochem.* 259, 747-755) and permitting efficient construction of derivatives by molecular-biology or directed-evolution procedures (WO 2004/023093; U.S. application Ser. No. 11/371,736, filed Mar. 9, 2006; Mukhopadhyay, et al. (2004) *Mol. Cell* 14, 739-751).

(2) MccJ25 is resistant to denaturation and proteolysis (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483).

This combination of features is not only useful, but also unusual. Most compounds do not exhibit this combination of features. (Most peptides and proteins exhibit only the first feature. Most non-peptide, non-protein compounds exhibit only the second feature.)

Non-MccJ25-Related Lariat Peptides

We refer herein to compounds according to general structural formula (I) as "non-MccJ25-related lariat peptides."

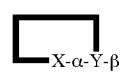

(I)

wherein:
(i) X is an amino acid residue containing a backbone nitrogen atom;
(ii) Y is an amino acid residue containing a side-chain carboxyl group;

(iii) α is a peptide segment of from about 5 to about 8 amino acid residues;

(iv) β is a peptide segment of from about 6 to about 15 amino acid residues;

(v) there is an amide bond between the backbone nitrogen atom of X and the side-chain carboxyl of Y; and (vi) wherein the compound has less than 25% amino acid sequence identity with microcin J25 (MccJ25).

Non-MccJ25-related lariat peptides are known in the art and include the siamycins [siamycin I (also known as MS-271, NP-06, and FR901724; Yano, et al. (1996) *Bioorg. Med. Chem* 4, 115-120; Katahira, et al. (1996) *Bioorg. Med. Chem* 4, 121-129; Chokekijchai, et al. (1995) *Antimicrob. Agents Chemother.* 39, 2345-2347; Nakashima, et al. (1996) *Biol. Pharm. Bull.* 19, 405-412; Detlefsen, et al. (1995) *J. Antibiot.* 48, 1515-1517), siamycin II (Detlefsen, et al. (1995) *J. Antibiot.* 48, 1515-1517; Constantine, et al. (1995) *J. Biomol. NMR* 5, 271-286), and siamycin III (also known as RP 71955 and aborycin; Helynck, et al. (1993) *J. Antibiot.* 46, 1756-1757; Frechet, et al. (1994) *Biochem.* 33, 42-50; Potterat, et al. (1994) *Liebigs Annalen der Chemie* 7, 741-743)], RES-701-n [RES-701-1 (Yamasaki, et al. (1994) *J. Antibiot.* 47, 276-280; Katahira, et al. (1995) *Bioorg. Med. Chem.* 3, 1273-1280), RES-701-2 (Yano, K. et al. (1995) *J. Antibiot.* 48, 1368-1370; Ogawa, et al. (1995) *J. Antibiot.* 48, 1213-1220), RES-701-3 (Ogawa, et al. (1995) *J. Antibiot.* 48, 1213-1220), and RES-701-4 (Ogawa, et al. (1995) *J. Antibiot.* 48, 1213-1220)], propeptin (Kimura, et al. (1997) *J. Antibiot.* 50, 373-378), anantin (Wyss, et al. (1991) *J. Antibiot.* 44, 172-180), and lariatins [lariatin A and lariatin B (Iwatsuki, et al. (2006) *J. Am. Chem. Soc.* 128, 7486-7491)] (FIG. 1).

Known non-MccJ25-related lariat peptides have lariat-peptide covalent structures similar to the lariat-peptide covalent structure of MccJ25 (Yano, et al. (1996) *Bioorg. Med. Chem* 4, 115-120; Katahira, et al. (1996) *Bioorg. Med. Chem* 4, 121-129; Chokekijchai, et al. (1995) *Antimicrob. Agents Chemother.* 39, 2345-2347; Nakashima, et al. (1996) *Biol. Pharm. Bull.* 19, 405-412; Detlefsen, et al. (1995) *J. Antibiot.* 48, 1515-1517; Constantine, et al. (1995) *J. Biomol. NMR* 5, 271-286; Helynck, et al. (1993) *J. Antibiot.* 46, 1756-1757; Frechet, et al. (1994) *Biochem.* 33, 42-50; Potterat, et al. (1994) *Liebigs Annalen der Chemie* 7, 741-743; Yamasaki, et al. (1994) *J. Antibiot.* 47, 276-280; Katahira, et al. (1995) *Bioorg. Med. Chem.* 3, 1273-1280; Yano, K. et al. (1995) *J. Antibiot.* 48, 1368-1370; Ogawa, et al. (1995) *J. Antibiot.* 48, 1213-1220; Kimura, et al. (1997) *J. Antibiot.* 50, 373-378; Wyss, et al. (1991) *J. Antibiot.* 44, 172-1801; Iwatsuki, et al. (2006) *J. Am. Chem. Soc.* 128, 7486-7491; FIG. 1). The known non-MccJ25-related lariat peptides have lengths of 16-21 residues (FIG. 1). The known non-MccJ25-related lariat peptides contain either: (1) an 8-residue cyclic segment—with a backbone-sidechain amide bond between the backbone nitrogen atom of $Xaa_1$ and the sidechain carboxyl of $Glu_8$ or $Asp_8$—followed by a 9- to 12-residue linear segment; or (2) a 9-residue cyclic segment—with a backbone-sidechain amide bond between the backbone nitrogen atom of $Xaa)$ and the sidechain carboxyl of $Asp_9$—followed by a 7- to 12-residue linear segment (FIG. 1).

Known non-Mcd25-related lariat peptides have lariat-protoknot three-dimensional structures similar to the lariat-protoknot three-dimensional structure of MccJ25. Three-dimensional structures have been determined for several known non-MccJ25-related lariat peptides, including siamycin I (Katahira, et al. (1996) *Bioorg. Med. Chem* 4, 121-129), siamycin II (Constantine, et al. (1995) *J. Biomol. NMR* 5, 271-286), siamycin III (Frechet, et al. (1994) *Biochem.* 33, 42-50)], RES-701-1 (Katahira, et al. (1995) *Bioorg. Med. Chem.* 3, 1273-1280), and lariatin A (Iwatsuki, et al. (2006) *J. Am. Chem. Soc.* 128, 7486-7491). In each case, the compound has been found to have a lariat-protoknot structure, in which the linear segment of the lariat loops back, and penetrates and threads though the cyclic segment of the lariat (Katahira, et al. (1996) *Bioorg. Med. Chem* 4, 121-129; (Constantine, et al. (1995) *J. Biomol. NMR* 5, 271-286; Frechet, et al. (1994) *Biochem.* 33, 42-50); Katahira, et al. (1995) *Bioorg. Med. Chem.* 3, 1273-1280; Iwatsuki, et al. (2006) *J. Am. Chem. Soc.* 128, 7486-7491).

The known non-MccJ25-related lariat peptides have been reported to have useful properties, including antibacterial activity for siamycins (Yano, et al. (1996) *Bioorg. Med. Chem* 4, 115-120; Potterat, et al. (1994) *Liebigs Annalen der Chemie* 7, 741-743), propeptin (Kimura, et al. (1997) *J. Antibiot.* 50, 373-378), and lariatins (Iwatsuki, et al. (2006) *J. Am. Chem. Soc.* 128, 7486-7491); antiviral activity for siamycins (Chokekijchai, et al. (1995) *Antimicrob. Agents Chemother.* 39, 2345-2347; Nakashima, et al. (1996) *Biol. Pharm. Bull.* 19, 405-412; Detlefsen, et al. (1995) *J. Antibiot.* 48, 1515-1517; Lin, et al. (1996) *Antimicrob. Agents Chemother.* 40, 133-138); bacterial RNA polymerase inhibition activity for siamycins (PCT Application Serial No., filed Mar. 13, 2007), RES-701-n (PCT Application Serial No., filed Mar. 13, 2007), and propeptin (PCT Application Serial No., filed Mar. 13, 2007); endothelin type B receptor antagonist activity for RES-701-n (Morishita, et al. (1994) *J. Antibiot.* 47, 269-275; Ogawa, et al. (1995) *J. Antibiot.* 48, 1213-1220); prolyl endopeptidase inhibition activity for propeptin (Kimura, et al. (1997) *J. Antibiot.* 50, 373-378); and atrial natriuretic factor receptor antagonist activity for anantin (Wyss, et al. (1991) *J. Antibiot.* 44, 172-1801).

It is disclosed in PCT Application Serial No. PCT/US2007/006282, filed Mar. 13, 2007 that known non-MccJ25-related lariat peptides, including siamycins, RES-701-n, and propeptin, inhibit bacterial RNAP.

It further is disclosed in PCT Application Serial No. PCT/US2007/006282 that known non-MccJ25-related lariat peptides, including siamycins, RES-701-n, and propeptin, inhibit Gram-negative bacterial RNAP.

It further is disclosed in PCT Application Serial No., filed Mar. 13, 2007 that known non-MccJ25-related lariat peptide, including siamycins, RES-701-n, and propeptin, inhibit Gram-positive bacterial RNAP. This is in contrast to MccJ25, which does not inhibit Gram-positive bacterial RNAP (Yuzenkova, et al. (2002) 277, 50867-50875).

It further is disclosed in PCT Application Serial No. PCT/US2007/006282 that known non-MccJ25-related lariat peptide, including siamycins, RES-701-n, and propeptin, inhibit *Thermus-Deinoccocus* bacterial RNAP, including, for example, *Thermus thermophilus* RNAP. This is in contrast to MccJ25, which does not inhibit *Thermus-Deinoccocus* bacterial RNAP (Yuzenkova, et al. (2002) 277, 50867-50875).

It further is disclosed in PCT Application Serial No. PCT/US2007/006282 that known non-MccJ25-related lariat peptide, including siamycins, RES-701-n, and propeptin, are useful as broad-spectrum inhibitors of bacterial RNAP, being able to inhibit all three classes of bacterial RNAP: i.e., Gram-negative bacterial RNAP, Gram-positive bacterial RNAP, and *Thermus-Deinoccocus* bacterial RNAP. This is in contrast to MccJ25, which is a narrow-spectrum inhibitor of bacterial RNAP, being able to inhibit only Gram-negative bacterial RNAP (Yuzenkova, et al. (2002) 277, 50867-50875).

The known non-MccJ25-related lariat peptides exhibit no significant amino acid similarity to MccJ25 (less than 25% sequence identity; FIG. 1).

The known non-MccJ25-related lariat peptides are produced by bacterial producer strains: *Streptomyces* sp. strains for siamycins, RES-701-n, and anantin (Yano, et al. (1996) *Bioorg. Med. Chem* 4, 115-120; Katahira, et al. (1996) *Bioorg. Med. Chem* 4, 121-129; Chokekijchai, et al. (1995) *Antimicrob. Agents Chemother.* 39, 2345-2347; Nakashima, et al. (1996) *Biol. Pharm. Bull.* 19, 405-412; Detlefsen, et al. (1995) *J. Antibiot.* 48, 1515-1517; Constantine, et al. (1995) *J. Biomol. NMR* 5, 271-286; Helynck, et al. (1993) *J. Antibiot.* 46, 1756-1757; Frechet, et al. (1994) *Biochem.* 33, 42-50; Potterat, et al. (1994) *Liebigs Annalen der Chemie* 7, 741-743; Yamasaki, et al. (1994) *J. Antibiot.* 47, 276-280; Katahira, et al. (1995) *Bioorg. Med. Chem.* 3, 1273-1280; Yano, K. et al. (1995) *J. Antibiot.* 48, 1368-1370; Ogawa, et al. (1995) *J. Antibiot.* 48, 1213-1220; Wyss, et al. (1991) *J. Antibiot.* 44, 172-1801), a *Microbispora* sp. strain for propeptin (Kimura, et al. (1997) *J. Antibiot.* 50, 373-378), and a *Rhodococcus* sp. strain for lariatins (Iwatsuki, et al. (2006) *J. Am. Chem. Soc.* 128, 7486-7491).

Low yields of non-MccJ25-related lariat peptides upon fermentation of the *Streptomyces* sp., *Microbispora* sp., and *Rhodococcus* sp. producer strains have complicated preparation and use of non-MccJ25-related lariat peptides.

It has not been possible to date to re-create the lariat-peptide/lariat-protoknot structure of a non-MccJ25-related lariat peptide without use of the *Streptomyces* sp., *Microbispora* sp., and *Rhodococcus* sp. producer strains. Attempted chemical synthesis of RES-701-1 yields a product having a correct lariat-peptide covalent structure but not having a correct lariat-protoknot three-dimensional structure (i.e., not having the linear segment of the lariat looped back and penetrating and threading through the cyclic segment of the lariat); the resulting material exhibits only 1/700 the biological activity of authentic RES-701-1 (Katahira, et al. (1995) *Bioorg. Med. Chem. Lett.* 5, 1595-1600; He, et al. (1995) *Bioorg. Med. Chem. Lett.* 5, 621-626). Chemical synthesis of a linear analog of RES-701-1 yields a product having neither a lariat-peptide covalent structure nor a lariat-protoknot structure; the resulting material exhibits no detectable biological activity (He, et al. (1995) *Bioorg. Med. Chem. Lett.* 5, 621-626). These negative results are reminiscent of negative results obtained for attempted chemical synthesis of MccJ25 and for chemical synthesis and recombinant production of a linear analog of MccJ25 (Rosengren, et al. (2003) *J. Am. Chem. Soc.* 125, 12464-12474; Wilson, et al. (2003) *J. Am. Chem. Soc.* 125, 12475-12483)

No lariat-peptide/lariat-protoknot biosynthetic cassettes for non-MccJ25-related lariat peptides have been described in prior art. As a consequence, surrogate-host expression of non-MccJ25-related lariat peptides has not been accomplished in prior art. As a further consequence, production of substituted derivatives of non-MccJ25-related lariat peptides has not been accomplished in the prior art. As a further consequence, production of libraries of substituted derivatives of non-MccJ25-related lariat peptides has not been accomplished in prior art. Accordingly, there is exists a need to address these shortcomings in the prior art.

SUMMARY OF THE INVENTION

The invention relates to biosynthesis systems useful for the synthesis of non-MccJ25-related lariat peptides. It is disclosed herein that non-MccJ25-related lariat peptides are produced by lariat-peptide/lariat-protoknot biosynthesis systems, each encoded by a lariat-peptide/lariat-protoknot biosynthesis cassette. It further is disclosed that non-MccJ25-related lariat peptides are not directly genetically encoded, but instead are indirectly genetically encoded, through genetic encoding of a precursor peptide, at least one factor that processes the precursor peptide, and at least one factor that exports the mature non-MccJ25-related lariat peptide from a cell.

Also disclosed is a nucleic acid sequence encoding at least one of a precursor of a non-MccJ25-related lariat peptide, a processing factor for a non-MccJ25-related lariat peptide, and an export factor for a non-MccJ25-related lariat peptide wherein the lariat peptide is a compound according to general structural formula (I):

(I)

wherein:
(i) X is an amino acid residue containing a backbone nitrogen atom;
(ii) Y is an amino acid residue containing a side-chain carboxyl group;
(iii) α is a peptide segment of from about 5 to about 8 amino acid residues;
(iv) β is a peptide segment of from about 6 to about 15 amino acid residues;
(v) there is an amide bond between the backbone nitrogen atom of X and the side-chain carboxyl of Y; and
(vi) wherein the lariat peptide has less than 25% sequence identity with microcin J25 (MccJ25).

Also disclosed is a method of preparing a lariat peptide compound according to general structural formula (I), by
(a) providing a nucleic acid sequence encoding at least one of:
  (i) a precursor of the lariat peptide compound according to general structural formula (I);
  (ii) a processing factor of a lariat peptide according to general structural formula (I); and
  (iii) an export factor of a lariat peptide according to general structural formula (I);
(b) introducing the nucleic sequence into a bacterial host cell;
(c) culturing the nucleic-sequence-containing bacterial host cell; and
(d) isolating a lariat peptide according to general structural formula (I) from at least one of a culture medium and a bacterial cell.

Also disclosed is a method of at least one of identifying or detecting a nucleic acid sequence by:
(a) providing a known nucleic acid sequence that encodes at least one of a precursor of the lariat peptide, a processing factor of a lariat peptide, and an export factor of a lariat peptide, wherein the lariat peptide is a lariat peptide according to general structural formula (I);
(b) contacting a test sample containing at least one nucleic acid sequence of interest with the known nucleic acid sequence; and
(c) detecting hybridization between a nucleic acid sequence of interest and the known nucleic acid sequence.

BRIEF DESCRIPTION OF THE DRAWINGS

FIG. 1 shows the lariat-peptide covalent structures of MccJ25 (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483) and known non-MccJ25-related lariat peptides [siamycin I (also known as MS-271, NP-06, and FR901724; Yano, et al. (1996) *Bioorg. Med. Chem* 4, 115-120; Katahira, et al. (1996) *Bioorg. Med. Chem* 4, 121-129; Chokekijchai, et al. (1995) *Antimicrob. Agents Chemother.* 39, 2345-2347; Nakashima, et al. (1996) *Biol. Pharm. Bull.* 19, 405-412; Detlefsen, et al. (1995) *J. Antibiot.* 48, 1515-1517), siamycin II (Detlefsen, et al. (1995) *J. Antibiot.* 48, 1515-1517; Constantine, et al. (1995) *J. Biomol. NMR* 5, 271-286), and siamycin III (also known as RP 71955 and aborycin; Helynck, et al. (1993) *J. Antibiot.* 46, 1756-1757; Frechet, et al. (1994) *Biochem.* 33, 42-50; Potterat, et al. (1994) *Liebigs Annalen der Chemie* 7, 741-743)], RES-701-n [RES-701-1 (Yamasaki, et al. (1994) *J. Antibiot.* 47, 276-280; Katahira, et al. (1995) *Bioorg. Med. Chem.* 3, 1273-1280), RES-701-2 (Yano, K. et al. (1995) *J. Antibiot.* 48, 1368-1370; Ogawa, et al. (1995) *J. Antibiot.* 48, 1213-1220), RES-701-3 (Ogawa, et al. (1995) *J. Antibiot.* 48, 1213-1220), and RES-701-4 (Ogawa, et al. (1995) *J. Antibiot.* 48, 1213-1220)], propeptin (Kimura, et al. (1997) *J. Antibiot.* 50, 373-378), anantin (Wyss, et al. (1991) *J. Antibiot.* 44, 172-180), and lariatins [lariatin A and lariatin B (Iwatsuki, et al. (2006) *J. Am. Chem. Soc.* 128, 7486-7491)]. Bold lines indicate backbone-sidechain amide linkages; fine lines indicate sidechain-sidechain disulfide linkages; 7-OH—W denotes 7-hydroxytryptophan.

DESCRIPTION OF THE INVENTION

Figure 2:
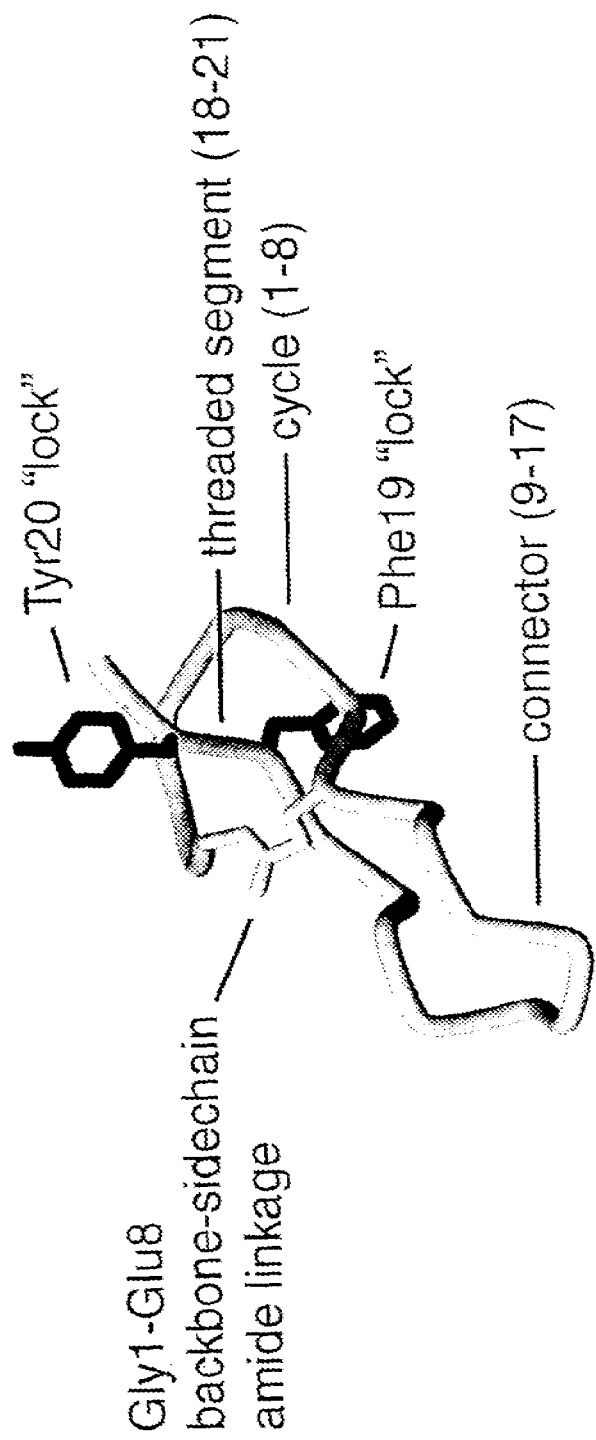
FIG. 2 shows the lariat-protoknot three-dimensional structure of MccJ25 (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483).

The invention relates to biosynthesis systems useful for the synthesis of compounds according to general structural formula (I):

(I)

wherein:
(i) X is an amino acid residue containing a backbone nitrogen atom;
(ii) Y is an amino acid residue containing a side-chain carboxyl group;
(iii) α is a peptide segment of from about 5 to about 8 amino acid residues;
(iv) β is a peptide segment of from about 6 to about 15 amino acid residues;
(v) there is an amide bond between the backbone nitrogen atom of X and the side-chain carboxyl of Y; and
(vi) wherein the compound has less than 25% amino acid sequence identity with MccJ25.

We refer herein to compounds according to general structural formula (I) as "non-MccJ25-related lariat peptides." In a preferred embodiment, X in formula (I) is one of Gly and Cys, and Y in formula (I) is one of Asp and Glu. In a further preferred embodiment, α in formula (I) is a peptide segment of from 6 to 7 amino acid residues, and β in formula (I) is a peptide segment of from 7 to 14 amino acid residues. In an especially preferred embodiment, at least one amino acid residue of β in formula (I) is threaded through the cycle comprising X-α-Y in formula (I).

It is disclosed herein that non-MccJ25-related lariat peptides, including, for example, siamycins, are produced by lariat-peptide/lariat-protoknot biosynthesis systems, each encoded by a lariat-peptide/lariat-protoknot biosynthesis cassette, comprising:
(i) a gene for a precursor of the non-MccJ25-related lariat peptide,
(ii) at least one gene for a factor that processes the precursor of the non-MccJ25-related lariat peptide to yield the mature non-MccJ25-related lariat peptide, and
(iii) at least one gene for a factor that exports the mature non-MccJ25-related lariat peptide from the cell.

It further is disclosed herein that non-MccJ25-related lariat peptides, including, for example, siamycins, are not directly genetically encoded, but, instead, are indirectly genetically encoded, through genetic encoding of:
(i) a precursor of the non-MccJ25-related lariat peptide,
(ii) at least one factor that processes the precursor of the non-MccJ25-related lariat peptide to yield the mature non-MccJ25-related lariat peptide, and
(iii) at least one factor that exports the mature non-MccJ25-related lariat peptide from the cell.

An aspect of this invention is a nucleic acid sequence encoding at least one of a precursor of a non-MccJ25-related lariat peptide, a processing factor for a non-MccJ25-related lariat peptide, and an export factor for a non-MccJ25-related lariat peptide.

Another aspect of this invention is a method to produce a non-MccJ25-related lariat peptide by introduction of a nucleic acid sequence encoding at least one of a precursor of a non-MccJ25-related lariat peptide, a processing factor for a non-MccJ25-related lariat peptide, and an export factor for a non-MccJ25-related lariat peptide, into a host cell.

Another aspect of this invention is a method to detect a nucleic acid sequence encoding at least one of a precursor of a non-MccJ25-related lariat peptide, a processing factor for a non-MccJ25-related lariat peptide, and an export factor for a non-MccJ25-related lariat peptide, by detection of hybridization to a known nucleic acid sequence encoding at least one of a precursor of a non-MccJ25-related lariat peptide, a processing factor for a non-MccJ25-related lariat peptide, and an export factor for a non-MccJ25-related lariat peptide.

Another aspect of this invention is a method to identify a nucleic acid sequence encoding at least one of a precursor of a non-MccJ25-related lariat peptide, a processing factor for a non-MccJ25-related lariat peptide, and an export factor for a non-MccJ25-related lariat peptide, by detection of amino acid sequence similarity to a known nucleic acid sequence encoding at least one of a precursor of a non-MccJ25-related lariat peptide, a processing factor for a non-MccJ25-related lariat peptide, and an export factor for a non-MccJ25-related lariat peptide.

MccJ25, as a direct consequence of its lariat-peptide/lariat-protoknot structure, exhibits two features highly useful for drug design and drug discovery:
(1) MccJ25 is genetically encoded (albeit indirectly, through genetic encoding of a precursor and processing and export factors; Solbiati, et al. (1996) *J. Bacteriol.* 178, 3661-3663; Solbiati, et al. (1999) *J. Bacteriol.* 181, 2659-2662), permitting efficient production by fermentation (Blond, et al. (1999) *Eur. J. Biochem.* 259, 747-755) and permitting efficient construction of derivatives by molecular-biology and directed-evolution methods (WO 2004/023093; U.S. application Ser. No. 11/371,736, filed Mar. 9, 2006; Mukhopadhyay, et al. (2004) *Mol. Cell* 14, 739-751).

(2) MccJ25 is resistant to denaturation and proteolysis (Bayro, et al. (2003) *J. Am. Chem. Soc.* 125, 12382-12383; Rosengren, et al. (2003) *J. Am. Chem. Soc.* 125, 12464-12474; Wilson, et al. (2003) *J. Am. Chem. Soc.* 125, 12475-12483).

This combination of features is not only highly useful, but also highly unusual. Most compounds do not exhibit this combination of features. Most peptides and proteins exhibit only the first feature. Most non-peptide, non-protein compounds exhibit only the second feature.

The non-MccJ25-related lariat peptides of this invention, as a direct consequence of their lariat-peptide/lariat-protoknot structures, are expected to exhibit this same highly useful, highly unusual, combination of features.

The invention has applications in control of bacterial RNA polymerase activity, control of bacterial gene expression, control of bacterial growth, antibacterial chemistry, antibacterial therapy, antiviral chemistry, antiviral therapy.

EXAMPLES

Example 1

Identification and Detection of Nucleic Acid Sequence Encoding Precursor of Non-MccJ25-Related Lariat Peptide Siamycin III Example 1-a Identification of Nucleic Acid Sequence Encoding Precursor of Siamycin III: Primer Design Primers were designed based on the amino acid sequence of siamycin III and on the intention to use the method referred to as "nested 5'-RACE" (Schaefer (1995) *Anal. Biochem.* 227, 255-73; Zhang, et al. (1997) *Methods Mol. Biol* 69, 61-87; Example 1-b), which requires two target-specific primers, one for a "first" or "outer" round of amplification, and one for a "second" or "inner" round amplification.

The linear amino acid sequence of siamycin III (CLGIG-SCNDFAGCGYAVVCFW; Helynck, et al. (1993) *J. Antibiot.* 46, 1756-1757; Frechet, et al. (1994) *Biochem.* 33, 42-50; Potterat, et al. (1994) *Liebigs Annalen der Chemie* 7, 741-743) was back-translated using the universal genetic code to identify all possible DNA coding sequences. Two degenerate primers compatible with all possible DNA coding sequences and with requirements of nested 5'-RACE were designed (Table 1, first and second entries). The lengths and endpoints of the primers were chosen according to considerations well known in the art (Rychlik et al. (1990) *Nucl. Acids Res.* 18, 6409-6412; Mitsuhashi (1996) *J. Clin. Lab. Anal.* 1996 10, 285-293; Linhart et al. (2005) *J. Comput. Biol.* 12, 431-456). Examples of these considerations include: (1) to minimize sequence degeneracy at all positions; (2) to avoid sequence degeneracy at the two positions closest to the primer 3' end; (3), where possible, to avoid sequence degeneracy character at the three positions closest to the primer 3' end; (4), where possible, to avoid A-or-T-rich character at the three positions closest to the primer 3' end; and (5) to yield a predicted melting temperature compatible with hybridization with target nucleic acid sequences under the intended reaction conditions. Applying these considerations, it was determined that back-translated sequences corresponding to cysteine, tryptophan, and phenylalanine residues of siamycin III were likely to be suitable for choice as primer endpoints, and that back-translated sequences corresponding to cysteine and tryptophan residues of siamycin III were likely to be most suitable for choice as primer endpoints. Degenerate positions were specified for synthesis as mixtures (wherein R denotes and equimolar mixture of A and G; Y denotes an equimolar mix of A and T; W denotes an equimolar mix of A and T; S denotes an equimolar mix of G and C; H denotes an equimolar mixture of A, C, and T; and D denotes an equimolar mix of A, G, and T) or as I (wherein I denotes deoxyinosine), according to considerations well known in the art (McPherson (2000) PCR Springer-Verlag, NY).

TABLE 1

Identification of nucleic acid sequence encoding precursor of siamycin III: primer design.

| SEQ ID | application | primer sequence* | back-translated amino acid sequence |
|---|---|---|---|
| SEQ ID 1 | 5'-RACE, first round | CCARAACAIACIACIGCRTAICCRCA | CGYAVVCFW |
| SEQ ID 2 | 5'-RACE, second round | AARTCRTTRCAISWICCDATICCIARRCA | CLGIGSCND |

*Degenerate positions were synthesized as mixtures (wherein R denotes an equimolar mixture of A and G; Y denotes an equimolar mix of A and T; W denotes an equimolar mix of A and T; S denotes an equimolar mix of G and C; H denotes an equimolar mixture of A, C, and T; and D denotes an equimolar mix of A, G, and T) or as I (wherein I denotes deoxyinosine).

Example 1-b

Identification of Nucleic Acid Sequence Encoding Precursor of Siamycin III: 5'-RACE

*Streptomyces griseoflavus* strain Tü 4072 (Potterat, et al. (1994) *Liebigs Annal. Chem.* 7, 741-743; provided by Combinature Biopharm AG) was cultured in 50 ml YD (10 g/l yeast extract; 10 g/l dextrose) medium, with shaking, for 96 h at 28° C. Cells were collected by centrifugation (16000 g, 10 min at 4° C.), washed twice with 50 ml TES (10 mM Tris, pH8.0, 1 mM EDTA), 50 mM NaCl, and re-suspended in 20 ml TES. Total RNA was isolated by use of the UltraClean Microbial RNA Isolation Kit (MO Bio Laboratories, Inc.) and was purified from traces of genomic DNA by use of RNase-Free DNase (QIA-Gen, Inc.) on an RNeasy Midi Kit spin column (QIA-Gen, Inc.). The final concentration of RNA obtained was ~2 mg/ml, as assessed based on UV absorbance.

5'-RACE (Schaefer (1995) *Anal. Biochem.* 227, 255-73) was performed by use of the FirstChoice RLM-RACE Kit (Ambion, Inc.). 1 µl total RNA (2 µg) was added to a 5'-RACE-adaptor-ligation reaction mixture (9 µl) containing 1 µl 5'-RACE adaptor, 2 µl T4 RNA ligase (2.5 U/µl), 1 µl 10×RNA ligase buffer, and 5 µl nuclease-free water, and the reaction was allowed to proceed for 1 h at 37° C. The resulting 5'-RACE-adaptor-ligated total RNA (2 µl), was added to a cDNA synthesis reaction mixture (19 µl) containing 2 µl random decamers, 1 µl M-MLV reverse transcriptase (RT; 100 U/µl), 1 µl RNase inhibitor, 4 µl dNTP mix, 2 µl 10 RT buffer, and 10 µl nuclease-free water, and the reaction was allowed to proceed for 1 h at 42° C. The resulting 5'-RACE-adaptor-containing cDNA (1 µl) was added to a first-round 5'-RACE PCR reaction mixture (49 µl) containing 2 µl first-round target-specific primer (SEQ ID 1; Example 1-a; 1 µM), 2 µl first-round 5'-RACE primer, 0.25 µl Super Taq DNA polymerase (5 U/µl), 4 µl dNTP mix, 5 µl 10×PCR buffer, and 38.5 µl nuclease-free water, and first-round 5'-RACE PCR was performed (initial denaturation for 3 min at 94° C.; followed by 35 cycles each comprising denaturation for 30 s at 94° C., annealing for 30 s at 53° C., and extension for 1 min at 72° C.; followed by final extension for 7 min at 72° C.). The resulting first-round 5'-RACE PCR product (1 µl) was added to a second-round 5'-RACE PCR reaction mixture, and second-round 5'-RACE PCR was performed (procedures identical to those for first-round 5-RACE PCR, except for use of the second-round target-specific primer SEQ ID 2 and the second-round 5'-RACE primer).

Products were analyzed by agarose gel electrophoresis (Sambrook, et al. (1989) *Molecular Cloning: A Laboratory Manual*, Cold Spring Harbor Press, Cold Spring Harbor N.Y.). A distinct product with a size of approximately 200 bp was observed. The product was extracted from the gel and ligated with the TOPO4 Sequencing Vector (Invitrogen, Inc.; procedures per instructions of the manufacturer), and the resulting recombinant plasmid DNA was introduced by transformation into chemically competent cells of *Escherichia coli* strain DH5α chemically competent cells (hsdR17 recA1 relA1 endA1 gyrA96 gal deoR phoA supE44 thi Δ(lacZYA-argF)U169 φ80dlacZΔM15; invitrogen, Inc.; procedures per instructions of the manufacturer). Transformants were inoculated into 2 ml LB (Sambrook, et al. (1989) *Molecular Cloning: A Laboratory Manual*, Cold Spring Harbor Press, Cold Spring Harbor N.Y.) containing 50 µg/ml ampicillin and cultured with vigorous shaking for 12 h at 37° C., plasmid DNA was isolated by use of the QIA-gene Plasmid DNA Purification Kit (QIA-Gen, Inc.; procedures per instructions of the manufacturer), and plasmid DNA was subjected to restriction analysis (EcoRI digestion followed by agarose gel electrophoresis). For six of six tested transformants, plasmid DNA was found to contain an insert with the size of the product (approximately 200 bp). For two plasmids found to contain an insert with the size of the product, the insert was subjected to dideoxy nucleotide sequencing (Sambrook, et al. (1989) *Molecular Cloning: A Laboratory Manual*, Cold Spring Harbor Press, Cold Spring Harbor N.Y.), sequencing inward from both ends by use of sequencing primers supplied with the TOPO4 Sequencing Vector (Invitrogen, Inc.). [Unless otherwise specified, this or an equivalent cloning and sequencing strategy was used in all experiments described in the Examples.]

BLAST analysis (Altschul, et al. (1990) *J. Mol. Biol.* 215, 403-410) revealed that the cloned approximately 200 bp product exhibited no detectable similarity to sequences within the GENBank DNA Database. Upon subtraction of 5'-RACE-adaptor-derived, and 5'-RACE-primer derived nucleic acid sequences, the cloned approximately 200 bp product yielded 125 by of putative target-derived nucleic acid sequence. The resulting putative target-derived nucleic acid sequence is as follows (SEQ ID 3):

```
TTCCCGGACAGGTCACGGGGCCGAAAAGGTCGGCCCGGGCCGTTCGACCC
ACGGGAGGAACCATGACCGCGATCTACGAGCCGCCCGCCCTGCAGGAGAT
CGGCGACTTCGACGAGCTCACCAAG
```

Example 1-c

Identification of Nucleic Acid Sequence Encoding Precursor of Siamycin III: 3'-RACE Primers for nested 3'-RACE (Schaefer (1995) *Anal. Biochem.* 227, 255-73) were designed based on the putative target-derived nucleic acid sequence obtained in Example 1-b (SEQ ID 3):

first-round 3'-RACE primer (SEQ ID 4; corresponds to positions 6-30 of SEQ ID 3):

```
GGACAGGTCACGGGGCCGAAAAGGT
``` second-round 3'RACE primer (SEQ ID 5; corresponds to positions 50-79 of SEQ ID 3):

```
CACGGGAGGAACCATGACCGCGATCTACGA
```

3'-RACE was performed by use of the Poly(A) Tailing Kit (Ambion, Inc.; procedures essentially per instructions of the manufacturer) and FirstChoice RLM-RACE Kit (Ambion, Inc.; procedures essentially per instructions of the manufacturer). 4 µl *Escherichia coli* poly(A) polymerase (E-PAP; 0.75 units/µl) was added to a 3'-poly(A)-tailing reaction mixture (96 µl) containing 5 µl total RNA (2 µg/µ; Example 1-b), 10 µl 10 mM ATP, 10 µl 5 mM MnCl$_2$, 20 µl 5×E-PAP buffer, and 51 µl nuclease-free water, and, following, 45 min at 37° C., reaction products were phenol-chloroform extracted, ethanol precipitated, and re-suspended in 20 µl nuclease-free water. The resulting poly3'-(A)-tailed total RNA (1 µl) was added to a cDNA-synthesis reaction mixture (19 µl) containing 2 µl 3'-RACE adaptor, 1 µl M-MLV RT (100 U/µl), 1 µl RNase inhibitor, 4 µl dNTP mix, 2 µl 10×RT buffer, and 9 µl nuclease-free water, and the reaction was allowed to proceed for 1 h at 42° C. The resulting 3'-RACE-adaptor containing cDNA (1 µl) was added to a first-round 3'-RACE PCR reaction mixture (49 µl) containing 2 µl first-round target-specific primer (SEQ ID 4; 1 µM), 2 µl first-round 3'-RACE primer, 0.25 µl Super Taq DNA polymerase (5 U/µl), 4 µl dNTP mix, 5 µl 10×PCR buffer, and 35.75 µl nuclease-free water, and first-round 3'-RACE PCR was performed (initial denaturation for 3 min at 94° C.; followed by 35 cycles each comprising denaturation for 30 s at 94° C., annealing for 30 s at 65° C., and extension for 30 s at 72° C.; followed by final extension for 7 min at 72° C.). The resulting first-round 3'-RACE PCR product (1 µl) was added to a second-round 3'-RACE PCR reaction mixture, and second-round 3'-RACE PCR was performed (procedures identical to those for first-round 3-RACE PCR, except for use of second-round target-specific primer SEQ ID 5 and second-round 3'-RACE primer, and use of an annealing temperature of 60° C.).

Agarose gel electrophoresis revealed a single distinct product, with a size of approximately 200 bp. The product was extracted from the gel, cloned into the TOPO4 Sequencing Vector (Invitrogen, Inc.; procedures per instructions of the manufacturer), and sequenced. Upon subtraction of 3'-RACE-adaptor-derived, and 3'-RACE-primer-derived nucleic acid sequences, the product yielded 119 bp of putative target-derived nucleic acid sequence: 46 bp of putative target-derived sequence identical to putative target-derived sequence identified by 5'-RACE (Example 1-b) and 73 bp of new putative target-derived nucleic acid sequence.

The 195 bp sequence obtained by combining the results of 5'-RACE (Example 1-b) and 3'-RACE (Example 1-c) is as follows (SEQ ID 6):

TTCCCGGACAGGTCACGGGGCCGAAAAGGTCGGCCCGGGCCGTTCGACCC

ACGGGAGGAACCATGACCGCGATCTACGAGCCGCCCGCCCTGCAGGAGAT

CGGCGACTTCGACGAGCTCACCAAGTGCCTCGGCATCGGGAGCTGCAACG

ACTTCGCCGGCTGCGGTTACGCCGTCGTCTGCTTCTGGTGATCGC

The 195 bp sequence contains a single open reading frame (ORF) 42 codons in length. The ORF contains an ATG start codon at position 63, preceded by a Shine-Dalgarno sequence (Shine, et al. (1975) *Nature* 254, 34-38), and contains an TGA stop codon at position 189. The last 21 amino acid residues encoded by the ORF (i.e., CLGIGSCNDFAGCGYAV-VCFW) correspond exactly to the 21 amino acid residues of siamycin III (i.e., CLGIGSCNDFAGCGYAVVCFW). The three amino acid residues that precede the last 21 amino acid residues encoded by the ORF (i.e., LTK) correspond exactly to the three amino acid residues of the precursor of MccJ25 that precede the 21 amino acid residues of mature MccJ25 (i.e., LTK; see Solbiati, et al. (1999) *J. Bacteriol.* 181, 2659-2662). We infer that the ORF represents the gene for the precursor to siamycin III and that siamycin III is biosynthesized by a precursor-dependent mechanism similar to the precursor-dependent mechanism employed in biosynthesis of MccJ25. We designate the ORF siaA-III Example 1-d Detection of Nucleic Acid Sequence Encoding Precursor of Siamycin III: Detection in Producer-Strain RNA Detection of nucleic acid sequences encoding the precursor of siamycin III in producer-strain RNA by use of 5'-RACE is described in Example 1-b.

Detection of nucleic acid sequences encoding the precursor of siamycin III in producer-strain RNA by use of 3'-RACE is described in Example 1-c.

Example 1-e

Detection of Nucleic Acid Sequence Encoding Precursor of Siamycin III: Detection in Producer-Strain Genomic DNA

*Streptomyces griseoflavus* strain Tü 4072 (Potterat, et al. (1994) *Liebigs Annal. Chem.* 7, 741-743; provided by Combinature Biopharm AG) was cultured in 50 ml YD (10 g/l yeast extract; 10 g/l dextrose) medium, with vigorous shaking, for 72 h at 28° C. Cells were collected by centrifugation (16000 g, 10 min at 4° C.), washed twice with 50 ml TES (10 mM Tris, pH8.0, 1 mM EDTA, 50 mM NaCl, and re-suspended in 10 ml 20% (w/v) sucrose, 20 mM Tris-HCl, pH 8.0, 0.5 M NaCl, and 12.5 mM EDTA. Lysozyme was added to a final concentration of 2 mg/ml, and samples were incubated 2 h at 37° C. with shaking. SDS was added to a final concentration of 1%, and tubes were gently rocked. (From this stage onward, the solution was handled carefully to minimize mechanical shearing of genomic DNA.) DNase-free proteinase K (Epicentre, Inc.) was added to a final concentration of 1 mg/ml, and incubation was continued for 2 h at 50° C. Samples were diluted with 10 ml TE (10 mM Tris, pH8.0, and 1 mM EDTA) and were extracted three times with 10 ml water-saturated phenol, two times with 10 ml phenol-chloroform (1:1, vol/vol), and 2 times with 10 ml chloroform. Genomic DNA was precipitated by addition of 20 ml 100% ethanol, washed four times with 20 ml 70% ethanol, and washed once with 20 ml 100% ethanol, and redissolved in 10 ml TE (10 mM Tris-HCl, pH8.0, 0.1 mM EDTA) by incubation 12 h at 4° C.

Genomic DNA (1 µl of a 2 µl aliquot diluted 100× with TE) was added to a PCR reaction mixture (49 µl) containing 2 µl target-specific forward primer GACCCACGGGAGGAAC-CATGACCGC (SEQ ID 7; corresponds to positions 46-70 of SEQ ID 6; 1 µM), 2 µl target-specific reverse primer GCG-TAACCGCAGCCGGCGAAGTCGTTGCA (SEQ ID 8; corresponds to complement of positions 144-172 of SEQ ID 6; 1 µM), 0.5 µl of Phusion High-Fidelity DNA Polymerase (FINNZYMES, Inc.; 2 U/µl), 1 µl 10 mM dNTP mix, 10 µl 5× Phusion HF buffer, 1.5 µl DMSO, and 32 µl and nuclease-free water, and PCR was performed (initial denaturation for 30 s at 95° C.; followed by 35 cycles each comprising denaturation for 10 s at 98° C., annealing for 15 s at 64° C., and extension 30 s at 72° C.; followed by final extension for 10 min at 72° C.). Products were analyzed by agarose (2%) gel electrophoresis. A single distinct product was observed, with a size of approximately 130 bp was observed. The product was eluted from the gel, cloned into the TOPO4 Sequencing Vector (Invitrogen, Inc.), and sequenced. The sequence corresponded to the expected 127 bp sequence (SEQ ID 9):

GACCCACGGGAGGAACCATGACCGCGATCTACGAGCCGCCCGCCCTGCAG

GAGATCGGCGACTTCGACGAGCTCACCAAGTGCCTCGGCATCGGGAGCTG

CAACGACTTCGCCGGCTGCGGTTACGC

Detection of nucleic acid sequences encoding the precursor of siamycin III, and detection of flanking nucleic acid sequences, also was accomplished by use of genome walking (Genome Walker Kit; Clontech, Inc.; procedures per instructions of the manufacturer). In this strategy, genomic DNA was fragmented by digestion, in parallel, with restriction endonucleases EcoRV, NaeI, PvuII, and RsaI; resulting genomic DNA fragments were pooled and ligated to the Genome Walker adaptor provided with the kit; resulting adaptor-ligated pooled genomic DNA fragments were subjected to nested PCR (first-round PCR reaction using the outer adaptor primer provided with the kit and an outer target-specific primer; second-round PCR reaction using the inner adaptor primer provided with the kit and an inner target-specific primer); and resulting products were isolated by agarose gel electrophoresis, cloned into plasmid pT7Blue (Novagen, Inc.; cloning performed by use of the Novagen Perfectly Blunt Cloning Kit), and sequenced. The 388 bp sequence obtained by combining the results of 5'-RACE (Example 1-b), 3'-RACE (Example 1-c), and cycles of Genome Walking (Example 1-e) is as follows (SEQ ID 10):

CCGGCACCGTTCGTGGGACGGGTGACGGGACGCGCCTGAGGCATGTGCCC

CATGCGCGTGGGACATGGCCCCTCGTAGGTTCCCGGACAGGTCACGGGGC

CGAAAAGGTCGGCCCGGGCCGTTCGACCCACGGGAGGAACCATGACCGCG

ATCTACGAGCCGCCCGCCCTGCAGGAGATCGGCGACTTCGACGAGCTCAC

CAAGTGCCTCGGCATCGGGAGCTGCAACGACTTCGCCGGCTGCGGTTACG

CCGTCGTCTGCTTCTGGTGATCGCACCGGTGCCGGTGTGCCCCTCGTGGG

CACACCGGCACCGCCCGGGGAGTGAGGCGACATGGAATTCACAGTGCTT

CCGGACTGTCCCGCCGGCGCCGCGCTGGCGGACCGGGT

Example 2

Identification and Detection of Nucleic Acid Sequence Encoding Precursor of Non-MccJ25-Related Lariat Peptide Siamycin I Example 2-a Identification of Nucleic Acid Sequence Encoding Precursor of Siamycin I: Primer Design Nucleic acid sequences encoding the precursor of siamycin I were detected in, and isolated from, producer-strain genomic DNA by use of nested PCR.

Primers were designed based on the nucleic acid sequence encoding the precursor of the related lariat peptide siamycin III (SEQ ID 6; Example 1-c), taking into account the two amino acid sequence differences between siamycin I and siamycin III (Val vs. Ile at position 4 and Ile vs. Val at position 17; FIG. 1.). Two forward primers and two reverse primers, each 25-30 nt in length, were designed:

first-round forward primer (SEQ ID 4; corresponds to positions 6-30 of SEQ ID 6):

GGACAGGTCACGGGGCCGAAAAGGT first-round reverse primer (SEQ ID 11; corresponds to complement of positions 162-188 of SEQ ID 6, altered to take into account the two amino acid sequence differences between siamycin I and siamycin III, with R denoting an equimolar mixture of A and G, and with N denoting an equimolar mixture of A, G, C, and T):

CCAGAAGCAGACNATGGCGTAACCRCA second-round forward primer (SEQ ID 7; corresponds to positions 46-70 of SEQ ID 6):

GACCCACGGGAGGAACCATGACCGC second-round reverse primer 1 (SEQ ID 8: corresponds to complement of positions 144-172 of SEQ ID 6):

GCGTAACCGCAGCCGGCGAAGTCGTTGCA

Example 2-b

Identification of Nucleic Acid Sequence Encoding Precursor of Siamycin I: PCR

*Streptomyces* sp. strain SKH-2344 (Chokekijchai, et al. (1995) *Antimicrob. Agents Chemother.* 39, 2345-2347) was provided by H. Mitsuya (National Institutes of Health, Bethesda Md.). Cells were cultured, with shaking, for 72 h at 30° C. in baffled flasks containing 50 ml YD (10 g/l yeast extract, 10 g/l dextrose, pH 7.0). Cells were collected by centrifugation at 16000 g, for 15 min at 4° C., washed twice with 50 ml TES (10 mM Tris, pH8.0, 1 mM EDTA, 50 mM NaCl), and re-suspended in 10 ml 20 mM Tris-HCl, pH 8.0, 20% (w/v) sucrose, 0.5 M NaCl, and 12.5 mM EDTA. Lysozyme was added to a final concentration of 2 mg/ml, and the sample was incubated, with shaking, for 2 h at 37° C. SDS (to a final concentration of 1%) and DNase-free proteinase K (Epicentre, Inc.; to a final concentration of 1 mg/ml) were added, and the sample was incubated 4 h at 50° C. The sample then was diluted with 10 ml TE (10 mM Tris, pH 8.0, and 1 mM EDTA) and was extracted three times with 20 ml phenol: chloroform (1:1, vol/vol) and two times with 20 ml chloroform. DNA was precipitated by addition of 20 ml ethanol, washed three times with 20 ml 70% ethanol, and once with ethanol, and dissolved in 2 ml TE by incubation 12 h at 4° C. DNA concentration and purity were determined by measurements of absorbance at 260 nm and 280 nm and by electrophoresis in agarose gel.

First-round PCR was performed in reaction mixtures (50 d) containing 0.1-0.2 µg genomic DNA, 0.5 µM forward primer (SEQ ID 4), 0.5 µM reverse primer (SEQ ID 11), 1 U Phusion DNA polymerase (New England Biolabs, Inc.), 200 µM each dNTP, 1×GC buffer (New England Biolabs, Inc.), and 3% DMSO (initial denaturation for 30 s at 98° C.; followed by 35 cycles, each comprising denaturation for 10 s at 98° C., annealing for 15 s at 64° C., and extension for 30 s at 72° C.; followed by final extension for 5 min at 72° C.). The resulting first-round PCR product (1 µl of 1:50 dilution) was subjected to a second-round PCR reaction (procedures as in the first-round PCR reaction, but with use of SEQ ID 7 as forward primer and SEQ ID 8 as reverse primer).

Agarose gel electrophoresis revealed a single distinct product, with the expected size of 129 bp. The product was extracted from the gel, cloned into the TOPO4 Sequencing Vector (Invitrogen, Inc.; procedures per instructions of the manufacturer), and sequenced. Upon subtraction of primer-derived nucleic acid sequences, the product yielded 73 bp of target-derived nucleic acid sequence (SEQ ID 13):

GATCTACGAGCCCCCCATGCTCCAGGAAGTCGGCGACTTCGAGGAGCTCA

CGAAGTGCCTCGGCGTCGGAAGC

The 73 bp target-derived sequence (SEQ ID 13) exhibits 85% nucleotide-sequence identity with the sequence encoding the precursor of siamycin III (SEQ ID 6; Example 1-c). The 73 bp target-derived sequence (SEQ ID 13) comprises a partial ORF encoding a product that exhibits 83% amino-acid-sequence identity with the precursor of siamycin III (Example 1-c). The last six amino acid residues encoded by the partial ORF (i.e., CLGVGS) correspond exactly to amino acid residues 1 to 6 of siamycin I (i.e., CLGVGS) (and reflect the expected $Val_4$-vs.-$Ile_4$ difference between siamycin I and siamycin III). We infer that the partial ORF represents part of the gene for the precursor to siamycin I.

Further identification of nucleic acid sequences encoding the precursor of siamycin I, and also of flanking DNA nucleic acid sequences, was accomplished by use of genome walking (Genome Walker Kit; Clontech, Inc.; procedures per instructions of the manufacturer). In this strategy, genomic DNA was fragmented by digestion, in parallel, with restriction endonucleases EcoRV, NaeI, PvuII, RsaI, and StuI; resulting genomic DNA fragments were pooled and ligated to the Genome Walker adaptor provided with the kit; resulting adaptor-ligated pooled genomic DNA fragments were subjected to nested PCR (first-round PCR reaction using the outer adaptor primer provided with the kit and an outer target-specific primer, SEQ ID 14, SEQ ID 15, or SEQ ID 17; second-round PCR reaction using the inner adaptor primer provided with the kit and an inner target-specific primer, SEQ ID 16, SEQ ID 18, or SEQ ID 19); and resulting products were isolated by agarose gel electrophoresis, cloned into plasmid pT7Blue (Novagen, Inc.; cloning performed by use of the Novagen Perfectly Blunt Cloning Kit), and sequenced. The 477 bp sequence obtained by combining the results of PCR probing (previous paragraph) and cycles of Genome Walking (this paragraph) is as follows (SEQ ID 20):

```
ACTTCCCCGACCAGGCGGGAAACGAACTGCTCACCGTCCGGTCCCCGCAC
ACGGCCTTCGGCTTCACGGTGCTGCTCGCCTGGACCGTCGCCGCCCTCGG
ATGGGGCTGGGTGCGCCAGCGCCGGTGGGACAGCTGACAGGACCGGCATG
GGACAACTGCCCCATGCCGGTGGGACAGTCCGCCCCGTAGCTTCCGTGAC
AGATCACAGGCCGAACAAGGTCGGCCTGACCGATCCGAAACGGGAGGACA
CCATGTCCGCGATCTACGAGCCCCCATGCTCCAGGAAGTCGGCGACTTC
GAGGAGCTCACGAAGTGCCTCGGCGTCGGAAGCTGCAACGACTTCGCCGG
CTGCGGCTACGCGATCGTCTGCTTCTGGTGATCACGTCCGGTGCCGGTGC
GTTCACGCGCACCGGCACCACCCGGGGTGACGAGGAGACGGGGAACGAGG
CGACATGGAATTCGTGGTTCTTCCGGA
```

The 477 bp sequence contains an ORF 43 codons in length. The ORF contains an ATG start codon at position 253, preceded by a Shine-Dalgarno sequence (Shine, et al. (1975) *Nature* 254, 34-38), and contains an TGA stop codon at position 378. The last 21 amino acid residues encoded by the ORF (i.e., CLGVGSCNDFAGCGYAIVCFW) correspond exactly to the 21 amino acid residues of siamycin I (i.e., CLGVGSCNDFAGCGYAIVCFW). The three amino acid residues that precede the last 21 amino acid residues encoded by the ORF (i.e., LTK) correspond exactly to the three amino acid residues of the precursor of MccJ25 that precede the 21 amino acid residues of mature MccJ25 (i.e., LTK; see Solbiati, et al. (1999) *J. Bacteriol.* 181, 2659-2662) and to the three amino acid residues of the precursor of siamycin III that precede the 21 amino acid residues of mature siamycin III (i.e., LTK; Example 1-b). The product encoded by the ORF exhibits 86% amino acid sequence identity with the precursor of siamycin III (Example 1-b). We infer that the ORF represents the gene for the precursor to siamycin I and that siamycin I is biosynthesized by a precursor-dependent mechanism similar to the precursor-dependent mechanism employed in biosynthesis of MccJ25 and biosynthesis of siamycin III. We designate the ORF siaA-I.

Example 2-c

Detection of Nucleic Acid Sequence Encoding Precursor of Siamycin I: Detection in Producer-Strain RNA Detection of nucleic acid sequences encoding the precursor of siamycin I in producer-strain RNA was accomplished by use of primer extension.

Primers were designed based on the partial sia-I-locus nucleic acid sequence obtained in Example 2-b (SEQ ID 20): primer 1 (SEQ ID 21: corresponds to complement of positions 307-333 of SEQ ID 20):

```
GCTTCCGACGCCGAGGCACTTCGTGAG
``` primer 2 (SEQ ID 22; corresponds to complement of positions 283-312 of SEQ ID 20)

```
CGTGAGCTCCTCGAAGTCGCCGACTTCCTG
```

*Streptomyces* sp. strain SKH-2344 (Chokekijchai, et al. (1995) *Antimicrob. Agents Chemother.* 39, 2345-2347) provided by H. Mitsuya (National Institutes of Health, Bethesda Md.) was cultured in 50 ml YD (10 g/l yeast extract, 10 g/l dextrose, pH 7.0), with shaking, for 96 h at 30° C. Cells were collected by centrifugation (16000 g, 10 min at 4° C.), and total RNA was extracted using the RiboPure Bacteria RNA isolation kit (Ambion, Inc.; procedures per instructions of the manufacturer, but with a cell-lysis time of 1 h). RNA concentration and purity were determined by measurements of absorbance at 260 nm and 280 nm and by formaldehyde-agarose gel electrophoresis (Sambrook, et al. (1989) *Molecular Cloning: A Laboratory Manual*, Cold Spring Harbor Press, Cold Spring Harbor N.Y.).

Primer-extension reactions were performed using total RNA (10 g), $^{32}$P-end-labelled primer (1 pmol; SEQ ID 21 or SEQ ID 22) and Super Script III reverse transcriptase (Invitrogen, Inc.; 100 U; procedures essentially per instructions of the manufacturer). Primers were annealed by incubation for 20 min at a temperature equal to the calculated melting temperature, followed by incubation for 10 min at 22° C. Primers were extended by incubation for 50 min at 50° C. Reactions were terminated by incubation for 5 min at 85° C., followed by digestion of RNA with RNase II. Products were extracted with chloroform, precipitated with ethanol, dissolved in formamide-containing loading buffer. To provide molecular-mass markers, dideoxy nucleotide-sequencing reactions were performed on a corresponding PCR product from genomic DNA using the same $^{32}$P-end-labelled primers (fmol DNA Cycle Sequencing System; Promega, Inc.; procedures per instructions of the manufacturer). Primer-extension products and dideoxy nucleotide sequencing products subjected to electrophoresis on an 8% sequencing gel, and products were detected by storage-phosphor imaging (procedures essentially as in (Sambrook, et al. (1989) *Molecular Cloning: A Laboratory Manual*, Cold Spring Harbor Press, Cold Spring Harbor N.Y.).

A single distinct primer-extension product was observed for each of the two primers: a product 133 nt in length for primer SEQ ID 21, and a product 112 nt in length for SEQ ID 22. The results map the transcription start site of the siaA-I RNA to a position 52 nt 5' to the siaA-I translation start codon (i.e., position 201 of SEQ ID 20). The transcription start site is part of a sequence that conforms to the consensus promoter sequence recognized by the primary σ factor of *Streptomyces* sp., HrdB (Bourn, et al. (1995) *Nucl. Acid Res.* 23, 3696-703). We designate this sequence the sia-I promoter, siaP-I.

Example 2-d

Detection of Nucleic Acid Sequence Encoding Precursor of Siamycin I: Detection in Producer-Strain Genomic DNA Detection of nucleic acid sequences encoding the precursor of siamycin I in producer-strain genomic DNA by use of PCR probing is described in Example 2-b and Example 4b.

Detection of nucleic acid sequences encoding the precursor of siamycin I in producer-strain genomic DNA by use of genome walking is described in Example 2-b.

Detection of nucleic acid sequences encoding the precursor of siamycin I in producer-strain genomic DNA by use of colony hybridization is described in Example 4-b.

Example 3

Isolation and Characterization of Nucleic Acid Sequences Encoding Precursor, Processing Factors, and Transport Factors for Non-MccJ25-Related Lariat Peptide Siamycin III Example 3-a Isolation of Nucleic Acid Sequences Encoding Precursor, Processing Factors, and Transport Factors for Siamycin III: Preparation of Producer-Strain Genomic DNA Library Genomic DNA of *Streptomyces griseoflavus* strain Tü 4072 (Potterat, et al. (1994) *Liebigs Annal. Chem.* 7, 741-743; provided by Combinature Biopharm AG) was prepared as described in Example 1-e. A 16-fold-coverage genomic DNA library was prepared by use of the pWEB-TNC Cosmid Cloning Kit (Epicentre, Inc.; procedures per instruction of the manufacturer with minor modifications). Genomic DNA (20 µg in four aliquots of 5 µg each) was digested with restriction endonuclease HaeIII under conditions that yield partial digestion and result in genomic DNA fragments with a mean size ~35,000 to ~45,000 bp. Four aliquots of genomic DNA (5 µg each) were incubated, in parallel, with 0.01 U, 0.02 U, 0.05 U, and 0.1 U HaeIII in 100 µl 1×HaeIII buffer for 1 h at 37° C. The reaction mixtures were combined, and the reaction products were extracted with 400 µl phenol-chloroform (1:1, vol/vol), ethanol precipitated, and re-dissolved in 52 µl TE. The resulting genomic DNA fragments (52 µl) were added to an end-repair reaction mixture (28 µl) containing 4 µl end-repair enzyme mix (contains T4 DNA polymerase and T4 polynucleotide kinase; provided with the kit), 8 µl 2.5 mM dNTP mix, 8 µl 10 mM ATP, and 8 µl 10× end-repair buffer, and the reaction was allowed to proceed for 45 min at 25° C. The resulting end-repaired genomic DNA fragments were size-selected by gel electrophoresis on 1% low-melting-point agarose (Invitrogen, Inc.); excision of a 2-4 mm gel segment corresponding to a DNA fragment size of ~35,000 bp to ~45,000 bp (sizes inferred based on ethidium-bromide-stained T7 DNA markers); addition of 3 µl GELase (1 U/µl; provided with the kit) and 20 µl 50× GELase buffer and incubation 30 min at 45° C. followed by incubation 10 min at 70° C.; addition of 1 ml 5 M ammonium acetate and removal of insoluble material by centrifugation; precipitation with two volumes 100% ethanol; and re-suspension in 40 µl TE (10 mM Tris-HCl, pH8.0, 0.1 mM EDTA). The resulting size-selected end-repaired genomic DNA fragments (0.3 µg in 5 µl) were added to a ligation reaction mixture (15 µl) containing 1 µl 0.5 µg/µl pWEB-TNC, 1 µl U/µl Fast-Link DNA ligase, 1 µl 10 mM ATP, 2 µl 10× fast-link ligation buffer, and 10 µl nuclease-free water; the reaction was allowed to proceed for 2 h at 22° C.; and the reaction was terminated by heat-inactivation of DNA ligase by incubation 10 min at 70° C. 10 µl of resulting recombinant DNA (0.4 µg) was added to an in-vitro-packaging reaction containing 20 µl in-vitro-packaging extract (provided with the kit), the reaction was allowed to proceed 90 min at 30° C., a further 20 µl in-vitro-packaging extract (provided with the kit) was added, the reaction was allowed to proceed a further 90 min at 30° C., and the reaction was terminated by addition of 500 µl phage dilution buffer (10 mM Tris-HCl, pH 8.3; 100 mM NaCl, and 10 mM $MgCl_2$) and 25 µl chloroform and transfer to 4° C. 500 µl of resulting recombinant phage stock ($1.2 \times 10^4$ CFU/ml; titer determined per instructions provided with the kit) was mixed with 5 ml *Escherichia coli* strain EPI100T1$^R$ [Δ(mrr-hsdRMS-msrBC) mcrA lacX74 recA1 Φ80dlacZΔ M15; provided with the kit] and incubated 20 min at 37° C.; procedures per instructions provided with the kit], dilutions yielding 200-300 recombinant-cosmid-containing clones were plated on L-agar (Sambrook, et al. (1989) *Molecular Cloning: A Laboratory Manual*, Cold Spring Harbor Press, Cold Spring Harbor N.Y.) containing 30 µg/ml ampicillin, and plates were incubated 18 h at 37° C. The resulting recombinant-cosmid-containing clones were eluted from plates in LB (5 ml/plate) and were combined on ice to yield four pools, each containing ~500-1500 clones. For each resulting pool of recombinant-cosmid-containing clones, clones were collected by centrifugation, washed two times with 10 ml LB, re-suspended in 7 ml LB, supplemented with 3 ml 50% glycerol, and frozen at −70° C.

Example 3-b

Isolation of Nucleic Acid Sequences Encoding Precursor, Processing Factors, and Transport Factors for Siamycin III: Screening of Producer-Strain Genomic DNA Library To screen pools of recombinant-cosmid-containing clones (Example 3-a) for sia-III-locus nucleic acid sequences, PCR probing, involving a first round and second round of nested PCR, was employed. Primers were designed based on the partial sia-III-locus nucleic acid sequences obtained in Example 1-e (SEQ ID 10):
first round forward primer (SEQ ID 4; corresponds to positions 85-109 of SEQ ID 10):

GGACAGGTCACGGGGCCGAAAAGGT first-round reverse primer (SEQ ID 23; corresponds to complement of positions 364-388 of SEQ ID 10):

ACCCGGTCCGCCAGCGCGGCGCCGG second-round forward primer (SEQ ID 7; corresponds to positions 125-149 of SEQ ID 10):

GACCCACGGGAGGAACCATGACCGC second-round reverse primer (SEQ ID 24; corresponds to complement of positions 354-379 of SEQ ID 10):

GCCAGCGCGGCGCCGGCGGGACAGTC

For each of the four pool of recombinant-cosmid-containing clones (Example 3-e), cosmid DNA was prepared by use of the QIAfilter plasmid Midi Kit (QIAGEN, Inc.; procedures per instructions of the manufacturer), and an aliquot (1 μl; 0.1 μg/μl) was added to a first-round PCR reaction mixture (49 μl) containing 1 μl first-round forward primer (SEQ ID 4; 10 μM), 1 μl first-round reverse primer (SEQ ID 23; 10 μl), 1 μl 50×Advantage 2 Polymerase mix (Clontech, Inc.), 1 μl dNTP mix (10 mM each dNTP), 5 μl 10×PCR buffer, and 40 μl nuclease-free water, and first-round PCR was performed (7 cycles, each comprising denaturation for 25 s at 94° C. and annealing and extension for 3 min at 72° C.; followed by 32 cycles, each comprising denaturation for 25 s at 94° C. and annealing and extension for 3 min at 67° C.; followed by final extension for 7 min at 67° C.). The resulting first-round PCR product (1 μl of 1:50 dilution) was added to a second-round PCR reaction mixture (49 μl; components identical to those for first-round PCR, except for use of the second-round forward and reverse primers, SEQ ID 7 and SEQ ID 24), and second-round PCR was performed (5 cycles, each comprising denaturation for 25 s at 94° C. and annealing and extension for 3 min at 72° C.; followed by 20 cycles, each comprising denaturation for 25 at 94° C. and annealing and extension for 3 min at 67° C.; followed by final extension for 7 min at 67° C.). PCR products were analyzed by agarose gel electrophoresis (Sambrook, et al. (1989) *Molecular Cloning: A Laboratory Manual*, Cold Spring Harbor Press, Cold Spring Harbor N.Y.). For each pool of recombinant-cosmid-containing clones (Example 3-e), a PCR product with the expected size of approximately 257 bp was observed, indicating that each pool contains sia-III-locus nucleic acid sequences. The pool comprising the smallest number, ~500, of recombinant-cosmid-containing clones was selected for further analysis.

To screen individual recombinant-cosmid-containing clones for sia-I-locus nucleic acid sequences, dilutions of the selected pool of recombinant-cosmid-containing clones were plated to LB agar (Sambrook, et al. (1989) *Molecular Cloning: A Laboratory Manual*, Cold Spring Harbor Press, Cold Spring Harbor N.Y.) containing 50 μg/ml ampicillin and incubated 16 h at 37° C. to yield single colonies, single colonies ("clones") were picked and were cultured 16 h at 37° C. in LB containing 50 μg/ml ampicillin in wells of 96-well plates (2.2 ml square-cross-section wells; Mark II Storage Plates; ABgene, Inc.), and the resulting single-colony-derived cultures ("clones") were subjected to PCR probing. For each single-colony-derived culture, 0.5 μl was added to a first PCR reaction mixture (9.5 μl) in a well a 96-well plate (MicroAmp Plate; Applied Biosystems, Inc.) containing 0.25 μl forward primer (SEQ ID 4; 20 μM), 0.25 μl reverse primer (SEQ ID 23; 20 μM), 5 μl JumpStart REDTaq ReadyMix (Sigma, Inc.), and 4 μl nuclease-free water, and, in parallel, 0.5 μl was added to a second PCR reaction mixture analogous to the first but with forward primer SEQ ID 7 and reverse primer SEQ ID 24. PCR was performed (initial denaturation for 3 min at 94° C.; followed by 30 cycles, each comprising denaturation for 30 s at 94° C., annealing for 30 s at 55° C., and extension for 1 min at 72° C.; followed by final extension for 10 min at 72° C.), and products were analyzed by agarose gel electrophoresis (Sambrook, et al. (1989) *Molecular Cloning: A Laboratory Manual*, Cold Spring Harbor Press, Cold Spring Harbor N.Y.). In total, 576 clones, comprising six 96-well plates of clones, were analyzed. Four clones yielded first PCR products of 306 bp and yielded second PCR products of 257 bp, indicating that the four clones contain sia-III-locus nucleic acid sequences. For each of these four clones, cosmid DNA was prepared by use of the QIAfilter plasmid Midi Kit (QIAGEN, Inc.; procedures per instructions of the manufacturer).

Example 3-c

Characterization of Nucleic Acid Sequences Encoding Precursor, Processing Factors, and Transport Factors for Siamycin III: Sequence Analysis For each of the four positive clones from Example 3-b, cosmid DNA was subjected to dideoxy nucleotide sequencing. A primer-walking strategy was employed, involving successive iterations of primer design and sequencing. In the first iteration, primers were designed based on the sequence defined by genome walking (SEQ ID 10; Example 1-e); in each subsequent iteration, primers were designed based on sequence determined in the previous iteration. The 10,500 bp sequence obtained in this manner is as follows (SEQ ID 25):

CCCCTCCGGCGGACGGAAAGCGCTGCTCGTAGCCGGTACGGCCACCTCCG

GAGGCGAGGGTTCCGCCCCGCCTCCGGGGGCGGTACGAAGCACCCCCGGA

AACTGTGTAGACTTACCGACGTCGCTGATCGCACCATGGTGCACACGGCG

CGCCGCCTTAGCTCAGATGGCCAGAGCAACGCACTCGTAATGCGTAGGTC

TCGGGTTCGAATCCCGAAGGCGGCTCTTCTTCAAGCCCCGCGCAGACAGT

GTCTGAGCGGGGCTTTCTCGTTCCGGTGCTGCTCACGCCCCGTTCCGGAC

CAGTTCCCCGGCGGGCTCGCCGAAGCCCGCGTCCCGGGCCATCACCACCG

CCGTCGCCCGGTCGTGCACCTCGAGCTTGGCGAAGATGCGCGAGACGTAG

TTGCGGACGGTCTTCTCGGCCAGGAAGAGCCGGCGGGCGATCTGCCGGTT

CCCCATCCCGCCGGCCAGGAGCTCCAGTATCTCCAGCTCGCGGCTGGTGA

GCCCCGGGAACCCGGCGCCGTCGTGCAGGCCCTGCATGGCGGAGAAGTAG

CGGCTCATGCGGGCCGCGACGCTGGGGCAGAAGGCGGCGCCGCCCCGGGC

GACGACCTTCAGGGAGCGGAGCAGTTCGTCGGCCGAACCGAGGCGGGAGA

GGTAGCCGTTGACACCCGCGCGGAGGGCCGAGACGATCATCTCGTCGTCG

TCGTTCTGCGCCACCACGATCGTGTGCGGCCGGGACGCCTCGTCGGGGAA

GGCGGAGGCGATGTGCCGGACGCGTGCGGAGACGGTTCTGCTGGAGGACG

GTTCGCTGAGGACGACCACGTCGGGGTGGAGGGCGGTGCCGGCCAGGTCC

GACAGACGTCGGAGGTCGTCCGAGTCGTCCGTGGCACGGCCGACAAGAGC

-continued

```
GCACTCCTCATCCTGATCGACAATCGCTTCGAGCCCGGCGAGGGACACCG
CGTTGTCGCTGACCACGAACAGGTTGACGGTCATCTCGTACATCCCCCAG
AAATGCGTCGACGTGGTGCGGACGGCGCCGGAAGGTCCCCGGGGGCACAC
GCGACGAAGGGTCGGTCCGTAGGCGACCGACTCCGGGCGTGACGTGGTCA
GTTGTGGTTTTCAGCGGCCCCCGTGGCCATGACCTGTCGGCGCAGGCATG
GTGGTGCATCGAAAGCGCGCAAGGCGCTCGTGGTGCCGAGTATGTGGACG
CGTCCGGAGAGAACGCAAGGTCGCCAACGCACCCGTGTTGTCCGAGGGGT
GAGTATCGGCCGGACCCCGCCGAACCACCGCGATTCCGGCGTCGGAGGTG
GTGGGGGCGGCTCCGGGCGCGCGACCCGCAGGACCGCGCGCCGGTGTGGG
CCGTGGTGCGGGGCGGACGACACTGTCCGAAACGGTCACCGCCCGGCGCG
ACACGCGGACGTCCGGCCCTGCGCCCGTTGGACGGGCCGCGGAGCGAGCG
CTTACGTTCGACGGCATGGGTGAGGGGTCCCGGAGGCGTGCGATCGTGCT
GGACGCGGCGGCGGCCTGCGCGTTCACGCTCCTGCCGCAGGTGTCGCTGC
TGCGGCCGGCCGTCGACGCGGGACGGGCGGCGGCCTCCTGTGGCTGCTG
TCCCTGGCCGCCGGACTCCCGCTCGCCGTAAGGCGGTTGTGGCCCGTCCC
GGTCTTCGTCCTCGTCCTGGCCGCCGCCTGCGGGCGCTGGCCGCCGGCC
TCGGACCCGCCTCGTTCCTGGCCGCCGCCTACGCCGTCCACACGGTGGCC
ACCACCCGGCGGCGCGACCCCGGGGTGTCGGCCGTCGCCGTCGCCGGGCT
GTGCGCGGCGGTCGCCGCCCTCCTCACGCGTGTCGGGCGGGCAGTCCTACC
AGGGTGGCAGCACCGCCGTGCAGGCCGTGTTCGGCCTCCTCGTGCTCGGC
GCGACCTGGGCGGCCGGCTCGGCGGTCAGGGAGCGCAGACGCAGTACCCG
GCGCGCCATCGAGCACGCCGCCGAGCAGGCGAAGACCGAGGAGCGCCTGC
GCATCGCCCGCGACATCCACGACGTCGTCACCCACAGCGTGGGACTCATC
GCCGTCAAGGCCGGCATCGCCAACCACGTGGTGGCCACCCGCCCCGAGGA
GGCCAAGGAGGCCCTGGCGGTCATTGAGGACGTCAGCCGCCGGGCGCTGC
GCGACATGCGCGCCACCCTGACCGTGCTGCGCGGTGAGGACCGGAGCGAG
GCCGGGGACCTGCGGCCCGCCCGCGGCCTCGCGGACCTGCCCGCGCTGCT
CGAGACCGCCGAGGCGGCAGGCGTCCGCGTCGAACTGCGCACCCGCTACG
ACCAGGAACCGCCCGAGGGTGTCGCGCTGGCGGCGTTCCGCATCGTCCAG
GAGTCCCTCACCAACGTGCTCAAGCACGCCGCGCCGACCGGCTGCCGGGT
GGACGTCACGGCGCGGCAGGGCGTGCTGACGGTGGACGTGACCGACGACG
GCCCCGGCCCCGGACGCCGGACCACGGTGCCCGGCGGCGGGATGGGGCTG
GTCGGCATGAAGGAGCGGGCCGCCGCGCACGCGGCACCCTCGCCGCCGG
CCCCCGGCCCGGCGGCGGCTTCCGGGTGACGGCCACCCTGCCGTTCTAGG
ACCTGACGGACGCCGGCTCATCCTCGGGTATGAGGGGCGCCCGCGCGGCA
CCGCGCCGGGTTCCCGACCGCGGGCCGATGCGGTCGCGGGGTGTGCGCCG
CGAGACTCGACACGTGATGCTTGCCGAGAGACTGACCAAGCGGTACGGGC
CCGCCACCGTCGTCGACGACCTGTCCTTCACGGTGCGACCAGGTGTCGTC
ACCGGCTTCCTCGGGCCCAACGGCGCCGGGAAGTCCACGACGATGCGGAT
GATGCTCGGCCTGACCCGCCCCGACGCGGCACGGCCACCGTCGGCGGAC
GCGCCTACCGCGACCTGACCTACCCGCTCCGGCACGTCGGCGCGCTCCTG
```

-continued

```
GAGACGTCGGCCCCGCACCGTGGCATGACCGCCGTCGGCCATCTGTCGTG
GCTGGCGCGCAGCAACCGCGTTCCCCGCCGGCGGGTGGACGAGGTGCTCG
ACGCGGTCGGTCTCACGGAAGCCGCCCGTAAACGGGTCGGCACCTTCTCC
CTGGGCATGGGACAGCGCCTCGGCCTGGCGGCTGCCCTCCTCGGCGACCC
CCCGGTCCTGGTGCTCGACGAGCCGGTCAACGGGCTCGACGCCGAGGGCA
TCCGGTGGCTGCGCGAACTGCTGCGCGCCAAGGCAGCCGAGGGCCGCACC
ATCCTCGTCTCCAGCCATCTGATGGCGGAGATGGCGCAGGTCGCCGACGA
GCTGATCGTGATCAGCCGGGGCCGGCTCCTCGCCGAGACCAGCGTGTCGG
AGTTCCTCGGACGCCACGGCCGGACGTTCGTACGGGTCCGGACCTCCGAA
CCGCTGCGGGCCGCGCAGGAGTTCCAGGCGAAGGGCGCCACCTCGGTGCG
GCGGGCCGCGGACGGCGGCCTGGAGGTGGACGGCCTGCCGGCGGGCGAGG
TGAACCGCATCGCCGCGGCGGCCGGTGTCCCCGTCGAGGAACTGAGCACC
CACACCGGCTCGCTGGAGGAGACCTTCCTCAAGCTCGTCGACGACGGAGG
AGATCCCACGCATGTCTGAGACCCTCGCGGCCGCGCGGGCGGAGTTCACC
AAGATGCGGGCGGTGCGCGCCACGTCCGTCGCACTGCTGCTGTTCGTCGC
CGTCAGCGTGTTCATCGCCGCACTGGGCGGCTGGTCCGCCAAGGGCGCGA
TCGAGTCCGGCAATCCCGGGCTGCGCTCCGACTTCACGCCCGAGCAGGCC
GGCCTGGACGGCATCCTCTACGCCAGCTCGCCCTGATCGTGTTCGGGGT
GCTGATGATGTCCGGCGAGTACACCTCGGGCATGATGCGGGTCTCGCTGC
TCGCGGTGCCCCGGCGGGGCCGGCTCTACCTGGCCAAGACGGCCGTCACC
GCCGTCGCGGCCCTGGCCGTCGCCCTTCCGGTCACGGTCGTGTCGTACCT
GGTCAGCCAACTCGCCCTGGGCCCCCACGGGTCGACGCTCGACGCGGACG
GCGTCCCGCGCCCTGGCCGGCGCGGTCGTCTACCTGACCCTCATGAGC
CTGCTCGCCGTAGGGGTGGCGGCCGCCGCCCGCAGTGCCGTCCTCCCGCT
GGCCGTGCTGCTGCCGCTGGTGCTGGTCGGCTCGCAGATCCTGTCCGTCA
TCGGGGCGACCAAGGAGGTGGCGCGCTGGTTCCCCGACCGGGCCGGCGCC
CAGATGCTCACCGTCGACTCCGGCGACGCCCTCACCGGCCTCGTCGTGCT
GCTCGCGTGGACCGCGGCCGCCCTGACGGCCGGCTGGCTCCGGCACCGTT
CGTGGGACGGGTGACGGGACGCGCCTGAGGCATGTGCCCCATGCGCGTGG
GACATGGCCCCTCGTAGGTTCCCGGACAGGTCACGGGGCCGAAAAGGTCG
GCCCGGGCCGTTCGACCCACGGGAGGAACCATGACCGCGATCTACGAGCC
GCCCGCCCTGCAGGAGATCGGCGACTTCGACGAGCTCACCAAGTGCCTCG
GCATCGGGAGCTGCAACGACTTCGCCGGCTGCGGTTACGCCGTCGTCTGC
TTCTGGTGATCGCACCGGTGCCGGTGTGCCCCTCGTGGGCACACCGGCAC
CGCCCCGGGGAGTGAGGCGACATGGAATTCACAGTGCTTCCGGACTGTCC
CGCCGGCGCCGCGCTGGCGGACCGGGTGGCGGCACCGAAGCGGATCGACC
ACGCGTCGGGACGCCCTGGATCGTGGGGACTGGCCCGAGGGCGGGACG
ACGGTGACCGAGGCCGGCACCCGCCGCCTGGCGGTGTTCGGACACACCCG
GCCCGACGACGCGGGAACGGCCTCCGCGCTCGGCCGGATGCGCTCGCTGC
ACGACGTCGACCGGGTCGCGTCCCGGCTGCCCGGGGTCTTCCACCTCGCG
```

-continued
```
GCCTCCCTGGACGGCGCGGTCCGCCTCCAGGGCTCCGTGGCCGGCGTACG
GCAGGTCTTCACCGCCCGGGTCGACGGGGTGACGGTCGCCGCGAGCGCCG
TGGACCCGCTGCTGCGCCTCACCGGCGCGGGACTCGACGAGACCCTGCTG
GCCGCGCGGCTGCTGGCGCCCGGCGGGGCGCCCTGGCCGCTCTCGCCGCG
CCCGGTCCGCCGCGGCGTGGACGCGCTGCCCACCGGCCACTGGCTGGAGC
TCGGCGCCGACGGCCGGGCCCGCAGCGTCCGTTGGTGGGAACTGCCCGAG
GCGACCCTCTCGCTGGAGGAGGGTGCCGGGGCCGTCCGTTCCGCGCTCAC
CGACGCCCTCGCGACCCGTGTGGACCCGCACCGCACGGTCAGCGCGGACC
TCTCCGGCGGACTCGACTCGACCACCCTGTGCTTCCTCGCCGACGCGGCC
GGCGCCGACCTGGTCACCTACCACGTCATGCCGCTCGACGAGGCCAACGA
GGACACCGCATGGGCCCGCAAGGCCGCCGCGCATCTGCCGCACGCCCGCC
ACCACATGCTCGCCGCGGACCGCGCCGCCAACCTGTTCGACATCGGCTAC
ACCGCCGACACCCTCAACGCGGCCCCCGAGGGCCCCTCGACGTGGGCCTC
CGGACTCGCGCACATCCGGGACCTCGCCGGGCGGGCCACCGCCGAGGGGG
CGGCCCTGCACCTGTCCGGGTTCGGCGGGGACGAACTCTTCGGCCGGATG
CCCGCCTGCGCCTGGTCCCTCGCCCGCCTCCGCCCGGCCGACGGCCTGCG
GCTGGTGAACCGCTACCGGCTGGCCAACCGCTGGCCCTGGCGCAGCACCC
TGCGGCAGCTCGCGGACCGTTCGACGTTCGCGCAGAACCTGACCGAGGTC
GCCGGGCGGATCACCGCCCCGCCCCCGCCGGTCAACGAGCCGGACTTCGG
CTGGGTGTTCGCGCCGCGCATGCCCGCCTGGGCCACCCCGGACGCGGTGG
CCGCCGTGCGGGACCTGCTGACCACGGCAGCCGAACGGACCCCGGAACCG
CTGGACGCCGACCGGGCCCGGCACCAGGCGCTGTCCTCCATCGTGTTCGA
GGGGAACACCGTCCGGCAGGTCAACACCGCCGTCGCCGGCACCGGCCTGG
TCTGGGAGGCGCCGTTCCTCGACGACCGGGTTCTCGAGGCGGCCTTCGCC
ACCCGGATCGACGAGCGGCTGGCCGCCGGACGGTTCAAGCCGCTGCTGAC
CACCGCCGTGCGGGGCCTCGTGCCCGACGACTTCCTCGCCCGTCGCGACA
AGGGAGAGTTCAGCGCCGAGACGTTCCGGGGCATCGAACGCAACCGGGAC
CGGATCCTGGACCTCTGCGAGGACTCGCTCCTGGCCCGGCTCGGCCTCGT
CGACCCGCACGCCTTCCGGTCCGCGGTGCTCAACCCCGGGCCGATGTCCC
ATCACCTCCAGCCGATCCAGACCACGGTGGCGTGCGAGAGCTGGCTGCGG
GCGCACCCCAGGACACCGGAGAGAACCGATGAAACTGAGTCTTGCCCGC
GACGTCACCCTCACGCCCGTCGATTCCGGGGCGGTCCTGCTCGACGGCCG
CCGCGGACGCTACTACCAGCTGAACGCCTCCGGCTCCGCGATCCTGCACA
AGCTGCTCGACGGCGACACTCCCGCCGCGGCCGCCGCGAGCCTGTCGGAG
TCCGCCCCCGTCAGCGAGGAGCGGGTGCACCAGGACGTGCTGGCCCTGGT
CCGCTCGCTGAGCGAGGCCGACCTCGTGGAGGTGACACAGTGACCACGCC
CGCCGTCGCCGAACAGGCCACGCGCCTCCCGCTGCACCGGCAGATCGCCC
CCAGATGCGCGCCGGCGCCGCCCGTCTGCTGGTCAGGCTGCCCCCGGCC
CGGCTGCACCGGGTGCTGCGCGTCCTGAGCAAGGGTTCCCGGCCCGCCGG
ATACGCCCAGGTGGCGCGGGCCCGGCGGTCCGTCGTCTCGGTCAGCACCC
GCTGCGCGGGCCTCGGCTGCCTCCAGCGGTCCGTCGCCACCGTGCTGCTG
CTCCGCGTCCGGGGCAGGTGGGCCGACTGGTGCACCGGCTTCCGGGTGCA
GCCCTTCGCCGCGCACGCCTGGGTCGAGGCCGGCGGCCGCCCGGTCGACG
AGCCCGGAGAGGTCGGCGTGTTCCGCACCGTGCTGGCCGTGCGCCGCACC
GGAGGCGGCTCATGACGGCGATCCGGGCCGAGGGCCTCTACGCGTACTAC
GGCACCACGCCGGCCGTGAACGGCCTCCACCTGAACGTCCCCGAGGGGGC
CACCTTCGGGTTCCTGGGGCCGAACGGCGCCGGCAAGACCACCACCATCA
GCATGCTCACCACGCTGCTCAGGCCCACGGCGGGCCGCGCGGAGGTGGCC
GGGTTCGACGTCACCACGCACGCCGCCGAGGTGCGGCGCAGGATCGGCAT
CGTCTTCCAGGAGTCGACGCTCGACCTGGAACTCACGGCGACCGAGAACC
TGCGATTCCAGGCCGACCTGTGCGGTCTGGGCCGGGCCGAGGCGCGCGCC
GCGGTGGCCGCGATGCTCGACATGATGGAGCTGACGGGACGCGACAGGAC
CCCCGTGCGGCACTTCTCCACCGGCCTGCGCCGACGCCTGGAGATCGCCC
GCGGCCTGCTCGGCTCCCCGCGCGTGCTCTTCCTCGACGAGCCGACCACC
GGCCTCGACACGCAGACCCGTGCGGCCGTCTGGCACCACCTGGACCGGCT
CCGCGAGGAGCAGGGCATCACGGTCTTCTTCACCACGCACCAGCTGGAGG
AGGCCGAGCACTGCGACCGCATCGCGATCTTCGACCGCGGCAAGCTGGTC
ACGGAGGGCTCACCCGCGGAGCTGAAGTCCGTCATCGGGGCCGACGTCGT
CGACCTGCGCACCGATGACGACCGGCTGGCCGTGGACCTGCTGTCCGACC
GCTTCGGCCTGACGGCCGAGAACACCCCCGGCGGACTGCGGCTGAGGGTG
CAGGACGGCGCCTCCATGGTGCCCCGCCTGTGCACCGGGCTGGGCCTGGG
CGTGCGGTCGGTGACCGTCACCCCGCCCTCGCTCGACGACGTCTACCTGC
ACCACACCGGGACCGCGATCAGGGACAGCGGGTCCGACGCCCGCTCGCTC
GACAGCCTCGGGGAGGGACTGCGATGACCCGGACCGACATCCCGCCGAGC
GTCACCGTGACGAAACCGGCCCCGCCCTCGTCCGAGGGGCGGACCTGGCA
CACCGTACGGCCCTACGCGCTGCTGTGGCGGCGTGAGATGACCCGGCTGC
GGCACAATCCGCTGCGCCTCGTCATGGGTCTGGTCACCCCGCTGCTGTTC
CTCGTCGTGCTGGGCACGGGGCTGGAAGCGGCGTCGTCCACGCTCGGCAA
GGCCCAGCTAAACGACTACCGGGCCTACCTGTTCCCGGGCGCGCTCGTGA
TGTCCGTGCAGGCCCCGGCCATCGCCGTGGGCATCTCGCTCGTCTGGGAC
CGCCGGCTCGGCATGCTGCGCCAGATGCTCGTCTCCCCGTTCCCTCGGTC
GAGCATCGTCCTCGGCCTCGCGCTCGGCGGAGCCACCACGGGCGCCGTCT
ACGGCCTCGCCCTGCTCGCGGTCGGAGGCATCGCGGGCGTCCGGTACACG
CCGATGCTGCTGGTCGTCCTCGTCGAACTGCTCCTGGTCTCCCTGCTCTT
CACCTCGTTCGGCCTTCTCGCCGCGGTCACCATCCGGCAGGTCGACACCT
TCCAGATCGTGGTGAACCTCAGCCTCATGCCGCTGATGTTCTTCTCCGGC
GCGATGTTCCCGCCCAACGGGCTGCCGGGCTGGCTCGACACCGTCGTCAA
GCTGAACCCGCTGACCTACGCGTCGACGCCGTGCGCCGGACACTGCCCG
GCCCCGACGTCCTCACCTCGGAGCAGACCCGGCTGATGCTCGGCGACTGG
AACCCGCCCGTGTACGCGGAACTCGGCGTGCTGGCCGCCCTCACCGCCGC
CGTACTGGGCCTCGCCACCTACCGGTTCTCCCGGGCGCAGTGAAAGGGGG
```

-continued
```
CCGGCCGTGACGTTCGTGCGGACATGGGCGGGCACCGCGGCCAGGATCGT
CCTCGCGGCGGTCCTGGGCTACGCGGGCTGGGTGAAGGTCCAGGACCTCA
CGGGAGCCGGCCGTACCGTCGCCCTCTACCAGCTCGTCCCCGAGGAAAGC
GCACAACTCGTCGGCGCCGCCGTGGCGTTCGTCGAACTGGCGCTTGCCCT
GCTGCTTCTCGCCGGGCTCGCCACCCGCGCCGTGGCGGCCGTCACCGCCC
TGCTGATGGTCACGTACATCGCGGCCATCGCCTCGGTGTGGGCGCGCGGG
ATGTCCATCGACTGCGGCTGCTTCAGCAGCGGCGGCACCCTCACCGGCGG
CGCGGAACGGGGCTACGTCGTCGACATCGCGCGCGACCTCGCCTTCCTCG
GCGCCGCCGCGTTCCTGATCACCCGCCCGCGGACCCGTTACGCCCTGGAC
CGCTGGGTCCTGGAAACGAAGGAGCGATAGACATGCAGCCGTCGACGGAC
GCCCAGGTCCGGGAAATGGTCCACCGGCGCCGGCGACGCCGCCGCACTGT
GCTGGTGTCGCTCGCGGCGGTGGTCACGGTGCTCGGCGCCGCGCTCGTCG
GCGCCGGCCTGGTCCGGGCCACCGACACCGAGCCCGGCGATGCGCCCGAG
GAGGTGCCCGCCGGTGTGGCCGCCGACCGGGCCGGACTCGTCACGTCCGA
GGGTCCGGTCCGTGTCGACCTCTACCTCGACTACCTCTGCCCCGAGTGCC
GCATCACCGAGAAGGCCCTCGCGCCCGAACTGAGGGAGATGCAGGAACGC
GGAGAGGTGCGCGTCGTCCACCACCCGGTCGCCTTCCTCGACGACCGCAG
CGCCCCCGCCGGCTACTCCACCCGGGCCGCGTCCGCCGCCGCCTGCGCCG
CTGACCGGAACAAGTTCGAGCCCTACACGGCGGCGCTCTTCGACGAGCAG
CCGCCGGAGCAGGGCCCCGGCCTCGACACCGACCGCCTGGTCGCCCTCGG
CCGGGACGTCGGCATCACCGGCGCGTCCTTCGAGCGGTGCGTCCGCGACG
GCACGTACCGGCCCTGGGTGACGTACGTGTCCGAGGTCGCCGCCTCCCGC
GGGGTGGCCCTCACCCCGACCGTGAAGGTGGCCGGCAAGCGCGTGGACCT
CTCCGGACCCGACCGGGCGAAGGCGTTCGTGCGAGCGGTGGAGGAGAGCC
GTTCATGAGCCGCCTCACCGTGGCGCTGACCGGGGACTGCATGATGACGC
GGGGCGCGCCCGTCACCTCCGACCCCGCCGCCGGCCGACTGGGCGAGGTG
CTGCACACGGCCGACTTCGCCTTCACCAACCTGGAGGTCGCGCCCGCCAC
CGGACGCGGCCACCCCGTACCCGACGCGGCCAGCGGAGGCGGCCTGATCG
CGGACCCCGCCGTCCTCGACGACGTGACGGGGATGGGCTTCTCCGCCCTG
AGCTGCGCCAACAACCATGCCCTCGACCTGGGCACGGAGGGCGTCCTCGG
```

The 10,500 bp sequence contains two presumptive operons.

The first presumptive operon comprises eight tandem ORFs: (i) an ORF encoding the precursor to siamycin III (see Example 1-b); (ii) an ORF encoding a protein that exhibits similarity to amidotransferases, the class of proteins that includes MccJ25 processing factor McjC; (iii) an ORF encoding a protein that exhibits similarity to oxidoreductase-cofactor-synthesis factors involved in disulfide-bond-formation reactions; (iv) an ORF encoding a protein that exhibits similarity to transglutaminases, the class of proteins that includes MccJ25 processing factor McjB; (v) an ORF encoding a protein that exhibits similarity to ABC-transporter ATP-binding subunits, the class of proteins that includes MccJ25 export factor McjD; (vi) an ORF encoding a protein that exhibits similarity to ABC-transporter integral-membrane-protein subunits; (vii) an ORF encoding a protein that exhibits similarity to integral-membrane oxidoreductases involved in disulfide-bond-formation reactions; and (viii) an ORF encoding a protein that exhibits similarity to extracytoplasmic oxidoreductases involved in disulfide-bond-formation reactions. Based on the fact that the presumptive operon encodes counterparts of the precursor, the processing factors, and the export factor for biosynthesis of lariat-peptide MccJ25 (see Solbiati, et al. (1999) *J. Bacteriol.* 181, 2659-2662) and, also, encodes counterparts of a oxidoreductase-cofactor-synthesis factor, an integral-membrane oxidoreductase, and an extracytoplasmic oxidoreductase—which are expected to be required for efficient, accurate disulfide-bond-formation by a Gram-positive bacterium such as the producer strain *Streptomyces griseoflavus* Tü 4072 (see Kadokura, et al. (2003) *Annu. Rev. Biochem.* 72:111-135)—we infer that the operon comprises genes for the precursor, the processing factors, and the export factors for biosynthesis of the multiple-disulfide-bond-containing lariat peptide siamycin III. We designate this presumptive operon as the sia-III operon. The sia-III operon is preceded by a presumptive promoter, having a sequence that conforms to the consensus sequence for a promoter recognized by the major σ factor of *Streptomyces* sp., HrdB (Bourn, et al. (1995) *Nucl. Acid Res.* 23, 3696-703), and having a location and a sequence that correspond to the location and sequence of the sia-I promoter, siaP-I, identified by use of primer extension (Example 2-c). We designate this presumptive promoter as the sia-III promoter, siaP-III.

The second presumptive operon comprises five tandem ORFs: (i) a first ORF encoding a protein that exhibits no significant similarity to known proteins; (ii) a second ORF encoding a protein that exhibits no significant similarity to known proteins; (iii) an ORF encoding a protein that exhibits similarity to two-component-regulatory-system sensor kinases; (iv) a first ORF encoding a protein that exhibits similarity to peptide-specific ABC-transporter proteins; and (v) a second ORF encoding a protein that exhibits similarity to peptide-specific ABC-transporter proteins. We consider it unlikely that this presumptive operon is involved in, or related to, biosynthesis of siamycin III. However, we cannot exclude the possibility that this presumptive operon is involved in, or related to, biosynthesis of siamycin III (for example, through effects on regulation of the sia-III operon or though effects on export of siamycin III). We designate this presumptive operon as the xia-III operon.

Promoter and ORF sequence coordinates are as follows:

siaP-III, 4391-4420 (core promoter elements); 4428 (transcription start)
siaA-III, 4481-4609 (SEQ ID 26)
siaB-III, 4672-6483 (SEQ ID 27)
siaC-III, 6480-6743 (SEQ ID 28)
siaD III, 6740-7165 (SEQ ID 29)
siaE-III, 7162-8172 (SEQ ID 30)
siaF-III, 8124-8993 (SEQ ID 31)
siaG-III, 9007-9480 (SEQ ID 32)
siaH-III, 9483-10208 (SEQ ID 33)
xiaA-III, 136-1092
xiaB-III, 1129-1473
xiaC-III, 1466-2599
xiaD-III, 2630-3619
xiaE-III, 3612-4364

ORF properties are summarized in Table 2:

TABLE 2 sia-III/xia-III sequence features.

| ORF Name | ORF Coordinates | Frame | Length (codons) | ORF Inferred Function | ORF Family | ORF Similarity to mcj ORFs (encoded amino-acid sequence identity) |
|---|---|---|---|---|---|---|
| siaA-III | 4481-4609 | +2 | 43 | siamycin III precursor gene | | |
| siaB-III | 4672-6483 | +1 | 604 | siamycin III processing-factor gene | amidotransferase genes (asparagine-synthetase-glutamine-hydrolyzing genes) | |
| siaC-III | 6480-6743 | +3 | 88 | siamycin III processing-factor gene | oxidoreductase cofactor-synthesis genes (pqqD-family genes) | |
| siaD-III | 6740-7165 | +2 | 142 (GTG start) | siamycin III processing-factor gene | transglutaminase genes | mcjB (40% for codons 77-121) |
| siaE-III | 7162-8127 | +1 | 322 | siamycin III transport-factor gene | ABC-transporter ATP-binding-subunit genes | mcjD (18% for codons 10-216) |
| siaF-III | 8124-8993 | +3 | 290 | siamycin III transport-factor gene | ABC-transporter integral-membrane-subunit genes | |
| siaG-III | 9007-9480 | +1 | 158 (GTG start) | siamycin III processing-factor gene | integral-membrane-oxidoreductase genes (doxD-family genes) | |
| siaH-III | 9483-10208 | +3 | 242 | siamycin III processing-factor gene | extracytoplasmic-oxidoreductase genes (dsbA-family genes) | |
| xiaA-III | 136-1092 | +1 | 319 | | | |
| xiaB-III | 1129-1473 | +1 | 115 | | | |
| xiaC-III | 1466-2599 | +2 | 378 | | two-component sensor-kinase genes | |
| xiaD-III | 2630-3619 | +2 | 330 | | peptide-specific ABC-transporter ATP-binding-subunit genes | |
| xiaE-III | 3612-4364 | +3 | 251 | | peptide-specific ABC-transporter integral-membrane-subunit genes | |

Example 4

Isolation and Characterization of Nucleic Acid Sequences Encoding Precursor, Processing Factors, and Transport Factors for Non-MccJ25-Related Lariat Peptide Siamycin I

Example 4-a

Isolation of Nucleic Acid Sequences Encoding Precursor, Processing Factors, and Transport Factors for Siamycin I: Preparation of Producer-Strain Genomic DNA Library A producer-strain genomic DNA library was constructed by use of the pWEB-TNC cosmid cloning kit (Epicentre, inc.; procedures per instruction of the manufacturer with minor modifications). *Streptomyces* sp. strain SKH-2344 genomic DNA (20 μg in four aliquots of 5 μg each; prepared as in Example 2-b) was digested with restriction endonuclease HaeIII under conditions that yield partial digestion and result in genomic DNA fragments with a mean size ~35,000 to ~45,000 bp. Four aliquots of genomic DNA (5 μg each) were incubated, in parallel, with 0.01 U, 0.02 U, 0.05 U, and 0.1 U HaeIII in 100 μl 1×HaeIII buffer for 1 h at 37° C. The reaction mixtures were combined, and the reaction products were extracted with 400 μl phenol-chloroform (1:1, vol/vol), ethanol precipitated, and re-dissolved in 52 μl TE. The resulting genomic DNA fragments (52 μl) were added to an end-repair reaction mixture (80 μl) containing 4 μl end-repair enzyme mix (contains T4 DNA polymerase and T4 polynucleotide kinase; provided with the kit), 8 μl) 2.5 mM dNTP mix, 8 μl 10 mM ATP, 8 μl 10× end-repair buffer, and the reaction was allowed to proceed for 45 min at 25° C. The resulting end-repaired genomic DNA fragments were size-selected by gel electrophoresis on 1% low-melting-point agarose (Invitrogen, Inc.); excision of a 2-4 mm gel segment corresponding to a DNA fragment size of ~35,000 bp to ~45,000 bp (sizes inferred based on ethidium-bromide-stained T7 DNA markers); addition of 3 μlGELase (1 U/μl; provided with the kit) and 20 μl 50× GELase buffer and incubation 30 min at 45° C. followed by incubation 10 min at 70° C.; addition of 1 ml 5 M ammonium acetate and removal of insoluble material by centrifugation; precipitation with two volumes 100% ethanol; and re-suspension in 40 μl TE (10 mM Tris-HCl, pH8.0, 0.1 mM EDTA). The resulting size-selected end-repaired genomic DNA fragments (0.3 μg in 5 μl) were added to a ligation reaction mixture (15 μl) containing 1 μl 0.5 μg/μl pWEB-TNC, 1 μl 1 U/μl Fast-Link DNA ligase, 1 μl 10 mM ATP, 2 μl 10× fast-link ligation buffer, and 10 μl nuclease-free water; the reaction was allowed to proceed for 2 h at 22° C.; and the reaction was terminated by heat-inactivation of DNA ligase by incubation 10 min at 70° C. 10 μl of resulting recombinant DNA (0.4 μg) was added to an in-vitro-packaging reaction containing 25 μl in-vitro-packaging extract (provided with the kit), the reaction was allowed to proceed 90 min at 30° C., a further 25 μl in-vitro-packaging extract (provided with the kit) was added, the reaction was allowed to proceed a further 90 min at 30° C., and the reaction was terminated by addition of 500 μl phage dilution buffer (10 mM Tris-HCl, pH 8.3; 100 mM NaCl, and 10 mM $MgCl_2$) and 25 μl chloroform and transfer to 4° C. 500 μl of resulting recombinant phage stock (2×10$^4$CFU/ml; titer determined per instructions provided with the kit) was mixed with 5 ml *Escherichia coli* strain EPI100T1$^R$ [Δ(mrr-hsdRMS-msrBC) mcrA lacX74 recA1 Φ80dlacZΔ M15; provided with the kit] and incubated 20 min at 37° C.; dilutions yielding 200-300 recombinant-cosmid-containing clones were plated on LB-agar (Sambrook, et al. (1989) *Molecular Cloning: A Laboratory Manual*, Cold Spring Harbor Press, Cold Spring Harbor N.Y.) containing 30 μg/ml ampicillin, and plates were incubated 18 h at 37° C. The resulting recombinant-cosmid-containing clones (3000-5000 clones) were scraped from plates, suspended in 15 ml LB containing 20% glycerol, and were stored in 3 ml aliquots at −70° C.

Example 4-b

Isolation of Nucleic Acid Sequences Encoding Precursor, Processing Factors, and Transport Factors for Siamycin I: Screening of Producer-Strain Gnomic DNA Library To screen the producer-strain genomic DNA library (Example 4-a) for clones containing sia-I-locus nucleic acid sequences, colony hybridization and colony PCR were was performed.

For colony hybridization, a hybridization probe >400 nt in length was employed, in order to maximize the sensitivity of hybridization. A $^{32}$P-labelled hybridization probe 450 nt in length was prepared by use of a PCR reaction, using producer-strain genomic DNA as template, followed by a radioactive asymmetric PCR reaction (see Sturlz, et al. (1990) *Anal Biochem.* 185, 164-169). Primers were designed based on ski-I sequences defined in Example 2-b (SEQ ID 20) forward primer (SEQ ID 34; corresponds to positions 8-35 of SEQ ID 20)

CGACCAGGCGGGAAACGAACTGCTCACC reverse primer (SEQ ID 35; corresponds to complement of positions 449-477 of SEQ ID 20)

TCCGGAAGAACCACGAATTCCATGTCGCC asymmetric-PCR reverse primer (SEQ ID 37; corresponds to complement of positions 431-459 of SEQ ID 20)

TCCATGTCGCCTCGTTCCCCGTCTCCTCG

Genomic DNA (0.1-0.2 μg; prepared as in Example 2-b) was used as template in a PCR reaction (25 μl) containing 0.2 μM forward primer (SEQ ID 34), 0.2 μM reverse primer (SEQ ID 35), 0.2 mM each dNTP, 0.5 μl 50× Advantage 2 Polymerase Mix (Clontech, Inc.) and 1× Advantage 2 PCR buffer (initial denaturation for 1 min at 94° C.; followed by 7 cycles, each comprising denaturation for 30 s at 94° C. and annealing and extension for 1 min at 72° C.; followed by 30 cycles, each comprising denaturation for 30 s at 94° C. and annealing and extension for 1 min at 68° C.; followed by final extension for 4 min at 68° C.). Products were analyzed by agarose gel electrophoresis (Sambrook, et al. (1989) *Molecular Cloning: A Laboratory Manual*, Cold Spring Harbor Press, Cold Spring Harbor N.Y.). A product of 470 bp was observed, and was eluted and purified by use of the QIAquick Gel Extraction Kit (QIAGEN, Inc.). The product (~20 ng) was used as template for a radioactive asymmetric PCR reaction (50 μl) containing 1 μM asymmetric-PCR reverse primer (SEQ ID 37), 5 μM each dNTP, 0.4 μM [α-P$^{32}$] CTP (6000 Ci/mmol), 1 μl 50× Advantage 2 Polymerase Mix (Clontech, Inc.), and 1× Advantage 2 PCR buffer (initial denaturation for 1 min at 94° C.; followed by 10 cycles, each comprising denaturation for 30 s at 94° C. and annealing and extension for 80 s at 70° C.; followed by final extension for 4 min at 70° C.).

Colony hybridization was performed on positively charged nylon membranes (Immobilon-Ny+; Millipore, Inc.; procedures essentially as in Sambrook, et al. (1989) *Molecular Cloning: A Laboratory Manual*, Cold Spring Harbor Press, Cold Spring Harbor N.Y.). Recombinant-cosmid-containing clones (Example 3-a) were plated, at a dilution yielding approximately 500 colonies per plating, on an Immobilon-Ny+ membrane overlaid on a LB-agar plate containing 30 g/ml ampicillin. After incubation for 16 h at 37° C., the membrane was replica-plated to a LB-agar plate containing 30 g/ml ampicillin (with membrane and replica plate marked to define registration), and the replica plate was incubated for 16 h at 37° C. The membrane was incubated, successively, 5 min at 22° C. in lysis/denaturation solution (0.5 M NaOH), 5 min at 22° C. in neutralization solution (0.5 M Tris-HCl, pH 7.9), and 5 min at 22° C. in 2×SSC (Sambrook, et al. (1989) *Molecular Cloning: A Laboratory Manual*, Cold Spring Harbor Press, Cold Spring Harbor N.Y.), and was air-dried between sheets of 3 MM filter paper. Hybridization was performed in a hybridization oven in roller bottles containing ExpressHyb hybridization solution (Clontech, Inc.; procedures per instructions of the manufacturer). The membrane was pre-incubated for 90 min at 68° C. in a roller bottle containing 10 ml of hybridization solution, $^{32}$P-labeled 450-nt hybridization probe (preceding paragraph) in 5 ml hybridization solution pre-incubated for 10 min at 95° C. was added to the roller bottle, and the hybridization reaction was allowed to proceed for 2 h at 68° C. Following the hybridization reaction, the membrane was washed three times (10 min each at room temperature) in 2×SSC containing 0.05% SDS, was washed twice (20 min each at 60° C.) in 0.1×SSC containing 0.1% SDS, and was air-dried. Hybridization signals were detected by storage-phosphor imaging. Clones showing positive hybridization ("dots" in the storage-phosphor image) were identified on the corresponding replica plate (by overlaying the storage-phosphor image and the replica plate with correct registration) and were picked. Two membranes, from two platings, were subjected to hybridization. Eleven clones yielded positive hybridization signals (eight on the first membrane, three on the second membrane).

The eleven clones that yielded positive hybridization signals were further assessed by use of colony-PCR (Colony Fast-Screen™ Kit (PCR Screen; Epicentre, Inc.). For each tested clone, a portion of the colony from the replica plate was suspended in 50 µl of PCR-Lyse Solution (Epicentre, Inc.), was incubated 5 min at 99° C., and was chilled on ice. An aliquot of the resulting PCR-ready DNA (0.5 µl) was used as template in a first-round PCR reaction (25 µl) containing 0.2 µM forward primer (SEQ ID 34), 0.2 µM reverse primer (SEQ ID 35), 0.2 mM each dNTP, 0.5 µl of Advantage 2 Polymerase Mix (Clontech, Inc.), and 1×Advantage 2 PCR buffer (initial denaturation for 1 min at 94° C.; followed by 7 cycles, each comprising denaturation for 30 s at 94° C. and annealing and extension for 1 min at 72° C.; followed by 30 cycles, each comprising denaturation for 30 s at 94° C. and annealing and extension for 1 min at 68° C.; followed by final extension for 4 min at 68° C.). The resulting first-round PCR product (0.5 µl of 1:25 dilution) was used a template in a second-round PCR reaction (25 µl) containing 0.2 µM forward primer GGTCCCCGCACACGGCCTTCGGCTTCACG (SEQ ID 36; corresponds to positions 40-68 of SEQ ID 20), 0.2 µM reverse primer (SEQ ID 37), 0.2 mM each dNTP, 0.5 µl of Advantage 2 Polymerase Mix (Clontech, Inc.), and 1×Advantage 2 PCR buffer (initial denaturation for 1 min at 94° C.; followed by 5 cycles, each comprising denaturation for 30 s at 94° C. and annealing and extension for 1 min at 72° C.; followed by 20 cycles, each comprising denaturation for 30 s at 94° C. and annealing and extension for 1 min at 68° C.; followed by final extension for 4 min at 68° C.). Products were analyzed by agarose gel electrophoresis (Sambrook, et al. (1989) *Molecular Cloning: A Laboratory Manual*, Cold Spring Harbor Press, Cold Spring Harbor N.Y.). A distinct product of the expected size of approximately 420 bp was observed for each of the eleven tested clones, confirming presence of sia-I nucleic acid sequences in each of the eleven tested clones. Glycerol stocks were prepared and stored at −70° C.

Example 4-c

Characterization of Nucleic Acid Sequences Encoding Precursor, Processing Factors, and Transport Factors for Siamycin I: Sequence Analysis For one of the eleven confirmed positive clones from Example 4-b, cosmid DNA was subjected to dideoxy nucleotide sequencing. A primer-walking strategy was employed, involving successive iterations of primer design and sequencing. In the first iteration, primers were designed based on the sequence defined by genome walking (SEQ ID 20; Example 2-b); in each subsequent iteration, primers were designed based on sequence determined in the previous iteration. The 8,817 bp sequence obtained in this manner is as follows (SEQ ID 38):

```
TCCACGACGTCGTCACCCACAGCGTGGGCCTGATCGCGATCAAGGCCGGG
GTCGCCAACCACGTCATCGCCACCCACCCCGAGGAGGCCGGAGAGGCCCT
CACCGTCATCGAGGACATCAGCCGCAGGGCGCTGCGCGACATGCGGGCCA
CCCTCAAGGTGCTGCGCCGAGAAGACGACGCCCAGCAGCAGGACCTCCAG
CCGGTCCCCGGACTGTCGGACCTGCCTTCCCTGGTCCGTACGGCCGAGGC
GGCGGGCGTCAGCGTCGACCTGCGCTCCGATTGCGTGGAGGAACCACCCG
ACGGGGTCGCGCTGACCGCGTTCCGGATCGTCCAGGAGGCGCTGACCAAC
GTCGTCAAACACGCTGCCCCGACCCGCTGCCTGGTCAGCGTCACCGCGCA
GGACGGTGTGCTGACGATCGGCGTCACCGACGACGGCCCCGGACCCGGGC
ACCGGCCGACCGTTCCCGGCGGCGCCATGGGGCTCATCGGGATGAGGGAA
CGGGCCGTCGCGCACGGCGGGACCCTCACGGCGGGCCCCCGCCCCGGCGC
GGGCTTCCGGATCCTCGCGACACTGCCGTACTAGTGCCACGCCAACCGCC
ATACGTCCCGCCCCCGCATATGGCTGAAACGGTCTCATACCCCGGTATG
GGTCCGGTCCGCGAAACCGGCCCGCACCGTCCCGACCCCGGTCCGATGTG
TGGCGCGGCCGCCGCGGGCCAGACTCGTCGCGTGATTGACGTCCAGAACC
TGACCAAGCGGTACGGGCCGGCCACCGTCGTGGACGGCCTGACCTTCACG
GTGCGGCCCGGAGCCGTCACCGGCTTCCTCGGCCCCAACGGCGCCGGGAA
GTCGACCACCCTGCGGATGATGCTGGGCCTGACCCGCCCCGACACCGGAA
CCGCGCGGATCGACGGGCACGCCTACGGCGACCTGGCCCACCCCCTCCGC
CGCATCGGCGCCCTGCTGGAGACCTCGGCCCCGCACCGCGGCCTGACCGC
GCGCGACCATCTGCTCTGGCTCGCCCAGAGCAACCGGATCGCCCGCGGCC
GGGTCGCCGAGGTCCTGGAGGCGGTCGGACTCGCGGACGCGGCCCGGCGC
CGGACCGGCACCTTCTCCCTCGGCATGGGCCAGCGGCTGGGCCTGGCCGC
```

```
CGCGCTCCTCGGCGACCCGCCCGTGCTGGTGCTCGACGAACCGGTCAACG
GCCTGGACACCGAGGGCATCCGCTGGCTGCGCGACCTGCTGCGCTCGATG
GCCGCCGAGGGCCGTACCGTCCTCATCTCCAGCCATCTGATGACCGAGAT
GGCCCTGGTCGCCGATCACCTGGTCGTCATCAGCCGGGGCCGGCTCCTCG
CGGACACCGGGATGTCGGACTTCATCGAGCGCCACGGACGGTCGTACGTC
CGGGTCCGCACCGCCGAACCCGACCGGCTCGGCAGGGAGTTGGAAGGCCG
CGGCGCCACGGTGAGCCGCGTCCCCGGCGGCGGCCTGGACGTCGTGGGCA
TGACGGCCGCGGACGTCAGCCGGATCGCCGCGGCGGGCGGCTTCCCGCTC
GACGAACTCGCCACCCACGCCGGGTCGTTGGAGGAGACCTTCCTCGACGT
CGTCGGAGAGGGCCAACAGGTCCACGGTCCGGAAGGCAGGAACACCCATG
TCTGAGACCCTCGCGGCCGTCCGCGCCGAGACCACCAAGCTGCGCGGCAT
TCGCGGCACCCGGATCTCGCTGCTGCTGTTCGCCGCGGTCAGCGTCCTCA
TCGCCGCCCTCGACGGCTGGTCCGCGAAGAACGCGCTGGAGTCCGACAAC
CCCAGCCTGCGTTCCGACTTCACCCCGGAACAGGCCGGTCTCGACGGCAT
CCTCTACGGCCAGTTGGCGCTGATCGTGTTCGGCGTCCTCGTCGTCACCA
GCGAGTACACGTCCGGCATGATCCGTGTCTCCCTGCTCGCCGTCCCCCGG
CGCGGACGGCTCTACGCGGCGAAGACGGTCGTCACCGCCCTGGCGGCGGT
GGCCGTCTCCGTCCCCGTCACCGTCCTCGGCTACCTGGTCACGCAGGCGG
CTCTCGGGTCCCACGGTTCCTCGCTCGGCGCGAGCGGTGTCCCGCGCGCC
CTGGCCGGGGCGGTCGTCTATCTGACCCTGATGTGCCTGTTCGCGGCGGG
TATCGCGGCGATCGCCCGCAACGCCGTCGTACCACTGGCCGTTCTGCTGC
CGATGGTGCTCGCCGGGACGCACATCCTGTCCCTCATCGGGCGACCAAG
GAGATGGCCCGATACTTCCCCGACCAGGCGGGAAACGAACTGCTCACCGT
CCGGTCCCCGCACACGGCCTTCGGCTTCACGGTGCTGCTCGCCTGGACCG
TCGCCGCCCTCGGATGGGGCTGGGTGCGCCAGCGCCGGTGGGACAGCTGA
CAGGACCGGCATGGGACAACTGCCCCATGCCGGTGGGACAGTCCGCCCCG
TAGCTTCCGTGACAGATCACAGGCCGAACAAGGTCGGCCTGACCGATCCG
AAACGGGAGGACACCATGTCCGCGATCTACGAGCCCCCCATGCTCCAGGA
AGTCGGCGACTTCGAGGAGCTCACGAAGTGCCTCGGCGTCGGAAGCTGCA
ACGACTTCGCCGGCTGCGGCTACGCGATCGTCTGCTTCTGGTGATCACGT
CCGGTGCCGGTGCGTTCACGCGCACCGGCACCACCCGGGGTGACGAGGAG
ACGGGGAACGAGGCGACATGGAATTCGTGGTTCTTCCGGACTGCCCGGCC
GGTGCCGCGGCCGTCGGCCGGCTGCGGGCGACGCGGCGCGTCGACCACGC
GTCGGGCGGCCCTGGATCGTCGGCGACTGGCCCGAGGCCGAGGCCGTCG
TCGTCGAGGCGGGCCCACGGCGGATGTCGTACTGGGACACACCCGGCTC
GACGAGACCGCCGCGGCGGCCGCGCTCGGCCGGCTGCGCTCGCTGCACGA
CGTGGACTCGATCGCGTCCCGGCTGCCGGGAGCCGTCCACCTGGCGGTGT
CACTGGACGGCAGGACCAGGGTGCAGGGTTCGGCCGTCGGCGTACGACAG
ATCTTCACCGCCGTCGTCGACGGGGTGACCGTCGCCGCGAGCGGGGTGGA
ACCCCTGCTGCGGCTGACCGGCGCCGGCCTCGACGAGACCGTGCTCGCCG
CCCGCCTGCTGGCGCCGGGCGGACCACCCTGGCCGCTCGCCCAGCGCCCC
GTCCGCCGGGGCGTCGAGGCGCTCACCACCGGCCACTGGCTGGAACTGGA
CACGGACGGCCGGGCCCGGCAGACCCGCTGGTGGGAACTCCCGGAGCCGT
CCCTCACGCTCGCGCAGGGCGCAGCCGCCGTCCGTTCGGCGCTGGACGAC
GCGATCACCAGCCGGGTCGCCGCGGGCGGCACCCTCAGCGCCGACCTGTC
CGGCGGTCTGGACTCCACCTCACTGTGCTTCCTCGCGCACGCGGCCGGCG
CCGACCTGGTCACGTACCACGTGACGCCGATCGACAGCGCCAACGCGGAC
ACGATGTGGGCCCACCGGGCCGCGGAGTGCCTGCCTGCGGCCCGGCACCA
CACGCTGTCCGCCGACCGCGCCGAGAACCTGTTCGACGTCGGCTACACCG
CCGACCTCGTGGGCGCGGCCCCGGAGGGTCCCTCGACCTGGGCCTCCGGA
CTCGCCCACATCCAGGACCTGGCCAAGCGGGCCACGGCGGAGGGCGCCAC
ACTGCACCTGACCGGCTTCGGCGGTGACGAGCTGTTCGGCCGGATGCCCG
CCTGCGCCTGGTCCCTGGCCCGGGCCACACCGGTCGGCGGGCTGCGGCTG
GTCAACCGCTACCGGCTGGCCAATCGCTGGCCGTGGCGGGCGACCGTACG
CTCGCTCCTTGACCGCTCGACGTTCACGCAGAACCTCGGTCGGGTCGCCG
CCCGCATCGACGCCCGCCCCCGCCCGTCGACGAGCCCGACTTCGGCTGG
GTGTTCGCACCCCGCATGCCGGCCTGGGCGACCCCCGACGCCGTGGCCGC
GGTCCGCGCCCTTCTCACCGACGCCGCCACCGAGGGACCCGGGCCGCTGG
ACGCCGACCGGGCCCGGCACCAGGCGCTCGCCTCGTCGTCTTCGAGGGG
ACCACCGTCCGCCAGGTCAACACCGCCCTCGGGGACACCGGCATCACCTG
GGACGCGCCCTTCCTCGACGACCGGGTGGTGGAGGCGGCCCTGGCCACCC
GGATCGACCAGCGCCTGCTCGGCGGGCGGTTCAAGCCGCTGCTCACCTCG
GCCGCACGGGTCTCGTCCCCGCGGACATCCTGGGCCGCCGTGACAAGGG
CGAGTTCAGCGCGGAGGCGTTCCGGGGCCTGGCCCGCAACCGGGCCCGGA
TCCTGGAGCTGTGCGAGGACTCCCAGCTCGCCCGGCTCGGCCTCATCGAC
CCGGCGGCCTTCCGGTCCGCGGTGCTGAACCCGGGGCCGATGTCCCACCA
TCTCCAGCCGATCGACACCACGGTGGCGTGCGAGAGCTGGCTGCGGACGC
ATCCGGAGACGTACCCCATGCCACCCGCCCGGAACACGCCTACGGGAGAA
CACCGATGAAGCTGACCCTCGCCCGCGACGTCACCCTCACCGTCGTCGAC
TCCGGGGCCGTGCTGCTCGACGGGCGCCGCGGCCGCTACTGGCAACTGAA
CCACTCCGGCGCGGGCGTCCTGCGCCAACTGCTCGACGGAACGGCGCCCG
ACGCGGCCGCCGCCGGCCTCTGCGCCGCGGCCCCGGTCAGCGACGACCAG
GCACGGCAGGACGTCCAGGCCCTCATCGACGCGCTCAGCGCGGCCAAGCT
CGTGGAGGTGGCCTCGTGACCACCCCGCCGTGGCCGAACAGGCCCCGCG
GCTGCCCTGGTACCGGCAGCTCGCCCCCGGTGCGCCGGGGGCGGCCC
GTCTGCTGGTCCGGTTGCCGCCGGCCCGACTGCACCGCGTGCTGGGCGTG
GTCAGCAAGGGGTCCCGCCCCGCCGGATACGCCGAGGTGGCGCGGGCCCG
CCGGTCCGTCGTCTCGGTCAGCACCCGCTGCGCGGGACTCGGTTGCCTCC
AGCGTTCCGTGGCCACCGTCCTGCTGTGCCGGGCACACGGCAGGTGGGCC
GACTGGTGCACGGGATTCAGAACCGAACCGTTCGGCGCGCACGCCTGGGT
GGAGGCCGAGGGGCGGCCGGTGGACGAGCCCGGCGAACTCAGCGTGTTCC
```

-continued

```
GCACGGTCCTGGCGGTCCGCCGCCCGGACGGACGCCGGAGCACCTCCGAC
CGTCCCCTCCGCCCCTCCCGAGGGAGCCGCTCATGACAGCGATCCGGGCC
GAGGGCCTCTACGCGTACTACGGCACCGCACCGGCCGTGAACGGGCTCGA
CCTGACCGTGCCCACGGGCAGCGTCTACGGCTTCCTCGGACCGAACGGCG
CGGGCAAGACCACCACCATCAACATGCTGACCACCCTGCTGCGGCCCACC
GCGGGCCGTGCGGAGGTGGCCGGCTTCGACGTCGCCGCCCGGCCCGCCGA
GGTCCGCCGCCGTATCGGCATCGTGTTCCAGGAGTCGACCCTCGACCTGG
ACCTCACCGCCGCCCAGAACCTCCGCTTCCAGGCCGACCTGTGCGGCCTG
TCCCGCCGCGCGTCCCGCGACGCGATCGCCTCGATGCTCGACCTGATGGA
CCTCTCCGAGCGCCGCAGGGTGCCCGTACGGCAGTTCTCCACCGGACTGC
GCCGCCGCCTCGAGATCGCCCGTGGCCTGCTCGCCGAGCCCAGCGTGCTG
TTCCTCGACGAGCCGACGACCGGACTGGACGCCCAGACCCGCGCCGCCGT
CTGGGAGCACCTGGAACGGCTGCGCCGGGAGAGGGGCATCACGGTCTTCG
TCACCACCCATCAACTGGACGAGGCCGAGCACTGCGACCGGATCGCGATC
ATCGACCGGGGCAAGGTGGTCACGGAGGGCACACCAGCGGACCTCAAATC
CGTCATCGGGGCCGACCTCGTCGTCCTGCGCACCGACGACGACCAGCGCG
CCGCCGCCGTCCTCGGCGACCGGTTCGGCCTCCCGGCGGAGCCCACTCCG
GACGGTCTGCTGCTCCGGGTCGAGCGCGCGGCGGCCTTGGTGCCCCGCCT
GTGCACCGAACTCGGCGTGACCGTACGCGAGGTCGCCATCGCCCCGCCCA
CCCTCGACGACGTCTTCCTGCACCACACCGGTCTCGCCATCCGGGAGAGC
CCGACCGGCCCGCGCACGCTCGGCAACCTCGGGGAAGGACTGCGATGAGC
CGGACCGACACCGCACCCGCCGCACTCGGCGACGTCAGCGCCGCACCCTC
ACCGACCGACCGGTCCCGCAACGCGGCGCGCCCCGTCCTGCTGCTCTGGC
GGCGGGAGATGACCCGGCTGCGGCACAACCCCGTGCGCCTGGCCATGGGA
CTCGTGACACCGCTGCTGTTCCTCGTCGTCCTCGGCACCGGCCTCGACGC
GGCGTCGTCCAGCCTCGGCAAGGCCCAACTGAACGACTACCGGGCCTACT
TGTTCCCCGGCACGCTGGTCATGTCCGTGCAGGCGCCGGCGATCGCGGTG
GGCATCTCGCTGGTGTGGGACCGCAGGCTGGGGGTGCTGCGCCAGATGCT
CGTGGCGCCGTTCCCGCGCGCGTCCATCGTGTTCGGACTGGCCTTCGGCG
GCGCCACCACCGGCGCGGTCTACGGCCTCATGGTGCTGTCCGTCGGCGGG
ATCGCGAGCATCCGCTACACGCCGATGCTGCTGGTCGTCCTCCTCGAACT
CCTGCTGGTCTCCCTCATGTTCACCGCGCTCGGGCTGCTCGCCGCCGTCA
CCATCCGGCAGGTCGACACCTTCCAGGTCGTGGTGAACCTGAGCCTGATG
CCGCTGATGTTCTTCTCCGGCGCGATGTTCCCGCCCAACGGCCTGCCCGG
CTGGCTCGACACCGTCGTCAAGCTCAACCCGCTGACGTACGGCGTCGACG
CGGTCCGCCGGACCCTGCCAGGACCGAGCGTGCTCACCTCGGAGCAGACC
CGGCTGATGCTCGGCGACTGGCACCCGCCCGTGGCCGCCGAACTGGGTGT
CCTGGCCGCCCTCACCGCGGTCGCGCTGGGCCTCGCCGGCTACCGGTTCT
CCCGTACGTCATGAGCCGGGGAGGACAGGGGACGGTGGACGCGAGCACCA
CGGATGTGACCACGACGGCCGCCGTCCGGGCCACGACCGGGCACTGGGCG
GGCGCGGCGCGGCTCGTGGCCCGGCTGCTCCTGGCGGCGATCCTGGCCTA
CGCCGGTCTGGTGAAGATCGGGGACCTCACGGAGGCCGGGCGGACGGTCG
CGCTCTACCGCATCGTGCCCGCCGACTCGGCCCAACTCGTGGGCGGCGTC
CTGCCGTTCGTCGAGGTGGCGCTCGCGCTGCTGCTCGCGGCCGGGCTGGC
CACCAGGGCGGCAGCGGCGGGCGCGGCCGTACTGCTGGTCGCCTATGCGG
CGGCCATCGCCTCGGTGTGGGCACGGGCATGTCCATCGACTGCGGCTGT
TTCGGCGGCGGAGGCACGCTCAGCGGTGGCGCCGCACGCGGCTACGCGCT
CGACCTCGCGCGCGATCTGCTGCTGCTCGGCGCGGCCGCCCTCCTGATCC
GGAATCCGCGCACCCGATACGCGCTGGACGGCTGGGTCCTGGACCCGAAG
GAGTGAGGGGCATGACGAGCACACAGACAACGGACGCCACGGTGCGGGAG
ATGGTGCACCGACGGCACCGGCGACGGCGCACAGTGGTGGTGTCTCTGGT
GGCCGCCCTGGTGGTGGTCGCCGCCGCGCTGGTGGGCGCGGGCCTGGTCC
GGGCGAACAACACGGCGCCCGGCAAGGCACCGAGCCGCGTACCGGCCGGG
CTCGCCGCCGACAAGTCGGGCGTGGCCGCCTCCACCGGCGCCGTACGCGT
CGACGTGTACCTCGACTACCTCTGCCCCGAATGCCGTCGTACCGAACGGG
CACTGACCACCGCCCTGGACAGTCTGAGGGCGCACGGCGGGGTGAGCGTC
GTCTACCACCCGGTCGCCTTCCTCGACAGCCGCAGCGCACCCGCGGGCTA
CTCGACCCAGGCGGCCTCCGCGGCGGCCTGCGCGGCGGACGCGGGGAGGT
TCGAGCAGTACTCCACGGTCCTGTTCTCGAAACAGCCCGCCGAACAGGGC
CCTGGGCTCAGCGAGGCCCAGCTGATCGCGGCGGGCCGGGACGCGGGCAT
CACCGCGGCGTCCTTCGCCCGCTGCGTCGAGGACGCCCCCTACCTGCCCT
GGGTACGGTACGTCTCCGATCTCGCCGCCTCCCGCAAGGTGGCGCTGACC
CCGACCGTCATGGTGGCGGGCCGCCGTGTCGACGTCACCGGCTCCGATCC
GGGCGGCGCGCTGACCCGGGCGGTCACGGCGGCCCGGCGGTGACCCGGCT
GACCGTGGCCCTGTCCGGGGACTGCATGGCGACACGGGGAGCGGTGATCT
CCTCCGACCCGGCCGCCGGACGGCTCCACGAACTCCTCCACGGCGCCGAC
TTCGCCGTCACCAACCTGGAGGTGGTGCCCAGCGACGGACGCGGACACCC
GGTGCACAACACGGCCGGTGGCGGCTGTCTGATCGCGGACTCCGGTGTCC
TGGACGAGATCACGTCGGCCGGGTTCACCGTGCTGGGCTGCGCCAACAAC
CACGCCATGGACCTGGGCACGGAGGGCGTGCTCGGCACCGTGGACCTGCT
GCGGTCGAGGCGGATCCCGTTCGCCGGGATCGGCGCCGACCTCACCACGG
CGCGCCGGCCCGTCTACGTCGACCGGCCGGGCGGCAGCCTGGCGCTGCTC
GCCTGCACCGCGACGTT
```

The 8,817 bp sequence contains two presumptive operons.
The first presumptive operon comprises eight tandem ORFs: (i) an ORF encoding the precursor to siamycin I (see Example 2-b); (ii) an ORF encoding a protein that exhibits similarity to amidotransferases, the class of proteins that includes MccJ25 processing factor McjC; (iii) an ORF encoding a protein that exhibits similarity to oxidoreductase-cofactor-synthesis factors involved in disulfide-bond-formation reactions; (iv) an ORF encoding a protein that exhibits similarity to transglutaminases, the class of proteins that includes MccJ25 processing factor McjB; (v) an ORF encoding a protein that exhibits similarity to ABC-transporter ATP-binding subunits, the class of proteins that includes MccJ25 export factor McjD; (vi) an ORF encoding a protein that exhibits similarity to ABC-transporter integral-membrane-protein subunits; (vii) an ORF encoding a protein that exhibits similarity to integral-membrane oxidoreductases involved in disulfide-bond-formation reactions; and (viii) an ORF encoding a protein that exhibits similarity to extracytoplasmic oxidoreductases involved in disulfide-bond-formation reactions. The proteins encoded by the eight ORFs exhibit unequivocal similarity to the proteins encoded by the eight ORFs of the sia-III operon (Example 3-c), with 65-87% amino-acid-sequence identity. We note that this presumptive operon encodes counterparts of the precursor, the processing factors, and the export factor for biosynthesis of lariat-peptide MccJ25 (see Solbiati, et al. (1999) *J. Bacteriol.* 181, 2659-2662). We note further that this presumptive operon encodes counterparts of a oxidoreductase-cofactor-synthesis factor, an integral-membrane oxidoreductase, and an extracytoplasmic oxidoreductase—which are expected to be required for efficient, accurate disulfide-bond-formation by a Gram-positive bacterium, such as the producer strain *Streptomyces* sp. SKH-2344 (see Kadokura, et al. (2003) *Annu. Rev. Biochem.* 72:111-135). We note further that this presumptive operon encodes counterparts of the inferred precursor, the inferred processing factors, and the inferred export factors for biosynthesis of the related multiple-disulfide-bond-containing lariat peptide siamycin III (Example 3-c). Based on these considerations, we infer that this presumptive operon comprises genes for the precursor, the processing factors, and the export factors for biosynthesis of the multiple-disulfide-bond-containing lariat peptide siamycin I. We designate this presumptive operon as the sia-I operon. The sia-I operon is preceded by the sia-I promoter, siaP-I, which has a sequence that conforms to the consensus sequence for a promoter recognized by the major a factor of *Streptomyces* sp., HrdB (Bourn, et al. (1995) *Nucl. Acid Res.* 23, 3696-703). The transcription start site of the sia-I promoter, siaP-I, has been mapped by use of primer extension (Example 2-c)

The second presumptive operon comprises three tandem ORFs: (i) a partial ORF encoding a protein that exhibits similarity to two-component-regulatory-system sensor kinases; (ii) a first ORF encoding a protein that exhibits similarity to peptide-specific ABC-transporter proteins; and (iii) a second ORF encoding a protein that exhibits similarity to peptide-specific ABC-transporter proteins. The proteins encoded by the eight ORFs exhibit unequivocal similarity to the proteins encoded by the last three ORFs of the xia-III operon (Example 3-c), with 68-74% amino-acid-sequence identity. We consider it unlikely that this presumptive operon is involved in, or related to, biosynthesis of siamycin I. However, we cannot exclude the possibility that this presumptive operon is involved in, or related to, biosynthesis of siamycin I (for example, through effects on regulation of the sia-I operon or though effects on export of siamycin I). We designate this presumptive operon as the xia-I operon.

Promoter and ORF sequence coordinates are as follows:
siaP-I, 2427-2456 (core promoter element, −10 region); 2464 (transcription start)
siaA-I, 2516-2644 (SEQ ID 39)
siaB-I, 2718-4559 (SEQ ID 40)
siaC-I, 4556-4819 (SEQ ID 41)
siaD-I, 4816-5286 (SEQ ID 42)
siaE-I, 5283-6248 (SEQ ID 43)
siaF-I, 6245-7114 (SEQ ID 44)
siaG-I, 7135-7656 (SEQ ID 45)
siaH-I, 7662-8393 (SEQ ID 46)
xiaC-I, 1-584
xiaD-I, 648-1655
xiaE-I, 1648-240

ORF properties are summarized in Table 3:

TABLE 3 sia-I/xia-I sequence features.

| ORF Name | ORF Coordinates | Frame | Length (codons) | ORF Inferred Function | ORF Family | ORF Similarity to mcj ORFs (encoded amino-acid sequence identity) | ORF Similarity to sia-III ORFs (encoded amino-acid sequence identity) |
|---|---|---|---|---|---|---|---|
| siaA-I | 2516-2644 | +2 | 43 | siamycin III precursor gene | | | siaA-III (86%) |
| siaB-I | 2718-4559 | +3 | 614 | siamycin I processing-factor gene | amidotransferase genes (asparagine-synthetase-glutamine-hydrolyzing genes) | | siaB-I (77%) |
| siaC-I | 4556-4819 | +2 | 88 | siamycin I processing-factor gene | oxidoreductase cofactor-synthesis genes (pqqD-family genes) | | siaC-III (68%) |
| siaD-I | 4816-5286 | +1 | 157 (GTG start) | siamycin I processing-factor gene | transglutaminase genes | mcjB (29% for: codons 77-133) | siaD-III (87%) |
| siaE-I | 5283-6248 | +3 | 322 | siamycin I transport-factor gene | ABC-transporter ATP-binding- | mcjD (23% for codons 10-221) | siaE-III (75%) |

TABLE 3-continued sia-I/xia-I sequence features.

| ORF Name | ORF Coordinates | Frame | Length (codons) | ORF Inferred Function | ORF Family | ORF Similarity to mcj ORFs (encoded amino-acid sequence identity) | ORF Similarity to sia-III ORFs (encoded amino-acid sequence identity) |
|---|---|---|---|---|---|---|---|
| siaF-I | 6245-7114 | +2 | 290 | siamycin I transport-factor gene | ABC-transporter integral-membrane-subunit genes | | siaF-III (83%) |
| siaG-I | 7135-7656 | +1 | 174 (GTG start) | siamycin I processing-factor gene | integral-membrane-oxidoreductase genes (doxD-family genes) | | siaG-III (70%) |
| siaH-I | 7662-8393 | +3 | 244 | siamycin I processing-factor gene | extracytoplasmic-oxidoreductase genes (dsbA-family genes) | | siaH-III (65%) |
| 'xiaC-I (partial) | 1-584 | +3 | 194 | | | | 'xiaC-III (74%) |
| xiaD-I | 648-1655 | +3 | 336 | | peptide-specific ABC-transporter ATP-binding-subunit genes | | xiaD-III (68%) |
| xiaE-II | 1648-2400 | +1 | 251 | | peptide-specific ABC-transporter integral-membrane-subunit genes | | xiaE-IIII (73%) |

Example 5

Surrogate-Host Expression of Biosynthetic Genes for Non-MccJ25-Related Lariat Peptides

Example 5-a

Surrogate-Host Expression of Biosynthetic Genes for Non-MccJ25-Related Lariat Peptides: Gene Subcloning To accomplish surrogate-host expression of biosynthetic genes for siamycin I in *Escherichia coli*, a DNA fragment carrying siaA-I through siaH-I (positions 2516-8712 of SEQ ID 38) was subcloned, under control of a bacteriophage T7 gene 10 promoter and a lac operator, in *Escherichia coli* expression vector pET29 (Novagen, Inc.); the resulting recombinant plasmid was introduced into *Escherichia coli* expression strain BL21(DE3), which contains a λ-prophage-borne gene encoding bacteriophage T7 RNA polymerase under control of a lac operator (hsdSB(rB⁻mB⁻) dcm ompT tonA gal λ(DE3); Novagen, Inc.); and the resulting cells were cultured in the presence of lac inducer isopropyl-β-D-thiogalactoside (IPTG; Sigma, Inc.). Subcloning was performed by ligation of an NdeI-EcoRI DNA fragment carrying siaA-I through codon 2 of siaB-I (positions 2516-2720 of SEQ ID 38; prepared from sia-I cosmid clone of Examples 4-b and 4-c by use of add-on PCR) and an EcoRI-BamHI DNA fragment carrying codon 2 of siaB-I through siaH-I (positions 2721-8712 of SEQ ID 38; prepared from sia-I cosmid clone of Examples 4-b and 4-c by use of restriction digestion), followed by ligation of the resulting DNA fragment with NdeI/BamHI-digested plasmid pET29 (procedures essentially as in Sambrook, et al. (1989) *Molecular Cloning: A Laboratory Manual*, Cold Spring Harbor Press, Cold Spring Harbor N.Y.).

To accomplish surrogate-host expression of biosynthetic genes for siamycin I in *Streptomyces* sp., a DNA fragment carrying the sia-I promoter and siaA-I through siaH-I (position 2401-8712 of SEQ ID 38) was subcloned, under control of the sia-I promoter, in parallel, in integrative *Escherichia-coli/Streptomyces*-sp. shuttle vector pSET152 (Bierman, et al. (1992) *Gene* 116, 43-49), in low-copy-number replicative *Escherichia-coli/Streptomyces*-sp. shuttle vector pKC1218

(Bierman, et al. (1992) Gene 116, 43-49), and in high-copy-number replicative *Escherichia-coli/Streptomyces*-sp. shuttle vector pWHM4 (Vara et al. (1989) *J. Bacteriol.* 171, 5772-5881); the resulting recombinant plasmids were introduced into plasmid-free *Streptomyces coelicolor* strain CH999 (McDaniel, et al. (1993) *Science* 262, 1546-1550) or plasmid-free *Streptomyces lividans* strain K4-114 (Ziermann, et al. (1999) *BioTechniques* 26, 106-110) (procedures essentially as in Kieser, et al. (2000), *Practical Streptomyces Genetics*, John Innes Center, Norwich UK); and the resulting cells were cultured (procedures essentially as in Kieser, et al. (2000), *Practical Streptomyces Genetics*, John Innes Center, Norwich UK). Subcloning was performed by ligation of an NdeI-EcoRI DNA fragment carrying the sai-I promoter and siaA-I through codon 2 of siaB-I (positions 2401-2720 of SEQ ID 38; prepared from sia-I cosmid clone of Examples 4-b and 4-c by use of add-on PCR) and an EcoRI-BamHI DNA fragment carrying codon 2 of siaB-I through siaH-I nt 2721-8712 of SEQ ID 38; prepared from sia-I cosmid clone of Examples 4-b and 4-c by use of restriction digestion), followed by 3'-end-filling of the resulting DNA fragment and ligation of the resulting DNA fragment with EcoRI-digested, 3'-end-filled plasmid pSET152, pKC1218, or pWHM4 (procedures essentially as in Sambrook, et al. (1989) *Molecular Cloning: A Laboratory Manual*, Cold Spring Harbor Press, Cold Spring Harbor N.Y.).

To accomplish high-level surrogate-host expression of biosynthetic genes for siamycin I in *Streptomyces* sp., a DNA fragment carrying the promoter and siaA-I through siaH-I (positions 2401-8712 of SEQ ID 38) was subcloned, under control of tandem ermA* and sia-I promoters, in high-copy-number replicative *Escherichia-coli/Streptomyces*-sp. shuttle vector pEM4 (Quiros, et al. (1998), *Mol. Microbiol.* 28, 1177-1185; procedures essentially as in previous paragraph); the resulting recombinant plasmid was introduced into plasmid-free *Streptomyces coelicolor* strain CH999 (McDaniel, et al. (1993) *Science* 262, 1546-1550) or plasmid-free *Streptomyces lividans* strain K4-114 (Ziermann, et al. (1999) *BioTechniques* 26, 106-110) (procedures essentially as in Kieser, et al. (2000), *Practical Streptomyces Genetics*, John Innes Center, Norwich UK); and the resulting cells were cultured (procedures essentially as in Kieser, et al. (2000), *Practical Streptomyces Genetics*, John Innes Center, Norwich UK).

Example 5-b

Surrogate-Host Expression of Biosynthetic Genes for Non-MccJ25-Related Lariat Peptides: Gene Synthesis To accomplish high-level surrogate-host expression of biosynthetic genes for siamycin I in *Escherichia coli*, a synthetic DNA fragment carrying derivatives of siaA-I through siaH-I, having codon usage optimized for expression in *Escherichia coli* (see Gustaffson, et al. (2004) *Trends Biotechnol.* 22, 346-353), having translation start sequences optimized for expression in *Escherichia coli* (see Gustaffson, et al. (2004) *Trends Biotechnol.* 22, 346-353) was designed ("syn-sia-I"; SEQ ID 47). The synthetic DNA fragment contains a unique XbaI site preceding siaA-I, a unique NdeI site at the start of siaA-I, a unique HindIII site following siaA-I, a unique NcoI site at the start of siaB-I, and a unique XhoI site following siaH-I. The synthetic DNA fragment permits at least three different cloning and expression strategies: (i) cloning of synthetic siaA-I through siaH-I, under control of a tac promoter and lac operator, in pRL663 (Wang, et al. (1995) *Cell* 81, 341-350; cloning via XbaI and XhoI sites) and expression in *Escherichia coli* in the presence of lac inducer IPTG; (ii) cloning of synthetic siaA-I through siaH-I, under control of a bacteriophage T7 gene 10 promoter and a lac operator, in a pET or Duet *Escherichia coli* expression vector (Novagen, Inc.; cloning via XbaI and XhoI sites, or NdeI and XhoI sites) and expression in *Escherichia coli* expression strain BL21 (DE3) (Novagen, Inc.) in the presence of lac inducer IPTG; and (iii) cloning of synthetic siaA-I, under control of a bacteriophage T7 gene 10 promoter and a lac operator—as a small, easily mutagenized, easily replaced, cassette—in a pET or Duet *Escherichia coli* expression vector (Novagen, Inc.; cloning via XbaI and HindIII sites, XbaI and EcoRI sites, NdeI and HindIII sites, or NdeI and EcoRI sites), separate cloning of synthetic siaB-I through siaH-I, under control of a bacteriophage T7 gene 10 promoter and a lac operator, in a compatible pET or Duet *Escherichia coli* expression vector (Novagen, Inc.; cloning via EcoRI and XhoI sites), and co-expression in *Escherichia coli* expression strain BL21(DE3) (Novagen, Inc.) in the presence of lac inducer IPTG.

To accomplish surrogate-host expression of biosynthetic genes for siamycin II (the known derivative of siamycin I differing by a Val>Ile substitution at position 4), a derivative of synthetic DNA fragment syn-sia-I, "syn-sia-II" (SEQ ID 56), differing by a Val>Ile codon substitution at the corresponding position of siaA was designed.

To accomplish surrogate-host expression of biosynthetic genes for siamycin III (the known derivative of siamycin I differing by a Val>Ile substitution at position 4 and an Ile>Val substitution at position 17), a derivative of synthetic DNA fragment syn-sia-I, "syn-sia-III" (SEQ ID 58), differing by a Val>Ile codon substitution and an Ile>Val codon substitution at the corresponding positions of siaA was designed.

To accomplish surrogate-host expression of biosynthetic genes for siamycin IV (a novel derivative of siamycin I differing by an Ile>Val substitution at position 17), a derivative of synthetic DNA fragment syn-sia-I, "syn-sia-IV" (SEQ ID 60), differing by an Ile>Val codon substitution at the corresponding position of siaA was designed.

Example 5-c

Surrogate-Host Expression of Biosynthetic Genes for Non-MccJ25-Related Lariat Peptides: Detection of Production by Mass Spectrometry Surrogate-host production of siamycins was assessed by use of MALDI-TOF mass spectrometry. This approach detects siamycins based on molecular mass.

Surrogate-host cells harboring plasmids including nucleic acids for siamycin biosynthesis were cultured; cells and culture media were separated by use of centrifugation; peptides in cell lysates (prepared from cells by use of sonication) and peptides in culture media were concentrated and desalted by use of reversed-phase chromatography (ZipTip$_{C18}$ cartridges; Millipore, Inc.; procedures per instructions of the manufacturer); and aliquots (1 μl) of concentrated desalted peptides in cell lysates and concentrated desalted peptides in culture media were mixed with MALDI matrix α-cyano-4-hydroxycinnamic acid (1 μl) and subjected to MALDI-TOF mass spectrometry. In parallel, as a control, the analogous procedure was followed using surrogate-host cells harboring otherwise-identical plasmids not including nucleic acids for siamycin biosynthesis.

Example 5-d

Surrogate Host Expression of Biosynthetic Genes for Non-MccJ25-Related Lariat Peptides: Detection of Production by Cross-Streaking Surrogate-host production of siamycins also was assessed by use of cross-streaking. This approach detects siamycins by detecting inhibition of growth of appropriate bacterial test strains (see Yano, et al. (1996) *Bioorg. Med. Chem* 4, 115-120; Potterat, et al. (1994) Liebigs Annalen der Chemie 7, 741-743; PCT Application Serial No., filed Mar. 13, 2007). Surrogate-host cells harboring plasmids including nucleic acids for siamycin biosynthesis were streaked onto each of three LB agar plates (Sambrook, J., et al. (1989) *Molecular Cloning: A Laboratory Manual*, Cold Spring Harbor Laboratory, Cold Spring Harbor, N.Y.; streak width ~1 cm). Following incubation of the first, second, and third plates for, respectively, 0 h, 6 h, or 12 h at 37° C., bacterial test strains (*Escherichia coli* strain D21f2/tolC (Gram-negative bacterium having tolC and rfa mutations, resulting in increased net permeability to small molecules; tolC::Tn10 rfa lac28 proA23 trp30 his51 rpsL173 ampC tsx81; Fralick, et al. (1994) *J. Bacteriol.* 176, 6404-6406) and *Bacillus subtilis* strain MH536 (Gram-positive bacterium; pheA1 trpC2 rpoC::Hisx10 Cm; Qi, et al., (1998) *Mol. Microbiol.* 28, 1187-1197)) were streaked onto the plates at right angles to the previous streak; plates were further incubated for 24 h at 37° C.; and inhibition of growth of the bacterial test strains was assessed. In parallel, as a control, the analogous procedure was followed using surrogate-host cells harboring otherwise-identical plasmids not including nucleic acids for siamycin biosynthesis.

Example 6

Identification of Candidate Biosynthetic Genes for Novel Non-MccJ25-Related Lariat Peptides

Example 6-a

Informatics Searches Using siaB Sequences

PSI-BLAST analyses (Altschul, et al. (1997) *Nucl. Acids Res.* 25, 3389-3402) were performed using as queries the translated amino acid sequences of siaB-III and siaB-I (frame-1 translations of SEQ IDs 27 and 40). Sequences yielding highest-scoring alignments include the following (wherein each entry lists the sequence accession number, the sequence name, the score in bits, and the E value):
gi|29826799|ref|NP_821433.1| asparagine synthetase [Streptomy . . . 367 1e-99
gi|29832232|ref|NP_826866.1| asparagine synthetase [Streptomy . . . 294 1e-77
gi|72161549|ref|YP_289206.1| hypothetical protein Tfu_1145 [T . . . 267 1 e-69
gi|111224311|ref|YP_715105.1| hypothetical protein FRAAL4922 . . . 250 2e-64
gi|86741672|ref|YP_482072.1| asparagine synthase [*Frankia* sp . . . 229 4e-58
gi|23016842|ref|ZP_00056594.1| COG0367: Asparagine synthase ( . . . 76.6 4e-12
gi|86740804|ref|YP_481204.1| putative asparagine synthetase [ . . . 74.3 2e-11
gi|6978034|gb|AAF34252.1|AF168003_7 putative asparagine syntheta 67.4 3e-09
gi|110680990|ref|YP_683997.1| asparagine synthetase, putative . . . 67.0 3e-09
gi|83309141|ref|YP_419405.1| Asparagine synthase [Magnetospir . . . 65.9 7e-09
gi|56963533|ref|YP_175264.1| asparagine synthetase, glutamine . . . 64.7 1e-08
gi|115522609|ref|YP_779520.1| asparagine synthase (glutamine- . . . 64.3 2e-08
gi|86740803|ref|YP_481203.1| putative asparagine synthetase [ . . . 62.8 5e-08
gi|83593324|ref|YP_427076.1| Asparagine synthase, glutamine-h . . . 62.4 9e-08
gi|71065234|ref|YP_263961.1| probable asparagine synthase, gl . . . 62.0 9e-08
gi|87200341|ref|YP_497598.1| Asparagine synthase, glutamine-h . . . 62.0 1e-07
gi|21218929|ref|NP_624708.1| asparagine synthetase [Streptomy . . . 60.8 2e-07
gi|20807299|ref|NP_622470.1| Asparagine synthase (glutamine-h . . . 60.1 4e-07
gi|32141226|ref|NP_733627.1| secreted protein [*Streptomyces* c . . . 60.1 4e-07
gi|110635217|ref|YP_675425.1| asparagine synthase (glutamine- . . . 60.1 4e-07
gi|32473186|ref|NP_866180.1| asparagine synthetase [glutamine . . . 59.3 6e-07
gi|106889019|ref|ZP_01356219.1| Asparagine synthase [Roseifle . . . 58.9 8e-07
gi|118581276|ref|YP_902526.1| asparagine synthase (glutamine- . . . 58.2 1e-06
gi|46202015|ref|ZP_00208351.1| COG0367: Asparagine synthase ( . . . 58.2 1e-06
gi|88945850|ref|ZP_01149013.1| Asparagine synthase, glutamine . . . 58.2 2e-06
gi|83368117|ref|ZP_00912982.1| similar to asparagine syntheta . . . 58.2 2e-06
gi|66046975|ref|YP_236816.1| Asparagine synthase, glutamine-h . . . 57.4 2e-06
gi|118069288|ref|ZP_01537534.1| asparagine synthase (glutamin . . . 57.4 2e-06
gi|118744654|ref|ZP_01592644.1| asparagine synthase (glutamin . . . 57.4 2e-06
gi|118716506|ref|ZP_01569043.1| asparagine synthase (glutamin . . . 56.6 4e-06
gi|77460321|ref|YP_349828.1| Asparagine synthase, glutamine-h . . . 56.6 4e-06
gi|71737773|ref|YP_273763.1| asparagine synthase (glutamine-h . . . 56.2 5e-06
gi|118712295|ref|ZP_01564866.1| asparagine synthase (glutamin . . . 56.2 5e-06
gi|28868839|ref|NP_791458.1| asparagine synthetase, glutamine . . . 56.2 5e-06
gi|118759451|ref|ZP_01607145.1| asparagine synthase (glutamin . . . 56.2 6e-06
gi|70731683|ref|YP_261425.1| asparagine synthase (glutamine-h . . . 56.2 6e-06
gi|56477862|ref|YP_159451.1| amidotransferase, similar to asp . . . 55.8 8e-06
gi|22657438|gb|AAN04235.1| putative asparagine synthetase [Strep 55.8 8e-06
gi|124876705|gb|EAY66695.1| Asparagine synthase (glutamine-hy . . . 55.8 8e-06
gi|104784419|ref|YP_610917.1| Asparagine synthase (glutamine- . . . 55.8 8e-06
gi|84352491|ref|ZP_00977450.1| COG0367: Asparagine synthase ( . . . 55.5 8e-06 gi|32328348|gb|AAO67512.1| asparagine synthase [*Pseudomonas* syri 55.5 9e-06
gi|118580879|ref|YP_902129.1| asparagine synthase (glutamine-... 55.5 1e-05
gi|73539195|ref|YP_299562.1| Asparagine synthase, glutamine-h... 55.5 1e-05
gi|107025879|ref|YP_623390.1| Asparagine synthase, glutamine-... 55.5 1e-05
gi|83594451|ref|YP_428203.1| Asparagine synthase, glutamine-h... 55.1 1e-05
gi|84359473|ref|ZP_00984216.1| COG0367: Asparagine synthase (... 55.1 1e-05
gi|118059243|ref|ZP_01527701.1| asparagine synthase (glutamin... 55.1 1e-05
gi|83309204|ref|YP_419468.1| Asparagine synthase [Magnetospir... 54.7 1e-05
gi|20271385|gb|AAL59407.2| putative asparagine synthetase [Bu... 54.7 2e-05
gi|118694730|ref|ZP_01552814.1| asparagine synthase (glutamin... 54.7 2e-05
gi|58336505|ref|YP_193090.1| asn synthetase [*Lactobacillus* ac... 54.3 2e-05
gi|121998294|ref|YP_001003081.1| asparagine synthase (glutami... 54.3 2e-05
gi|38639346|gb|AAR25812.1| putative asparagine synthetase [Burkh 54.3 2e-05
gi|94415380|ref|ZP_01295224.1| hypothetical protein PaerP_010... 53.9 2e-05
gi|15598655|ref|NP_252149.1| probable glutamine amidotransfer... 53.9 3e-05
gi|115358966|ref|YP_776104.1| asparagine synthase (glutamine-... 53.5 4e-05
gi|23128937|ref|ZP_00110773.1| COG0367: Asparagine synthase (... 53.1 4e-05
gi|116623198|ref|YP_825354.1| asparagine synthase (glutamine-... 53.1 4e-05
gi|114845000|ref|ZP_01455429.1| Asparagine synthase, glutamin... 53.1 4e-05
gi|124267909|ref|YP_001021913.1| Asparagine synthase (glutami... 53.1 4e-05
gi|76797017|ref|ZP_00779361.1| Asparagine synthase, glutamine... 53.1 5e-05
gi|56964345|ref|YP_176076.1| asparagine synthetase, glutamine... 53.1 5e-05
gi|103487403|ref|YP_616964.1| Asparagine synthase, glutamine-... 53.1 5e-05
gi|77463112|ref|YP_352616.1| putative asparagine synthetase [... 52.8 5e-05
gi|126461984|ref|YP_001043098.1| asparagine synthase [Rhodoba... 52.8 7e-05
gi|91200308|emb|CAJ73353.1| similar to aspargine synthase Asn... 52.4 7e-05
gi|84319706|ref|ZP_00968096.1| COG0367: Asparagine synthase (... 52.4 8e-05
gi|57157783|dbj|BAD83576.1|glutamine amidotransferase [Rhodococ 52.4 8e-05
gi|119899536|ref|YP_934749.1| probable asparagine synthase [A... 52.4 8e-05
gi|77165432|ref|YP_343957.1| Asparagine synthase, glutamine-h... 52.0 1e-04
gi|52548776|gb|AAU82625.1| asparagine synthetase protein [uncult 51.6 1e-04
gi|89098040|ref|ZP_01170926.1| asparagine synthetase (glutami... 51.6 1e-04
gi|106889566|ref|ZP_01356764.1| Asparagine synthase, glutamin... 51.6 1e-04 gi|74316078|ref|YP_313818.1| asparagine synthase, glutamine-h... 51.2 2e-04
gi|56419441|ref|YP_146759.1| asparagine synthetase [Geobacil... 51.2 2e-04
gi|32477976|ref|NP_870970.1| asparagine synthetase [Rhodopire... 51.2 2e-04
gi|15614071|ref|NP_242374.1| asparagine synthetase [*Bacillus*... 50.8 2e-04
gi|82499488|ref|ZP_00884932.1| Asparagine synthase, glutamine... 50.8 3e-04
gi|87124114|ref|NP_01079964.1| Asparagine synthase, glutamine... 50.4 3e-04
gi|16265108|ref|NP_437900.1| putative asparagine synthetase p... 50.4 3e-04
gi|116623712|ref|YP_825868.1| asparagine synthase (glutamine-... 50.4 3e-04
gi|51891369|ref|YP_074060.1| asparagine synthetase [Symbiobac... 50.4 3e-04
gi|54024871|ref|YP_119113.1| hypothetical protein nfa29020 [N... 50.1 4e-04
gi|86748673|ref|YP_485169.1| Asparagine synthase, glutamine-h... 50.1 4e-04
gi|38639355|gb|AAR25820.1| putative asparagine synthetase [Burkh 50.1 4e-04
gi|118063200|ref|ZP_01531542.1| Asparagine synthase, glutamin... 49.7 5e-04
gi|78223379|ref|YP_385126.1| Asparagine synthase, glutamine-h... 49.7 5e-04
gi|42518221|ref|NP_964151.1| asparagine synthase [Lactobacill... 49.7 6e-04
gi|116628813|ref|YP_813985.1| Asparagine synthase (glutamine-... 49.7 6e-04
gi|78061708|ref|YP_371616.1| Asparagine synthase, glutamine-h... 49.3 6e-04
gi|67155155|ref|ZP_00416783.1| Asparagine synthase, glutamine... 49.3 6e-04
gi|89201113|ref|ZP_01179860.1| Asparagine synthase, glutamine... 49.3 6e-04
gi|111018151|ref|YP_701123.1| asparagine synthase (glutamine-... 49.3 7e-04
gi|126667452|ref|ZP_01738423.1| Asparagine synthase, glutamin... 49.3 7e-04
gi|13474904|ref|NP_106474.1| asparagine synthetase [Mesorhizo... 49.3 7e-04
gi|73621274|gb|AAZ78328.1| OxyD [*Streptomyces rimosus*] 48.9 8e-04

Sequences yielding highest-scoring alignments were deemed to be possible candidates to be biosynthetic genes for novel lariat peptides.

Example 6-b

Informatics Searches Using siaC Sequences

PSI-BLAST analyses (Altschul, et al. (1997) *Nucl. Acids Res.* 25, 3389-3402) were performed using as queries the translated amino acid sequences of siaC-III and siaC-I (frame-1 translations of SEQ IDs 28 and 41). Sequences yielding highest-scoring alignments include the following (wherein each entry lists the sequence accession number, the sequence name, the score in bits, and the E value):
gi|86741671|ref|YP_482071.1| hypothetical protein Francci3_29... 124 9e-28
gi|72161548|ref|YP_289205.1| hypothetical protein Tfu_1144 [T... 116 3e-25
gi|29832231|ref|NP_826865.1| hypothetical protein SAV5688 [St... 114 1e-24 gi|29826798|ref|NP_821432.1| hypothetical protein SAV258 [Str . . . 114 2e-24
gi|111224310|ref|YP_715104.1| hypothetical protein FRAAL4921 . . . 111 9e-24
gi|118763002|ref|ZP_01610685.1| hymidylate synthase-like [Sph . . . 59.4 6e-08
gi|53804936|ref|YP_113381.1| hypothetical protein MCA0892 [Me . . . 55.6 7e-07
gi|83648688|ref|YP_437123.1| hypothetical protein HCH_06047 [ . . . 49.4 5e-05
gi|71280202|ref|YP_269582.1| hypothetical protein CPS_2877 [C . . . 47.9 2e-04
gi|119484896|ref|ZP_01619378.1| thymidylate synthase-like pro . . . 46.7 4e-04
gi|114777025|ref|ZP_01452045.1| hypothetical protein SPV1_066 . . . 46.3 5e-04
gi|13474384|ref|NP_105952.1| similar to hymidylate synthase [ . . . 46.0 6e-04
gi|118578496|ref|YP_899746.1| hypothetical protein Ppro_0048 . . . 45.6 8e-04

Sequences yielding highest-scoring alignments were deemed to be possible candidates to be biosynthetic genes for novel lariat peptides.

Example 6-b

Informatics Searches Using siaD Sequences

PSI-BLAST analyses (Altschul, et al. (1997) *Nucl. Acids Res.* 25, 3389-3402) were performed using as queries the translated amino acid sequences of siaD-III and siaD-I (frame-1 translations of SEQ IDs 29 and 42). Sequences yielding highest-scoring alignments include the following (wherein each entry lists the sequence accession number, the sequence name, the score in bits, and the E value):
gi|72161547|ref|YP_289204.1| hypothetical protein Tfu_1143 [T . . . 122 5e-27
gi|113935986|ref|ZP_01421882.1| conserved hypothetical protei . . . 119 5e-26
gi|29832230|ref|NP_826864.1| hypothetical protein SAV5687 [St . . . 117 2e-25
gi|86741670|ref|YP_482070.1| hypothetical protein Francci3_29 . . . 113 3e-24
gi|113937091|ref|ZP_01422975.1|conserved hypothetical protei . . . 111 1e-23
gi|111224309|ref|YP_715103.1| conserved hypothetical protein; . . . 107 2e-22
gi|119875141|ref|ZP_01642263.1| hypothetical protein SmalDRAF . . . 106 3e-22
gi|126438411|ref|YP_001058938.1| hypothetical protein BURPS66 . . . 104 1e-21
gi|103488013|ref|YP_617574.1| hypothetical protein Sala_2534 . . . 104 1e-21
gi|76811605|ref|YP_333463.1| hypothetical protein BURPS1710b_ . . . 103 2e-21
gi|53719408|ref|YP_108394.1| hypothetical protein BPSL1795 [B . . . 103 3e-21
gi|90289883|ref|ZP_01209579.1| hypothetical protein Bpse17_02 . . . 102 4e-21
gi|126451596|ref|YP_001066181.1| hypothetical protein BURPS11 . . . 101 9e-21
gi|100120104|ref|ZP_01326374.1| hypothetical protein BpseS_03 . . . 101 1e-20
gi|94495347|ref|ZP_01301928.1| hypothetical protein SKA58_026 . . . 101 1e-20
gi|83720676|ref|YP_442959.1| hypothetical protein BTH_12438 [ . . . 101 2e-20
gi|53723444|ref|YP_102882.1| hypothetical protein BMA1201 [Bu . . . 101 2e-20
gi|82536894|ref|ZP_00895896.1| hypothetical protein Bpse110_0 . . . 101 2e-20
gi|86740805|ref|YP_481205.1| hypothetical protein Francci3_21 . . . 100 2e-20
gi|67639383|ref|ZP_00438246.1| hypothetical protein BmalG_010 . . . 100 3e-20
gi|29828740|ref|NP_823374.1| hypothetical protein SAV2198 [St . . . 97.5 2e-19
gi|16126945|ref|NP_421509.1| hypothetical protein CC_2712 [Ca . . . 95.6 6e-19
gi|68234008|ref|ZP_00573109.1| hypothetical protein Franean1D . . . 95.2 9e-19
gi|134102265|ref|YP_001107926.1] hypothetical protein SACE_58 . . . 91.0 2e-17
gi|113934368|ref|ZP_01420269.1| conserved hypothetical protein . . . 88.7 9e-17
gi|103488081|ref|YP_617642.1| hypothetical protein Sala_2603 . . . 84.12e-15
gi|53805179|ref|YP_113379.1| hypothetical protein MCA0888 [Me . . . 80.6 2e-14
gi|48474707|sp|Q9X2V8|MCJB_ECOLI Microcin J25-processing prot . . . 80.2 3e-14

Sequences yielding highest-scoring alignments were deemed to be possible candidates to be biosynthetic genes for novel lariat peptides.

Example 6-d

Informatics Searches Using Multiple sia Sequences

Results from Example 6-a, Example 6-b, and Example 6-c were compared and cross-referenced.

In cases where sequences yielding highest-scoring alignments in at least two of Example 6-a, Example 6-b, and Example 6-c were sequences from the same organism—especially in cases where said sequences were clustered, separated by <5000 bp, in the genome of the organism—said sequences were deemed to be strong candidates to be biosynthetic genes for novel lariat peptides. Examples include:
>gi|11224311|ref|YP_715105.1| hypothetical protein FRAAL4922 *[Frankia alni* ACN14a];
>gi|111224310|ref|YP_715104.1| hypothetical protein FRAAL4921 *[Frankia alni* ACN14a];
>gi|111224309|ref|YP_715103.1| conserved hypothetical protein; putative polyketide beta-ketoacyl synthase [*Frankia alni* ACN14a]
>gi|86741672|ref|YP_482072.1| asparagine synthase [*Frankia* sp. CcI3];
>gi|86740804|ref|YP_481204.1| putative asparagine synthetase [*Frankia* sp. CcI3];
>gi|86740803|ref|YP_481203.1| putative asparagine synthetase [*Frankia* sp. CcI3];
>gi|86741671|ref|YP_482071.1| hypothetical protein Francci3_2985 *[Frankia* sp. CcI3];
>gi|86741670|ref|YP_482070.1| hypothetical protein Francci3_2984 *[Frankia* sp. CcI3];
>gi|86740805|ref|YP_481205.1| hypothetical protein Francci3_2104 *[Frankia* sp. CcI3]
>gi|13474904|ref|NP_106474.1| asparagine synthetase [*Mesorhizobium loti* MAFF303099];
>gi|13474384|ref|NP_105952.1| similar to hymidylate synthase [*Mesorhizobium loti* MAFF303099]
>gi|53804936|ref|YP_113381.1| hypothetical protein MCA0892 *[Methylococcus capsulatus* str. Bath];

>gi|53805179|ref|YP_113379.1| hypothetical protein MCA0888 [*Methylococcus capsulatus* str. Bath]
>gi|118581276|ref|YP_902526.1| asparagine synthase (glutamine-hydrolyzing) [*Pelobacter propionicus* DSM 2379]; >gi|118580879|ref|YP_902129.1| asparagine synthase (glutamine-hydrolyzing) [*Pelobacter propionicus* DSM 2379]; >gi|118578496|ref|YP_899746.1| hypothetical protein Ppro_0048 [*Pelobacter propionicus* DSM 2379];
>gi|118759451|ref|ZP_01607145.1| asparagine synthase (glutamine-hydrolyzing) [*Sphingomonas wittichii* RW1];
>gi|118763002|ref|ZP_01610685.1| hymidylate synthase-like [*Sphingomonas wittichii* RW1]
>gi|103487403|ref|YP_616964.1| Asparagine synthase, glutamine-hydrolyzing [*Sphingopyxis alaskensis* RB2256];
>gi|103488013|ref|YP_617574.1| hypothetical protein Sala_2534 [*Sphingopyxis alaskensis* RB2256];
>gi|103488081|ref|YP_617642.1| hypothetical protein Sala_2603 [*Sphingopyxis alaskensis* RB2256]
>gi|29826799|ref|NP_821433.1| asparagine synthetase [*Streptomyces avermitilis* MA-4680];
>gi|29832232|ref|NP_826866.1| asparagine synthetase [*Streptomyces avermitilis* MA-4680];
>gi|29832231|ref|NP_826865.1| hypothetical protein SAV5688 [*Streptomyces avermitilis* MA-4680];
>gi|29826798|ref|NP_821432.1| hypothetical protein SAV258 [*Streptomyces avermitilis* MA-4680];
>gi|29832230|ref|NP_826864.1| hypothetical protein SAV5687 [*Streptomyces avermitilis* MA-4680];
>gi|29828740|ref|NP_823374.1| hypothetical protein SAV2198 [*Streptomyces avermitilis* MA-4680]
>gi 72161549|ref|YP_289206.1| hypothetical protein Tfu_1145 [*Thermobifida fusca* YX];
>gi|72161548|ref|YP_289205.1| hypothetical protein Tfu_1144 [*Thermobifida fusca* YX];
>gi/72161547|ref|YP_289204.1| hypothetical protein Tfu_1143 [*Thermobifida fusca* YX]

In cases where sequences yielding highest-scoring alignments in all three of Example 6-a, Example 6-b, and Example 6-c were sequences from the same organism—especially in cases where said sequences were clustered, separated by <5000 bp, in the genome of the organism—said sequences were deemed to be very strong candidates to be biosynthetic genes for novel lariat peptides. Examples include:
>gi|111224311|ref|YP_715105.1| hypothetical protein FRAAL4922 [*Frankia alni* ACN14a];
>gi|111224310|ref|YP_715104.1| hypothetical protein FRAAL4921 [*Frankia alni* ACN14a];
>gi|111224309|ref|YP_715103.1| conserved hypothetical protein; putative polyketide beta-ketoacyl synthase [*Frankia alni* ACN14a]
>gi|86741672|ref|YP_482072.1| asparagine synthase [*Frankia* sp. CcI3];
>gi|86740804|ref|YP_481204.1| putative asparagine synthetase [*Frankia* sp. CcI3];
>gi|86740803|ref|YP_481203.1| putative asparagine synthetase [*Frankia* sp. CcI3];
>gi|86741671|ref|YP_482071.1| hypothetical protein Francci3_2985 [*Frankia* sp. CcI3];
>gi|86741670|ref|YP_482070.1| hypothetical protein Francci3_2984 [*Frankia* sp. CcI13];
>gi|86740805|ref|YP_481205.1| hypothetical protein Francci3_2104 [*Frankia* sp. CcI3]
>gi|29826799|ref|NP_821433.1| asparagine synthetase [*Streptomyces avermitilis* MA-4680];
>gi|29832232|ref|NP_826866.1 asparagine synthetase [*Streptomyces avermitilis* MA-4680];
>gi|29832231|ref|NP_826865.1| hypothetical protein SAV5688 [*Streptomyces avermitilis* MA-4680];
>gi|29826798|ref|NP_821432.1| hypothetical protein SAV258 [*Streptomyces avermitilis* MA-4680];
>gi|29832230|ref|NP_826864.1| hypothetical protein SAV5687 [*Streptomyces avermitilis* MA-4680];
>gi|29828740|ref|NP_823374.1| hypothetical protein SAV2198 [*Streptomyces avermitilis* MA-4680]
>gi|72161549|ref|YP_289206.1| hypothetical protein Tfu_1145 [*Thermobifida fusca* YX];
>gi|72161548|ref|YP_289205.1| hypothetical protein Tfu_1144 [*Thermobifida fusca* YX];
>gi|72161547|ref|YP_289204.1| hypothetical protein Tfu_1143 [*Thermobifida fusca* YX]

In cases where, further, said sequences were preceded by an ORF having the encoded amino-acid-sequence pattern $((Xaa)_{1-100}$-Leu-Thr-Lys-(Gly or Cys)-$(Xaa)_{6-7}$-(Glu or Asp)-$(Xaa)_{5-25}$-(carboxyl-terminus))—a pattern derived from comparison of the encoded amino sequences of the precursors of cJ25, siamycin III, and siamycin I (see Solbiati, et al. (1999) *J. Bacteria.* 181, 2659-2662; Example 1b; Example 2b), and from consideration of the covalent structures of McJ25, siamycin III, and siamycin I (FIG. 1)—said sequences were deemed to be extremely strong candidates to be biosynthetic genes for novel lariat peptides.

The invention claimed is:

1. An isolated nucleic acid sequence encoding at least one of a precursor of a lariat peptide, a processing factor of a lariat peptide, and an export factor of a lariat peptide, wherein the lariat peptide is a compound according to general structural formula (I):

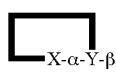

(I)

wherein:
(i) X is an amino acid residue containing a backbone nitrogen atom;
(ii) Y is an amino acid residue containing a side-chain carboxyl group;
(iii) α is a peptide segment of from about 5 to about 8 amino acid residues;
(iv) β is a peptide segment of from about 6 to about 15 amino acid residues;
(v) there is an amide bond between the backbone nitrogen atom of X and the side-chain carboxyl of Y; and
(vi) wherein the lariat peptide has less than 25% sequence identity with microcin J25 (MccJ25).

2. The nucleic acid sequence of claim 1, wherein the nucleic acid sequence encodes a precursor of the lariat peptide.

3. The nucleic acid sequence of claim 1, wherein the nucleic acid sequence encodes a processing factor of the lariat peptide.

4. The nucleic acid sequence of claim 1, wherein the nucleic acid sequence encodes an export factor of the lariat peptide.

5. The nucleic acid sequence of claim 1, wherein the lariat peptide is a siamycin.

6. The nucleic acid sequence of claim 5, wherein the lariat peptide is siamycin II.

7. The nucleic acid sequence of claim 6, comprising at least one sequence selected from the group consisting of SEQ ID NOs. 56 and 57.

8. The nucleic acid sequence of claim 5, wherein the lariat peptide is siamycin III.

9. The isolated nucleic acid sequence of claim 8, comprising the nucleotide sequence of SEQ ID NO. 25.

10. The nucleic acid sequence of claim 5, wherein the lariat peptide is siamycin IV.

11. The nucleic acid sequence of claim 10, comprising at least one sequence selected from the group consisting of SEQ ID NOs. 60 and 61.

12. The nucleic acid sequence of claim 1, wherein the lariat peptide is siamycin I.

13. The nucleic acid sequence of claim 1 comprising at least one nucleotide sequence selected from group consisting of SEQ ID NOs. 20, 38, 39, 40, 41, 42, 43, 44, 45, 46, 47, 48, 49, 50, 51, 52, 53, 54, and 55.

14. The nucleic acid sequence of claim 1, wherein the lariat peptide is a derivative of a siamycin.

15. The nucleic acid sequence of claim 14, wherein the lariat peptide is a derivative of a siamycin selected from a group consisting of siamycin I, siamycin III and siamycin IV.

16. The nucleic acid sequence of claim 1 produced by biosynthesis.

17. The nucleic acid sequence of claim 1 produced by chemical synthesis.

18. A method of preparing a lariat peptide compound according to general structural formula (I):
wherein:
(i) X is an amino acid residue containing a backbone nitrogen atom;
(ii) Y is an amino acid residue containing a side-chain carboxyl group;
(iii) α is a peptide segment of from about 5 to about 8 amino acid residues;
(iv) β is a peptide segment of from about 6 to about 15 amino acid residues;
(v) there is an amide bond between the backbone nitrogen atom of X and the side-chain carboxyl of Y; and
(vi) wherein the lariat peptide has less than 25% sequence identity with microcin J25 (MccJ25);
said method comprising the steps of:
(a) providing the isolated nucleic acid sequence set forth in claim 1 encoding at least one of:
  (i) a precursor of the lariat peptide compound according to general structural formula (I);
  (ii) a processing factor of a lariat peptide according to general structural formula (I); and
  (iii) an export factor of a lariat peptide according to general structural formula (I);
(b) introducing the nucleic sequence into a bacterial host cell;
(c) culturing the nucleic-sequence-containing bacterial host cell; and
(d) isolating a lariat peptide according to general structural formula (I) from at least one of a culture medium and a bacterial cell.

19. The method of claim 18, wherein the lariat peptide is a siamycin.

20. The method of claim 19, wherein the lariat peptide is siamycin I.

21. The method of claim 20, wherein the nucleic acid sequence contains at least one of SEQ ID NOs. 20, 38, 39, 40, 41, 42, 43, 44, 45, 46, 47, 48, 49, 50, 51, 52, 53, 54, and 55.

22. The method of claim 19, wherein the lariat peptide is siamycin III.

23. A method of at least one of identifying or detecting a nucleic acid sequence comprising the steps of:
(a) providing the isolated nucleic acid sequence set forth in claim 1 that encodes at least one of a precursor of the lariat peptide, a processing factor of a lariat peptide, and an export factor of a lariat peptide, wherein the lariat peptide is a lariat peptide according to general structural formula (I):

wherein:
(i) X is an amino acid residue containing a backbone nitrogen atom;
(ii) Y is an amino acid residue containing a side-chain carboxyl group;
(iii) α is a peptide segment of from about 5 to about 8 amino acid residues;
(iv) β is a peptide segment of from about 6 to about 15 amino acid residues;
(v) there is an amide bond between the backbone nitrogen atom of X and the side-chain carboxyl of Y;
(vi) and wherein the lariat peptide has less than 25% sequence identity with microcin J25 (MccJ25);
(b) contacting a test sample containing at least one nucleic acid sequence of interest with the nucleic acid sequence; and
(c) detecting hybridization between a nucleic acid sequence of interest and the nucleic acid sequence.

24. The method of claim 23, wherein the test sample contains the nucleic acid sequence from a bacterial strain.

* * * * *

UNITED STATES PATENT AND TRADEMARK OFFICE
Certificate

Patent No. 8,461,314 B2　　　　　　　　　　　　　　　　　　　Patented: June 11, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Richard H. Ebright, North Brunswick, NJ (US); Konstantin Severinov, Piscataway, NJ (US); Ekaterina Semenova, Highland Park, NJ (US); Anatoliy Kravets, Rochester, NY (US) and Rui Rong Niedfeldt, Princeton Junction, NJ (US).

Signed and Sealed this Twenty-fourth Day of June 2014.

MANJUNATH RAO
*Supervisory Patent Examiner*
Art Unit 1656
Technology Center 1600

SEQUENCE LISTING

<160> NUMBER OF SEQ ID NOS: 69

<210> SEQ ID NO 1
<211> LENGTH: 26
<212> TYPE: DNA
<213> ORGANISM: Artificial Sequence
<220> FEATURE:
<223> OTHER INFORMATION: SEQ ID 1; primer Example 1a-b,d. "n" denotes deoxyinosine.
<220> FEATURE:
<221> NAME/KEY: misc_feature
<222> LOCATION: (9)..(9)
<223> OTHER INFORMATION: n is deoxyinosine
<220> FEATURE:
<221> NAME/KEY: misc_feature
<222> LOCATION: (12)..(12)
<223> OTHER INFORMATION: n is deoxyinosine
<220> FEATURE:
<221> NAME/KEY: misc_feature

```
<222> LOCATION: (15)..(15)
<223> OTHER INFORMATION: n is deoxyinosine
<220> FEATURE:
<221> NAME/KEY: misc_feature
<222> LOCATION: (21)..(21)
<223> OTHER INFORMATION: n is deoxyinosine

<400> SEQUENCE: 1
ccaraacana cnacngcrta nccrca                                               26

<210> SEQ ID NO 2
<211> LENGTH: 29
<212> TYPE: DNA
<213> ORGANISM: Artificial sequence
<220> FEATURE:
<223> OTHER INFORMATION: SEQ ID 2; primer Example 1a-b,d; "n" denotes
      deoxyinosine.
<220> FEATURE:
<221> NAME/KEY: misc_feature
<222> LOCATION: (12)..(12)
<223> OTHER INFORMATION: n is deoxyinosine
<220> FEATURE:
<221> NAME/KEY: misc_feature
<222> LOCATION: (15)..(15)
<223> OTHER INFORMATION: n is deoxyinosine
<220> FEATURE:
<221> NAME/KEY: misc_feature
<222> LOCATION: (21)..(21)
<223> OTHER INFORMATION: n is deoxyinosine
<220> FEATURE:
<221> NAME/KEY: misc_feature
<222> LOCATION: (24)..(24)
<223> OTHER INFORMATION: n is deoxyinosine

<400> SEQUENCE: 2
aartcrttrc answnccdat nccnarrca                                            29

<210> SEQ ID NO 3
<211> LENGTH: 125
<212> TYPE: DNA
<213> ORGANISM: Streptomyces griseoflavus strain Tu 4072
<220> FEATURE:
<223> OTHER INFORMATION: SEQ ID 3; sia-III locus partial sequence (with
      siaA-III partial sequence); Example 1b

<400> SEQUENCE: 3
ttcccggaca ggtcacgggg ccgaaaaggt cggcccgggc cgttcgaccc acgggaggaa          60
ccatgaccgc gatctacgag ccgcccgccc tgcaggagat cggcgacttc gacgagctca         120
ccaag                                                                    125

<210> SEQ ID NO 4
<211> LENGTH: 25
<212> TYPE: DNA
<213> ORGANISM: Artificial Sequence
<220> FEATURE:
<223> OTHER INFORMATION: SEQ ID 4; primer  Examples 1c-d, 2a-b, 3b

<400> SEQUENCE: 4
ggacaggtca cggggccgaa aaggt                                                25

<210> SEQ ID NO 5
<211> LENGTH: 30
<212> TYPE: DNA
<213> ORGANISM: Artificial Sequence
<220> FEATURE:
<223> OTHER INFORMATION: SEQ ID 5; primer  Example 1c-d

<400> SEQUENCE: 5
cacgggagga accatgaccg cgatctacga                                           30
```

```
<210> SEQ ID NO 6
<211> LENGTH: 195
<212> TYPE: DNA
<213> ORGANISM: Streptomyces griseoflavus strain Tu 4072
<220> FEATURE:
<223> OTHER INFORMATION: SEQ ID 6; sia-III locus partial sequence (with
      siaA-III full sequence) Example 1c

<400> SEQUENCE: 6
ttcccggaca ggtcacgggg ccgaaaaggt cggcccgggc cgttcgaccc acgggaggaa    60
ccatgaccgc gatctacgag ccgcccgccc tgcaggagat cggcgacttc gacgagctca   120
ccaagtgcct cggcatcggg agctgcaacg acttcgccgg ctgcggttac gccgtcgtct   180
gcttctggtg atcgc                                                    195

<210> SEQ ID NO 7
<211> LENGTH: 25
<212> TYPE: DNA
<213> ORGANISM: Artificial Sequence
<220> FEATURE:
<223> OTHER INFORMATION: SEQ ID 7; primer   Examples 1e, 2a-b, 3b

<400> SEQUENCE: 7
gacccacggg aggaaccatg accgc                                          25

<210> SEQ ID NO 8
<211> LENGTH: 29
<212> TYPE: DNA
<213> ORGANISM: Artificial Sequence
<220> FEATURE:
<223> OTHER INFORMATION: SEQ ID 8; primer   Examples 1e, 2a-b

<400> SEQUENCE: 8
gcgtaaccgc agccggcgaa gtcgttgca                                      29

<210> SEQ ID NO 9
<211> LENGTH: 127
<212> TYPE: DNA
<213> ORGANISM: Streptomyces griseoflavus strain Tu 4072
<220> FEATURE:
<223> OTHER INFORMATION: SEQ ID 9; sia-III locus partial sequence (with
      siaA-III partial sequence) Example 1e

<400> SEQUENCE: 9
gacccacggg aggaaccatg accgcgatct acgagccgcc cgccctgcag gagatcggcg    60
acttcgacga gctcaccaag tgcctcggca tcgggagctg caacgacttc gccggctgcg   120
gttacgc                                                             127

<210> SEQ ID NO 10
<211> LENGTH: 388
<212> TYPE: DNA
<213> ORGANISM: Streptomyces griseoflavus strain Tu 4072
<220> FEATURE:
<223> OTHER INFORMATION: SEQ ID 10; sia-III locus partial sequence
      (with siaA-III full sequence) Example 1e

<400> SEQUENCE: 10
ccggcaccgt tcgtgggacg ggtgacggga cgcgcctgag gcatgtgccc catgcgcgtg    60
ggacatggcc cctcgtaggt tcccggacag gtcacggggc cgaaaaggtc ggcccgggcc   120
gttcgaccca cgggaggaac catgaccgcg atctacgagc cgcccgccct gcaggagatc   180
ggcgacttcg acgagctcac caagtgcctc ggcatcggga gctgcaacga cttcgccggc   240
```

```
tgcggttacg ccgtcgtctg cttctggtga tcgcaccggt gccggtgtgc ccctcgtggg    300
cacaccggca ccgcccgggg gagtgaggcg acatggaatt cacagtgctt ccggactgtc    360
ccgccggcgc cgcgctggcg gaccgggt                                       388
```

```
<210> SEQ ID NO 11
<211> LENGTH: 28
<212> TYPE: DNA
<213> ORGANISM: Artificial Sequence
<220> FEATURE:
<223> OTHER INFORMATION: SEQ ID 11;primer Example 2a-b,d

<400> SEQUENCE: 11
ccagaagcag acgacggcgt aaccgcag                                       28
```

```
<210> SEQ ID NO 12
<211> LENGTH: 31
<212> TYPE: DNA
<213> ORGANISM: Artificial Sequence
<220> FEATURE:
<223> OTHER INFORMATION: SEQ ID 12;primer  Example 2a-b,d

<400> SEQUENCE: 12
gcgaagtcgt tgcagctccc gatgccgagg c                                   31
```

```
<210> SEQ ID NO 13
<211> LENGTH: 73
<212> TYPE: DNA
<213> ORGANISM: Streptomyces sp. strain SKH-2344
<220> FEATURE:
<223> OTHER INFORMATION: SEQ ID 13; sia-I locus partial sequence (with
      siaA-I partial sequence) Exmaple 2b

<400> SEQUENCE: 13
gatctacgag cccccatgc tccaggaagt cggcgacttc gaggagctca cgaagtgcct    60
cggcgtcgga agc                                                       73
```

```
<210> SEQ ID NO 14
<211> LENGTH: 27
<212> TYPE: DNA
<213> ORGANISM: Artificial Sequence
<220> FEATURE:
<223> OTHER INFORMATION: SEQ ID 14; primer  Example 1b, d

<400> SEQUENCE: 14
gctcacgaag tgcctcggcg tcggaag                                        27
```

```
<210> SEQ ID NO 15
<211> LENGTH: 29
<212> TYPE: DNA
<213> ORGANISM: Artificial Sequence
<220> FEATURE:
<223> OTHER INFORMATION: SEQ ID 15; primer  Example 2b,d

<400> SEQUENCE: 15
ctacgagccc cccatgctcc aggaagtcg                                      29
```

```
<210> SEQ ID NO 16
<211> LENGTH: 27
<212> TYPE: DNA
<213> ORGANISM: Artificial Sequence
<220> FEATURE:
<223> OTHER INFORMATION: SEQ ID 16; primer  Example 2b,d

<400> SEQUENCE: 16
gagggcggcg acggtccagg cgagcag                                        27
```

<210> SEQ ID NO 17
<211> LENGTH: 27
<212> TYPE: DNA
<213> ORGANISM: Artificial Sequence
<220> FEATURE:
<223> OTHER INFORMATION: SEQ ID 17; primer  Example 2b,d

<400> SEQUENCE: 17
gcagttgtcc catgccggtc ctgtcag                                        27

<210> SEQ ID NO 18
<211> LENGTH: 28
<212> TYPE: DNA
<213> ORGANISM: Artificial Sequence
<220> FEATURE:
<223> OTHER INFORMATION: SEQ ID 18; primer  Example 2b,d

<400> SEQUENCE: 18
gtgccggtgc gttcacgcgc accggcac                                       28

<210> SEQ ID NO 19
<211> LENGTH: 27
<212> TYPE: DNA
<213> ORGANISM: Artificial Sequence
<220> FEATURE:
<223> OTHER INFORMATION: SEQ ID 19; primer Example 2b,d

<400> SEQUENCE: 19
tcgccggctg cggctacgcg atcgtct                                        27

<210> SEQ ID NO 20
<211> LENGTH: 477
<212> TYPE: DNA
<213> ORGANISM: Streptomyces sp. strain SKH-2344
<220> FEATURE:
<223> OTHER INFORMATION: SEQ ID 20; sia-I locus partial sequence (with
      siaA-full sequence) Example 2b

<400> SEQUENCE: 20
acttccccga ccaggcggga aacgaactgc tcaccgtccg gtccccgcac acggccttcg    60
gcttcacggt gctgctcgcc tggaccgtcg ccgccctcgg atggggctgg gtgcgccagc   120
gccggtggga cagctgacag gaccggcatg ggacaactgc cccatgccgg tgggacagtc   180
cgccccgtag cttccgtgac agatcacagg ccgaacaagg tcggcctgac cgatccgaaa   240
cgggaggaca ccatgtccgc gatctacgag ccccccatgc tccaggaagt cggcgacttc   300
gaggagctca cgaagtgcct cggcgtcgga agctgcaacg acttcgccgg ctgcggctac   360
gcgatcgtct gcttctggtg atcacgtccg gtgccggtgc gttcacgcgc accggcacca   420
cccggggtga cgaggagacg gggaacgagg cgacatggaa ttcgtggttc ttccgga      477

<210> SEQ ID NO 21
<211> LENGTH: 27
<212> TYPE: DNA
<213> ORGANISM: Artificial Sequence
<220> FEATURE:
<223> OTHER INFORMATION: SEQ ID 21; primer  Example 2c

<400> SEQUENCE: 21
gcttccgacg ccgaggcact tcgtgag                                        27

<210> SEQ ID NO 22
<211> LENGTH: 30
<212> TYPE: DNA

```
<213> ORGANISM: Artificial Sequence
<220> FEATURE:
<223> OTHER INFORMATION: SEQ ID 22; primer Example 2c

<400> SEQUENCE: 22
cgtgagctcc tcgaagtcgc cgacttcctg                                    30

<210> SEQ ID NO 23
<211> LENGTH: 25
<212> TYPE: DNA
<213> ORGANISM: Artificial Sequence
<220> FEATURE:
<223> OTHER INFORMATION: SEQ ID 23; primer Example 3b

<400> SEQUENCE: 23
acccggtccg ccagcgcggc gccgg                                         25

<210> SEQ ID NO 24
<211> LENGTH: 26
<212> TYPE: DNA
<213> ORGANISM: Artificial Sequence
<220> FEATURE:
<223> OTHER INFORMATION: SEQ ID 24; primer  Example 3b

<400> SEQUENCE: 24
gccagcgcgg cgccggcggg acagtc                                        26

<210> SEQ ID NO 25
<211> LENGTH: 10500
<212> TYPE: DNA
<213> ORGANISM: Streptomyces griseoflavus strain Tu 4072
<220> FEATURE:
<223> OTHER INFORMATION: SEQ ID 25; sia-III locus full sequence
      Example 3b-c

<400> SEQUENCE: 25
cccctccggc ggacggaaag cgctgctcgt agccggtacg gccacctccg gaggcgaggg    60
ttccgccccg cctccggggg cggtacgaag cacccccgga aactgtgtag acttaccgac   120
gtcgctgatc gcaccatggt gcacacggcg cgccgcctta gctcagatgg ccagagcaac   180
gcactcgtaa tgcgtaggtc tcgggttcga atcccgaagg cggctcttct tcaagccccg   240
cgcagacagt gtctgagcgg ggcttttctg ttccggtgct gctcacgccc cgttccggac   300
cagttccccg gcgggctcgc cgaagcccgc gtcccgggcc atcaccaccg ccgtcgcccg   360
gtcgtgcacc tcgagcttgg cgaagatgcg cgagacgtag ttgcggacgg tcttctcggc   420
caggaagagc cggcgggcga tctgccggtt ccccatcccg ccggccagga gctccagtat   480
ctccagctcg cggctggtga gcccggggaa cccggcgccg tcgtgcaggc cctgcatggc   540
ggagaagtag cggctcatgc gggccgcgac gctggggcag aaggcggcgc cgccccgggc   600
gacgaccttc agggagcgga gcagttcgtc ggccgaaccg aggcgggaga ggtagccgtt   660
gacacccgcg cggagggccg agacgatcat ctcgtcgtcg tcgttctgcg ccaccacgat   720
cgtgtgcggc cgggacgcct cgtcgggaa ggcggaggcg atgtgccgga cgcgtgcgga   780
gacggttctg ctggaggacg gttcgctgag gacgaccacg tcggggtgga gggcggtgcc   840
ggccaggtcc gacagacgtc ggaggtcgtc cgagtcgtcc gtggcacggc cgacaagagc   900
gcactcctca tcctgatcga caatcgcttc gagcccggcc agggacaccg cgttgtcgct   960
gaccacgaac aggttgacgg tcatctcgta catcccccag aaatgcgtcg acgtggtgcg  1020
gacggcgccg gaaggtcccc gggggcacac gcgacgaagg tcggtccgt aggcgaccga  1080 ctccgggcgt gacgtggtca gttgtggttt tcagcggccc ccgtggccat gacctgtcgg  1140
```

```
cgcaggcatg gtggtgcatc gaaagcgcgc aaggcgctcg tggtgccgag tatgtggacg   1200
cgtccggaga gaacgcaagg tcgccaacgc acccgtgttg tccgaggggt gagtatcggc   1260
cggaccccgc cgaaccaccg cgattccggc gtcggaggtg gtgggggcgg ctccgggcgc   1320
gcgacccgca ggaccgcgcg ccggtgtggg ccgtggtgcg gggcggacga cactgtccga   1380
aacggtcacc gcccgcgcg acacgcggac gtccggccct cgcccgttg acgggccgc     1440 ggagcgagcg cttacgttcg acggcatggg tgaggggtcc cggaggcgtg cgatcgtgct   1500
ggacgcggcg gcggcctgcg cgttcacgct cctgccgcag gtgtcgctgc tgcggccggc   1560
cgtcgacggc gggacgggcg gcggcctcct gtggctgctg tccctggccg ccggactccc   1620
gctcgccgta aggcggttgt ggcccgtccc ggtcttcgtc ctcgtcctgg ccgccgcctg   1680
cggggcgctg gccgccggcc tcggacccgc ctcgttcctg gccgccgcct acgccgtcca   1740
cacggtggcc accacccggc ggcgcgaccc cggggtgtcg gccgtcgccg tcgccgggct   1800
gtgcgcggcg gtcgccgccc tcctcacgct gtcgggcggg cagtcctacc agggtggcag   1860
caccgccgtg caggccgtgt tcggcctcct cgtgctcggc gcgacctggg cggccggctc   1920
ggcggtcagg gagcgcagac gcagtacccg gcgcgccatc gagcacgccg ccgagcaggc   1980
gaagaccgag gagcgcctgc gcatcgcccg cgacatccac gacgtcgtca cccacagcgt   2040
gggactcatc gccgtcaagg ccggcatcgc caaccacgtg gtggccaccc gccccgagga   2100
ggccaaggag gccctggcgg tcattgagga cgtcagccgc cgggcgctgc gcgacatgcg   2160
cgccaccctg accgtgctgc gcggtgagga ccggagcgag gccggggacc tgcggcccgc   2220
ccgcggcctc gcggacctgc ccgcgctgct cgagaccgcc gaggcggcag gcgtccgcgt   2280
cgaactgcgc acccgctacg accaggaacc gcccgagggt gtcgcgctgg cggcgttccg   2340
catcgtccag gagtccctca ccaacgtgct caagcacgcc gcgccgaccg gctgccgggt   2400
ggacgtcacg gcgcggcagg gcgtgctgac ggtggacgtg accgacgacg gccccggccc   2460
cggacgccgg accacggtgc ccggcggcgg gatgggctg gtcggcatga aggagcgggc   2520
cgccgcgcac ggcggcaccc tcgccgccgg cccccgcccc ggcggcggct tccgggtgac   2580 ggccacccctg ccgttctagg acctgacgga cgccggctca tcctcgggta tgaggggcgc   2640
ccgcgcggca ccgcgccggg ttcccgaccg cgggccgatg cggtcgcggg gtgtgcgccg   2700
cgagactcga cacgtgatgc ttgccgagag actgaccaag cggtacgggc ccgccaccgt   2760
cgtcgacgac ctgtccttca cggtgcgacc aggtgtcgtc accggcttcc tcgggcccaa   2820
cggcgccggg aagtccacga cgatgcggat gatgctcggc ctgacccgcc cgacggcgg   2880 cacgccacc gtcggcggac gcgcctaccg cgacctgacc tacccgctcc ggcacgtcgg   2940
cgcgctcctg gagacgtcgg ccccgcaccg tggcatgacc gccgtcggcc atctgtcgtg   3000
gctggcgcgc agcaaccgcg ttccccgccg gcgggtggac gaggtgctcg acgcggtcgg   3060
tctcacggaa gccgcccgta aacgggtcgg caccttctcc ctgggcatgg acagcgcct   3120 cggcctggcg gctgccctcc tcggcgaccc cccggtcctg gtgctcgacg agccggtcaa   3180
cgggctcgac gccgagggca tccggtggct gcgcgaactg ctgcgcgcca aggcagccga   3240
gggccgcacc atcctcgtct ccagccatct gatggcggag atggcgcagg tcgccgacga   3300
gctgatcgtg atcagccggg gccggctcct cgccgagacc agcgtgtcgg agttcctcgg   3360
acgccacggc cggacgttcg tacgggtccg gacctccgaa ccgctgcggg ccgcgcagga   3420
gttccaggcg aagggcgcca cctcggtgcg gcggccgcg gacggcggcc tggaggtgga   3480
cggcctgccg gcgggcgagg tgaaccgcat cgccgcggcg gccggtgtcc ccgtcgagga   3540
```

```
actgagcacc cacaccggct cgctggagga gaccttcctc aagctcgtcg acgacggagg    3600
agatcccacg catgtctgag accctcgcgg ccgcgcgggc ggagttcacc aagatgcggg    3660
cggtgcgcgc cacgtccgtc gcactgctgc tgttcgtcgc cgtcagcgtg ttcatcgccg    3720
cactgggcgg ctggtccgcc aagggcgcga tcgagtccgg caatcccggg ctgcgctccg    3780
acttcacgcc cgagcaggcc ggcctggacg gcatcctcta cggccagctc gccctgatcg    3840
tgttcggggt gctgatgatg tccggcgagt acacctcggg catgatgcgg gtctcgctgc    3900
tcgcggtgcc ccggcgggc cggctctacc tggccaagac ggccgtcacc gccgtcgcgg    3960
ccctggccgt cgcccttccg gtcacggtcg tgtcgtacct ggtcagccaa ctcgccctgg    4020
gcccccacgg gtcgacgctc gacgcggacg gcgtcccgcg cgccctggcc ggcgcggtcg    4080
tctacctgac cctcatgagc ctgctcgccg taggggtggc ggccgccgcc cgcagtgccg    4140
tcctcccgct ggccgtgctg ctgccgctgg tgctggtcgg ctcgcagatc ctgtccgtca    4200
tcggggcgac caaggaggtg gcgcgctggt tccccgaccg ggccggcgcc cagatgctca    4260
ccgtcgactc cggcgacgcc ctcaccggcc tcgtcgtgct gctcgcgtgg accgcggccg    4320
ccctgacggc cggctggctc cggcaccgtt cgtgggacgg gtgacgggac gcgcctgagg    4380
catgtgcccc atgcgcgtgg gacatggccc ctcgtaggtt cccggacagg tcacggggcc    4440
gaaaaggtcg gccgggccg ttcgacccac gggaggaacc atgaccgcga tctacgagcc    4500
gcccgccctg caggagatcg gcgacttcga cgagctcacc aagtgcctcg gcatcgggag    4560
ctgcaacgac ttcgccggct gcggttacgc cgtcgtctgc ttctggtgat cgcaccggtg    4620
ccggtgtgcc cctcgtgggc acaccggcac cgcccggggg agtgaggcga catggaattc    4680
acagtgcttc cggactgtcc cgccggcgcc gcgctggcgg accgggtggc ggcaccgaag    4740
cggatcgacc acgcgtcggg acggccctgg atcgtggggg actggcccga gggcgggacg    4800
acggtgaccg aggccggcac ccgccgcctg gcggtgttcg acacacccg gcccgacgac    4860 gcgggaacgg cctccgcgct cggccggatg cgctcgctgc acgacgtcga ccgggtcgcg    4920
tcccggctgc ccgggtctt ccacctcgcg gcctccctgg acggcgcggt ccgcctccag    4980
ggctccgtgg ccggcgtacg gcaggtcttc accgcccggg tcgacggggt gacggtcgcc    5040
gcgagcgccg tggacccgct gctgcgcctc accggcgcgg gactcgacga gaccctgctg    5100
gccgcgcggc tgctggcgcc cggcggggcg ccctggccgc tctcgccgcg cccggtccgc    5160
cgcggcgtgg acgcgctgcc caccggccac tggctggagc tcggcgccga cggccgggcc    5220
cgcagcgtcc gttggtggga actgcccgag gcgaccctct cgctggagga gggtgccggg    5280
gccgtccgtt ccgcgctcac cgacgccctc gcgaccccgtg tggacccgca ccgcacggtc    5340
agcgcggacc tctccggcgg actcgactcg accaccctgt gcttcctcgc cgacgcggcc    5400
ggcgccgacc tggtcaccta ccacgtcatg ccgctcgacg aggccaacga ggacaccgca    5460
tgggcccgca aggccgccgc gcatctgccg cacgcccgcc accacatgct cgccgcggac    5520
cgcgccgcca acctgttcga catcggctac accgccgaca ccctcaacgc ggcccccgag    5580
ggcccctcga cgtgggcctc cggactgcgc acatccgggg acctcgccgg gcgggccacc    5640
gccgaggggg cggccctgca cctgtccggg ttcggcgggg acgaactctt cggccggatg    5700
cccgcctgcg cctggtccct cgcccgcctc gcccgccgcg acggcctgcg gctggtgaac    5760
cgctaccggc tggccaaccg ctggccctgg cgcagcaccc tgcggcagct cgcggaccgt    5820
tcgacgttcg cgcagaacct gaccgaggtc gccgggcgga tcaccgcccc gccccgccg    5880 gtcaacgagc cggacttcgg ctgggtgttc gcgccgcgca tgcccgcctg gccaccccg     5940
```

```
gacgcggtgg ccgccgtgcg ggacctgctg accacggcag ccgaacggac cccggaaccg    6000
ctggacgccg accgggcccg gcaccaggcg ctgtcctcca tcgtgttcga ggggaacacc    6060
gtccggcagg tcaacaccgc cgtcgccggc accggcctgg tctgggaggc gccgttcctc    6120
gacgaccggg ttctcgaggc ggccttcgcc acccggatcg acgagcggct ggccgccgga    6180
cggttcaagc cgctgctgac caccgccgtg cggggcctcg tgcccgacga cttcctcgcc    6240
cgtcgcgaca agggagagtt cagcgccgag acgttccggg gcatcgaacg caaccgggac    6300
cggatcctgg acctctgcga ggactcgctc ctggcccggc tcggcctcgt cgacccgcac    6360
gccttccggt ccgcggtgct caaccccggg ccgatgtccc atcacctcca gccgatccag    6420
accacggtgg cgtgcgagag ctggctgcgg gcgcaccccc aggacaccgg agagaaccga    6480
tgaaactgag tcttgcccgc gacgtcaccc tcacgcccgt cgattccggg gcggtcctgc    6540 tcgacgccg ccgcgacgc tactaccagc tgaacgcctc cggctccgcg atcctgcaca    6600
agctgctcga cggcgacact cccgccgcgg ccgccgcgag cctgtcggag tccgcccccg    6660
tcagcgagga gcgggtgcac caggacgtgc tggccctggt ccgctcgctg agcgaggccg    6720
acctcgtgga ggtgacacag tgaccacgcc cgccgtcgcc gaacaggcca cgcgcctccc    6780
gctgcaccgg cagatcgccc ccagatgcgc ggccggcgcc gcccgtctgc tggtcaggct    6840
gcccccggcc cggctgcacc gggtgctgcg cgtcctgagc aagggttccc ggcccgccgg    6900
atacgcccag gtggcgcggg cccggcggtc cgtcgtctcg gtcagcaccc gctgcgcggg    6960
cctcggctgc ctccagcggt ccgtcgccac cgtgctgctg ctccgcgtcc ggggcaggtg    7020
ggccgactgg tgcaccggct tccgggtgca gcccttcgcc gcgcacgcct gggtcgaggc    7080
cggcggccgc ccgtcgacg agcccggaga ggtcggcgtg ttccgcaccg tgctggccgt    7140
gcgccgcacc ggaggcggct catgacggcg atccgggccg agggcctcta cgcgtactac    7200
ggcaccacgc cggccgtgaa cggcctccac ctgaacgtcc ccgaggggc caccttcggg    7260 ttcctggggc cgaacggcgc cggcaagacc accaccatca gcatgctcac cacgctgctc    7320
aggcccacgg cgggccgcgc ggaggtggcc gggttcgacg tcaccacgca cgccgccgag    7380
gtgcggcgca ggatcggcat cgtcttccag gagtcgacgc tcgacctgga actcacggcg    7440
accgagaacc tgcgattcca ggccgacctg tgcggtctgg gccgggccga ggcgcgcgcc    7500
gcggtggccg cgatgctcga catgatggag ctgacgggac gcgacaggac ccccgtgcgg    7560
cacttctcca ccggcctgcg ccgacgcctg gagatcgccc gcggcctgct cggctccccg    7620
cgcgtgctct tcctcgacga gccgaccacc ggcctcgaca cgcagacccg tgcggccgtc    7680
tggcaccacc tggaccggct ccgcgaggag cagggcatca cggtcttctt caccacgcac    7740
cagctggagg aggccgagca ctgcgaccgc atcgcgatct tcgaccgcgg caagctggtc    7800
acggagggct cacccgcgga gctgaagtcc gtcatcgggg ccgacgtcgt cgacctgcgc    7860
accgatgacg accggctggc cgtggacctg ctgtccgacc gcttcggcct gacggccgag    7920
aacacccccg cgcggactgcg gctgagggtg caggacggcg cctccatggt gccccgcctg    7980 tgcacgggc tgggcctggg cgtgcggtcg gtgaccgtca ccccgccctc gctcgacgac    8040
gtctacctgc accacaccgg gaccgcgatc agggacagcg ggtccgacgc ccgctcgctc    8100
gacagcctcg ggagggact gcgatgaccc ggaccgacat cccgccgagc gtcaccgtga    8160
cgaaaccggc cccgccctcg tccgaggggc ggacctggca caccgtacgg ccctacgcgc    8220
tgctgtggcg gcgtgagatg acccggctgc ggcacaatcc gctgcgcctc gtcatgggtc    8280
tggtcacccc gctgctgttc ctcgtcgtgc tgggcacggg gctggaagcg gcgtcgtcca    8340
```

```
cgctcggcaa ggcccagcta aacgactacc gggcctacct gttcccgggc gcgctcgtga    8400
tgtccgtgca ggccccggcc atcgccgtgg gcatctcgct cgtctgggac cgccggctcg    8460
gcatgctgcg ccagatgctc gtctccccgt tccctcggtc gagcatcgtc ctcggcctcg    8520
cgctcggcgg agccaccacg ggcgccgtct acggcctcgc cctgctcgcg gtcggaggca    8580
tcgcgggcgt ccggtacacg ccgatgctgc tggtcgtcct cgtcgaactg ctcctggtct    8640
ccctgctctt cacctcgttc ggccttctcg ccgcggtcac catccggcag gtcgacacct    8700
tccagatcgt ggtgaacctc agcctcatgc cgctgatgtt cttctccggc gcgatgttcc    8760
cgcccaacgg gctgccgggc tggctcgaca ccgtcgtcaa gctgaacccg ctgacctacg    8820
gcgtcgacgc cgtgcgccgg acactgcccg gccccgacgt cctcacctcg gagcagaccc    8880
ggctgatgct cggcgactgg aacccgcccg tgtacgcgga actcggcgtg ctggccgccc    8940
tcaccgccgc cgtactgggc ctcgccacct accggttctc ccgggcgcag tgaaagggg    9000
ccggccgtga cgttcgtgcg gacatgggcg ggcaccgcgg ccaggatcgt cctcgcggcg    9060
gtcctgggct acgcgggctg ggtgaaggtc caggacctca cgggagccgg ccgtaccgtc    9120
gccctctacc agctcgtccc cgaggaaagc gcacaactcg tcggcgccgc cgtggcgttc    9180
gtcgaactgg cgcttgccct gctgcttctc gccgggctcg ccacccgcgc cgtggcggcc    9240
gtcaccgccc tgctgatggt cacgtacatc gcggccatcg cctcggtgtg ggcgcgcggg    9300
atgtccatcg actgcggctg cttcagcagc ggcggcaccc tcaccggcgg cgcggaacgg    9360
ggctacgtcc tcgacatcgc gcgcgacctc gccttcctcg gcgccgccgc gttcctgatc    9420
acccgcccgc ggacccgtta cgccctggac cgctgggtcc tggaaacgaa ggagcgatag    9480
acatgcagcc gtcgacggac gcccaggtcc gggaaatggt ccaccggcgc cggcgacgcc    9540
gccgcactgt gctggtgtcg ctcgcggcgg tggtcacggt gctcggcgcc gcgctcgtcg    9600
gcgccggcct ggtccgggcc accgacaccg agcccggcga tgcgcccgag gaggtgcccg    9660
ccggtgtggc cgccgaccgg gccggactcg tcacgtccga gggtccggtc cgtgtcgacc    9720
tctacctcga ctacctctgc cccgagtgcc gcatcaccga aaggccctc gcgcccgaac    9780
tgagggagat gcaggaacgc ggagaggtgc gcgtcgtcca ccacccggtc gccttcctcg    9840
acgaccgcag cgcccccgcc ggctactcca cccgggccgc gtccgccgcc gctgcgccg    9900
ctgaccggaa caagttcgag ccctacacgg cggcgctctt cgacgagcag ccgccggagc    9960
agggccccgg cctcgacacc gaccgcctgg tcgcccctcgg ccgggacgtc ggcatcaccg    10020
gcgcgtcctt cgagcggtgc gtccgcgacg gcacgtaccg gccctgggtg acgtacgtgt    10080
ccgaggtcgc cgcctcccgc ggggtggccc tcacccccgac cgtgaaggtg gccggcaagc    10140
gcgtggacct ctccggaccc gaccgggcga aggcgttcgt gcgagcggtg gaggagagcc    10200
gttcatgagc cgcctcaccg tggcgctgac cggggactgc atgatgacgc ggggcgcgcc    10260
cgtcacctcc gaccccgccg ccggccgact gggcgaggtg ctgcacacgg ccgacttcgc    10320
cttcaccaac ctggaggtcg cgcccgccac cggacgcggc caccccgtac ccgacgcggc    10380
cagcggaggc ggcctgatcg cggaccccgc cgtcctcgac gacgtgacgg ggatgggctt    10440
ctccgccctg agctgcgcca acaaccatgc cctcgacctg gcacggagg gcgtcctcgg    10500
```

<210> SEQ ID NO 26
<211> LENGTH: 129
<212> TYPE: DNA
<213> ORGANISM: Streptomyces griseoflavus strain Tu 4072
<220> FEATURE:
<223> OTHER INFORMATION: SEQ ID 26; siaA-III full sequence Example 3b-c

<400> SEQUENCE: 26

```
atgaccgcga tctacgagcc gcccgccctg caggagatcg gcgacttcga cgagctcacc    60
aagtgcctcg gcatcgggag ctgcaacgac ttcgccggct gcggttacgc cgtcgtctgc   120
ttctggtga                                                           129
```

<210> SEQ ID NO 27
<211> LENGTH: 1812
<212> TYPE: DNA
<213> ORGANISM: Streptomyces griseoflavus strain Tu 4072
<220> FEATURE:
<223> OTHER INFORMATION: SEQ ID 27; siaB-III full sequence  Example 3b-c

<400> SEQUENCE: 27

```
atggaattca cagtgcttcc ggactgtccc gccggcgccg cgctggcgga ccgggtggcg    60
gcaccgaagc ggatcgacca cgcgtcggga cggccctgga tcgtgggga ctggcccgag   120
ggcgggacga cggtgaccga ggccggcacc cgccgcctgg cggtgttcgg acacacccgg   180
ccgacgacg cgggaacggc ctccgcgctc ggccggatgc gctcgctgca cgacgtcgac   240
cgggtcgcgt cccggctgcc cggggtcttc cacctcgcgg cctccctgga cggcgcggtc   300
cgcctccagg gctccgtggc cggcgtacgg caggtcttca ccgcccgggt cgacggggtg   360
acggtcgccg cgagcgccgt ggacccgctg ctgcgcctca ccggcgcggg actcgacgag   420
accctgctgg ccgcgcggct gctggcgccc ggcggggcgc cctggccgct ctcgccgcgc   480
ccggtccgcc gcggcgtgga cgcgctgccc accggccact ggctggagct cggcgccgac   540
ggccgggccc gcagcgtccg ttggtgggaa ctgcccgagg cgaccctctc gctggaggag   600
ggtgccgggg ccgtccgttc cgcgctcacc gacgccctcg cgaccgtgt ggacccgcac   660
cgcacggtca gcgcggacct ctccggcgga ctcgactcga ccaccctgtg cttcctcgcc   720
gacgcggccg cgccgaccct ggtcacctac acgtcatgc cgctcgacga ggccaacgag   780
gacaccgcat gggcccgcaa ggccgccgcg catctgccgc acgcccgcca ccacatgctc   840
gccgcggacc cgccgccaa cctgttcgac atcggctaca ccgccgacac cctcaacgcg   900
gccccgagg gcccctcgac gtgggcctcc ggactcgcgc acatccggga cctcgccggg   960
cgggccaccg ccgagggggc ggccctgcac ctgtccgggt cggcggggga cgaactcttc  1020
ggccggatgc ccgcctgcgc ctggtccctc gcccgcctcc gccggccga cggcctgcgg  1080
ctggtgaacc gctaccggct ggccaaccgc tgggcctggc gcagcaccct gcggcagctc  1140
gcggaccgtt cgacgttcgc gcagaacctg accgaggtcg ccgggcggat caccgccccg  1200
ccccgccgg tcaacgagcc ggacttcggc tgggtgttcg cgccgcgcat gcccgcctgg  1260
gccaccccgg acgcggtggc cgccgtgcgg gacctgctga ccacggcagc cgaacggacc  1320
ccggaaccgc tggacgccga ccgggcccgg caccaggcgc tgtcctccat cgtgttcgag  1380
gggaacaccg tccggcaggt caacaccgcc gtcgccggca ccggcctggt ctgggaggcg  1440
ccgttcctcg acgaccgggt tctcgaggcg gccttcgcca ccggatcga cgagcggctg  1500
gccgccggac ggttcaagcc gctgctgacc accgccgtgc ggggcctcgt gcccgacgac  1560
ttcctcgccc gtcgcgacaa gggagagttc agccgcgaga cgttccgggg catcgaacgc  1620
aaccgggacc ggatcctgga cctctgcgag gactcgctcc tggcccggct cggcctcgtc  1680
gacccgcacg ccttccggtc cgcggtgctc aaccccgggc cgatgtccca tcacctccag  1740
ccgatccaga ccacggtggc gtgcgagagc tggctgcggg cgcaccccca ggacaccgga  1800
gagaaccgat ga                                                     1812
```

<210> SEQ ID NO 28
<211> LENGTH: 264
<212> TYPE: DNA
<213> ORGANISM: Artificial Sequence
<220> FEATURE:
<223> OTHER INFORMATION: SEQ ID 28; siaC-III full sequence   Example 3b-c

<400> SEQUENCE: 28

| | | | | | |
|---|---|---|---|---|---|
| atgaaactga | gtcttgcccg | cgacgtcacc | ctcacgcccg | tcgattccgg | ggcggtcctg | 60 |
| ctcgacggcc | gccgcggacg | ctactaccag | ctgaacgcct | ccggctccgc | gatcctgcac | 120 |
| aagctgctcg | acggcgacac | tcccgccgcg | gccgccgcga | gcctgtcgga | gtccgccccc | 180 |
| gtcagcgagg | agcgggtgca | ccaggacgtg | ctggccctgg | tccgctcgct | gagcgaggcc | 240 |
| gacctcgtgg | aggtgacaca | atga | | | | 264 |

<210> SEQ ID NO 29
<211> LENGTH: 426
<212> TYPE: DNA
<213> ORGANISM: Artificial Sequence
<220> FEATURE:
<223> OTHER INFORMATION: SEQ ID 29; siaD-III full sequence   Example 3b-c

<400> SEQUENCE: 29

| | | | | | |
|---|---|---|---|---|---|
| gtgaccacgc | cgccgtcgc | cgaacaggcc | acgcgcctcc | cgctgcaccg | gcagatcgcc | 60 |
| cccagatgcg | cggccggcgc | cgcccgtctg | ctggtcaggc | tgcccccggc | ccggctgcac | 120 |
| cgggtgctgc | gcgtcctgag | caagggttcc | cggcccgccg | gatacgccca | ggtggcgcgg | 180 |
| gcccggcggt | ccgtcgtctc | ggtcagcacc | cgctgcgcgg | gcctcggctg | cctccagcgg | 240 |
| tccgtcgcca | ccgtgctgct | gctccgcgtc | cggggcaggt | gggccgactg | gtgcaccggc | 300 |
| ttccgggtgc | agcccttcgc | cgcgcacgcc | tgggtcgagg | ccggcggccg | cccggtcgac | 360 |
| gagcccggag | aggtcggcgt | gttccgcacc | gtgctggccg | tgcgccgcac | cggaggcggc | 420 |
| tcatga | | | | | | 426 |

<210> SEQ ID NO 30
<211> LENGTH: 966
<212> TYPE: DNA
<213> ORGANISM: Streptomyces griseoflavus strain Tu 4072
<220> FEATURE:
<223> OTHER INFORMATION: SEQ ID 30; siaE-III full sequence   Example 3b-c

<400> SEQUENCE: 30

| | | | | | |
|---|---|---|---|---|---|
| atgacggcga | tccgggccga | gggcctctac | gcgtactacg | gcaccacgcc | ggccgtgaac | 60 |
| ggcctccacc | tgaacgtccc | cgaggggggcc | accttcgggt | tcctgggggcc | gaacggcgcc | 120 |
| ggcaagacca | ccaccatcag | catgctcacc | acgctgctca | ggcccacggc | gggccgcgcg | 180 |
| gaggtggccg | ggttcgacgt | caccacgcac | gccgccgagg | tgcggcgcag | gatcggcatc | 240 |
| gtcttccagg | agtcgacgct | cgacctggaa | ctcacggcga | ccgagaacct | gcgattccag | 300 |
| gccgacctgt | gcgtctgggc | cggggccgag | gcgcgcgccg | cggtggccgc | gatgctcgac | 360 |
| atgatggagc | tgacgggacg | cgacaggacc | cccgtgcggc | acttctccac | cggcctgcgc | 420 |
| cgacgcctgg | agatcgcccg | cggcctgctc | ggctccccgc | gcgtgctctt | cctcgacgag | 480 |
| ccgaccaccg | gcctcgacac | gcagaccccgt | gcggccgtct | ggcaccacct | ggaccggctc | 540 |
| cgcgaggagc | agggcatcac | ggtcttcttc | accacgcacc | agctggagga | ggccgagcac | 600 |
| tgcgaccgca | tcgcgatctt | cgaccgcggc | aagctggtca | cggagggctc | acccgcggag | 660 |
| ctgaagtccg | tcatcggggc | cgacgtcgtc | gacctgcgca | ccgatgacga | ccggctggcc | 720 |

-continued

```
gtggacctgc tgtccgaccg cttcggcctg acggccgaga acaccccggg cggactgcgg    780
ctgagggtgc aggacggcgc ctccatggtg ccccgcctgt gcaccgggct gggcctgggc    840
gtgcggtcgg tgaccgtcac cccgcccctcg ctcgacgacg tctacctgca ccacaccggg    900
accgcgatca gggacagcgg gtccgacgcc cgctcgctcg acagcctcgg ggagggactg    960
cgatga                                                                966
```

<210> SEQ ID NO 31
<211> LENGTH: 870
<212> TYPE: DNA
<213> ORGANISM: Streptomyces griseoflavus strain Tu 4072
<220> FEATURE:
<223> OTHER INFORMATION: SEQ ID 31; siaF-III full sequence   Example 3b-c

<400> SEQUENCE: 31

```
atgacccgga ccgacatccc gccgagcgtc accgtgacga aaccggcccc gccctcgtcc    60
gaggggcgga cctggcacac cgtacggccc tacgcgctgc tgtggcggcg tgagatgacc    120
cggctgcggc acaatccgct gcgcctcgtc atgggtctgg tcaccccgct gctgttcctc    180
gtcgtgctgg gcacggggct ggaagcggcg tcgtccacgc tcggcaaggc ccagctaaac    240
gactaccggg cctacctgtt cccgggcgcg ctcgtgatgt ccgtgcaggc cccggccatc    300
gccgtgggca tctcgctcgt ctgggaccgc cggctcggca tgctgcgcca gatgctcgtc    360
tccccgttcc ctcggtcgag catcgtcctc ggcctcgcgc tcggcggagc caccacgggc    420
gccgtctacg gcctcgccct gctcgcggtc ggaggcatcg cggcgtccg gtacacgccg    480 atgctgctgg tcgtcctcgt cgaactgctc ctggtctccc tgctcttcac ctcgttcggc    540
cttctcgccg cggtcaccat ccggcaggtc gacaccttcc agatcgtggt gaacctcagc    600
ctcatgccgc tgatgttctt ctccggcgcg atgttcccgc caacgggct gccgggctgg    660 ctcgacaccg tcgtcaagct gaaccccgctg acctacggcg tcgacgccgt cgcgccggaca    720 ctgcccggcc ccgacgtcct cacctcggag cagacccggc tgatgctcgg cgactggaac    780
ccgcccgtgt acgcggaact cggcgtgctg gccgccctca ccgccgccgt actgggcctc    840
gccacctacc ggttctcccg ggcgcagtga                                     870
```

<210> SEQ ID NO 32
<211> LENGTH: 474
<212> TYPE: DNA
<213> ORGANISM: Streptomyces griseoflavus strain Tu 4072
<220> FEATURE:
<223> OTHER INFORMATION: SEQ ID 32; siaG-III full sequence   Example 3b-c

<400> SEQUENCE: 32

```
gtgacgttcg tgcggacatg ggcgggcacc gcggccagga tcgtcctcgc ggcggtcctg    60
ggctacgcgg gctgggtgaa ggtccaggac ctcacgggag ccggccgtac cgtcgccctc    120
taccagctcg tccccgagga aagcgcacaa ctcgtcggcg ccgccgtggc gttcgtcgaa    180
ctggcgcttg ccctgctgct tctcgccggg ctcgccaccc gcgccgtggc ggccgtcacc    240
gccctgctga tggtcacgta catcgcgcc atcgcctcgg tgtgggcgcg cgggatgtcc    300
atcgactgcg gctgcttcag cagcggcggc accctcaccg gcggcgcgga acggggctac    360
gtcgtcgaca tcgcgcgcga cctcgccttc ctcggcgccg ccgcgttcct gatcacccgc    420
ccgcggaccc gttacgccct ggaccgctgg gtcctggaaa cgaaggagcg atag          474
```

<210> SEQ ID NO 33
<211> LENGTH: 726

```
<212> TYPE: DNA
<213> ORGANISM: Streptomyces griseoflavus strain Tu 4072
<220> FEATURE:
<223> OTHER INFORMATION: SEQ ID 33; siaH-III full sequence   Example 3b-c

<400> SEQUENCE: 33
atgcagccgt cgacggacgc ccaggtccgg gaaatggtcc accggcgccg gcgacgccgc      60
cgcactgtgc tggtgtcgct cgcggcggtg gtcacggtgc tcggcgccgc gctcgtcggc     120
gccggcctgg tccgggccac cgacaccgag cccggcgatg cgcccgagga ggtgcccgcc     180
ggtgtggccg ccgaccgggc cggactcgtc acgtccgagg gtccggtccg tgtcgacctc     240
tacctcgact acctctgccc cgagtgccgc atcaccgaga aggccctcgc gcccgaactg     300
agggagatgc aggaacgcgg agaggtgcgc gtcgtccacc accggtcgc cttcctcgac     360 gaccgcagcg ccccgccgg ctactccacc cgggccgcgt ccgccgccgc ctgcgccgct     420
gaccggaaca agttcgagcc ctacacggcg gcgctcttcg acgagcagcc gccggagcag     480
ggccccggcc tcgacaccga ccgcctggtc gccctcggcc gggacgtcgg catcaccggc     540
gcgtccttcg agcggtgcgt cgcgacggc acgtaccggc cctgggtgac gtacgtgtcc     600
gaggtcgccg cctcccgcgg ggtggccctc accccgaccg tgaaggtggc cggcaagcgc     660
gtggacctct ccggacccga ccgggcgaag gcgttcgtgc gagcggtgga ggagagccgt     720
tcatga                                                                726

<210> SEQ ID NO 34
<211> LENGTH: 28
<212> TYPE: DNA
<213> ORGANISM: Artificial Sequence
<220> FEATURE:
<223> OTHER INFORMATION: SEQ ID 34; primer Example 4b

<400> SEQUENCE: 34
cgaccaggcg ggaaacgaac tgctcacc                                         28

<210> SEQ ID NO 35
<211> LENGTH: 29
<212> TYPE: DNA
<213> ORGANISM: Artificial Sequence
<220> FEATURE:
<223> OTHER INFORMATION: SEQ ID 35; primer  Example 4b

<400> SEQUENCE: 35
tccggaagaa ccacgaattc catgtcgcc                                        29

<210> SEQ ID NO 36
<211> LENGTH: 29
<212> TYPE: DNA
<213> ORGANISM: Artificial Sequence
<220> FEATURE:
<223> OTHER INFORMATION: SEQ ID 36; primer  Example 4b

<400> SEQUENCE: 36
ggtccccgca cacggccttc ggcttcacg                                        29

<210> SEQ ID NO 37
<211> LENGTH: 29
<212> TYPE: DNA
<213> ORGANISM: Artificial Sequence
<220> FEATURE:
<223> OTHER INFORMATION: SEQ ID 37; primer  Example 4b

<400> SEQUENCE: 37
tccatgtcgc ctcgttcccc gtctcctcg                                        29
```

<210> SEQ ID NO 38
<211> LENGTH: 8817
<212> TYPE: DNA
<213> ORGANISM: Streptomyces sp. strain SKH-2344
<220> FEATURE:
<223> OTHER INFORMATION: SEQ ID 38; sia-I locus full sequence
      Example 4b-c

<400> SEQUENCE: 38

| | | | | | |
|---|---|---|---|---|---|
| tccacgacgt | cgtcacccac | agcgtgggcc | tgatcgcgat | caaggccggg | gtcgccaacc | 60 |
| acgtcatcgc | cacccacccc | gaggaggccg | agaggccct | caccgtcatc | gaggacatca | 120 |
| gccgcagggc | gctgcgcgac | atgcgggcca | ccctcaaggt | gctgcgccga | aagacgacg | 180 |
| cccagcagca | ggacctccag | ccggtccccg | gactgtcgga | cctgccttcc | ctggtccgta | 240 |
| cggccgaggc | ggcgggcgtc | agcgtcgacc | tgcgctccga | ttgcgtggag | gaaccacccg | 300 |
| acggggtcgc | gctgaccgcg | ttccggatcg | tccaggaggc | gctgaccaac | gtcgtcaaac | 360 |
| acgctgcccc | gacccgctgc | ctggtcagcg | tcaccgcgca | ggacggtgtg | ctgacgatcg | 420 |
| gcgtcaccga | cgacgccccc | ggacccgggc | accggccgac | cgttcccggc | ggcgccatgg | 480 |
| ggctcatcgg | gatgagggaa | cgggccgtcg | cgcacggcgg | gaccctcacg | gcgggccccc | 540 |
| gccccggcgc | gggcttccgg | atcctcgcga | cactgccgta | ctagtgccac | gccaaccgcc | 600 |
| atacgtcccg | ccccccgcat | atggctgaaa | cggtctcata | ccccggtatg | ggtccggtcc | 660 |
| gcgaaaccgg | cccgcaccgt | cccgaccccg | gtccgatgtg | tggcgcggcc | gccgcgggcc | 720 |
| agactcgtcg | cgtgattgac | gtccagaacc | tgaccaagcg | gtacgggccg | gccaccgtcg | 780 |
| tggacggcct | gaccttcacg | gtgcggcccg | gagccgtcac | cggcttcctc | ggccccaacg | 840 |
| gcgccgggaa | gtcgaccacc | ctgcggatga | tgctgggcct | gacccgcccc | gacaccggaa | 900 |
| ccgcgcggat | cgacgggcac | gcctacggcg | acctggccca | cccccctccgc | cgcatcggcg | 960 |
| ccctgctgga | gacctcggcc | ccgcaccgcg | gcctgaccgc | gcgcgaccat | ctgctctggc | 1020 |
| tcgcccagag | caaccggatc | gcccgcggcc | gggtcgccga | ggtcctggag | gcggtcggac | 1080 |
| tcgcggacgc | ggcccggcgc | cggaccggca | ccttctccct | cggcatgggc | cagcggctgg | 1140 |
| gcctggccgc | cgcgctcctc | ggcgaccccg | ccgtgctggt | gctcgacgaa | ccggtcaacg | 1200 |
| gcctggacac | cgagggcatc | cgctggctgc | gcgacctgct | cgcgtcgatg | gccgccgagg | 1260 |
| gccgtaccgt | cctcatctcc | agccatctga | tgaccgagat | ggccctggtc | gccgatcacc | 1320 |
| tggtcgtcat | cagccggggc | cggctcctcg | cggacaccgg | gatgtcggac | ttcatcgagc | 1380 |
| gccacggacg | gtcgtacgtc | cgggtccgca | ccgccgaacc | cgaccggctc | ggcagggagt | 1440 |
| tggaaggccg | cggcgccacg | gtgagccgcg | tccccggcgg | cggcctggac | gtcgtgggca | 1500 |
| tgacggccgc | ggacgtcagc | cggatcgccg | cggcgggcgg | cttcccgctc | gacgaactcg | 1560 |
| ccacccacgc | cgggtcgttg | gaggagacct | tcctcgacgt | cgtcggagag | ggccaacagg | 1620 |
| tccacggtcc | ggaaggcagg | aacacccatg | tctgagaccc | tcgcggccgt | ccgcgccgag | 1680 |
| accaccaagc | tgcgcggcat | tcgcggcacc | cggatctcgc | tgctgctgtt | cgccgcggtc | 1740 |
| agcgtcctca | tcgccgccct | cgacggctgg | tccgcgaaga | acgcgctgga | gtccgacaac | 1800 |
| cccagcctgc | gttccgactt | cacccccgaa | caggccggtc | tcgacggcat | cctctacggc | 1860 |
| cagttggcgc | tgatcgtgtt | cggcgtcctc | gtcgtcacca | gcgagtacac | gtccggcatg | 1920 |
| atccgtgtct | ccctgctcgc | cgtccccgg | gcgggacggc | tctacgcggc | gaagacggtc | 1980 |
| gtcaccgccc | tggcggcggt | ggccgtctcc | gtccccgtca | ccgtcctcgg | ctacctggtc | 2040 |

```
acgcaggcgg ctctcgggtc ccacggttcc tcgctcggcg cgagcggtgt cccgcgcgcc    2100
ctggccgggg cggtcgtcta tctgaccctg atgtgcctgt tcgcggcggg tatcgcggcg    2160
atcgcccgca acgccgtcgt accactggcc gttctgctgc cgatggtgct cgccgggacg    2220
cacatcctgt ccctcatcgg ggcgaccaag gagatggccc gatacttccc cgaccaggcg    2280
ggaaacgaac tgctcaccgt ccggtccccg cacacggcct tcggcttcac ggtgctgctc    2340
gcctggaccg tcgccgccct cggatggggc tgggtgcgcc agcgccggtg ggacagctga    2400
caggaccggc atgggacaac tgcccatgc cggtgggaca gtccgccccg tagcttccgt     2460
gacagatcac aggccgaaca aggtcggcct gaccgatccg aaacgggagg acaccatgtc    2520
cgcgatctac gagcccccca tgctccagga agtcggcgac ttcgaggagc tcacgaagtg    2580
cctcggcgtc ggaagctgca acgacttcgc cggctgcggc tacgcgatcg tctgcttctg    2640
gtgatcacgt ccggtgccgg tgcgttcacg cgcaccggca ccacccgggg tgacgaggag    2700
acggggaacg aggcgacatg gaattcgtgg ttcttccgga ctgcccggcc ggtgccgcgg    2760
ccgtcggccg gctgcgggcg acgcggcgcg tcgaccacgc gtcggggcgg ccctggatcg    2820
tcggcgactg gcccgaggcc gaggccgtcg tcgtcgaggc gggcccacgg cggatggtcg    2880
tactgggaca caccggctc gacgagaccg ccgcggcggc cgcgctcggc cggctgcgct     2940
cgctgcacga cgtggactcg atcgcgtccc ggctgccggg agccgtccac ctggcggtgt    3000
cactggacgg caggaccagg gtgcagggtt cggccgtcgg cgtacgacag atcttcaccg    3060
ccgtcgtcga cggggtgacc gtcgccgcga gcggggtgga accctgctg cggctgaccg     3120 gcgccggcct cgacgagacc gtgctcgccg cccgcctgct ggcgccgggc ggaccaccct    3180
ggccgctcgc ccagcgcccc gtccgccggg gcgtcgaggc gctcaccacc ggccactggc    3240
tggaactgga cacggacggc cgggcccggc agacccgctg gtgggaactc ccggagccgt    3300
ccctcacgct cgcgcagggc gcagccgccg tccgttcggc gctggacgac gcgatcacca    3360
gccgggtcgc cgcgggcggc accctcagcg ccgacctgtc cggcggtctg gactccacct    3420
cactgtgctt cctcgcgcac gcggccggcg ccgacctggt cacgtaccac gtgacgccga    3480
tcgacagcgc caacgcggac acgatgtggg cccaccgggc cgcggagtgc ctgcctgcgg    3540
cccggcacca cacgctgtcc gccgaccgcg ccgagaacct gttcgacgtc ggctacaccg    3600
ccgacctcgt gggcgcggcc ccggagggtc cctcgacctg ggcctccgga ctcgcccaca    3660
tccaggacct ggccaagcgg gccacggcgg agggcgccac actgcacctg accggcttcg    3720
gcggtgacga gctgttcggc cggatgcccg cctgcgcctg gtccctggcc cgggccacac    3780
cggtcggcgg gctgcggctg gtcaaccgct accggctggc caatcgctgg ccgtggcggg    3840
cgaccgtacg ctcgctcctt gaccgctcga cgttcacgca gaacctcggt cgggtcgccg    3900
cccgcatcga cgccccgccc ccgcccgtcg acgagcccga cttcggctgg gtgttcgcac    3960
cccgcatgcc ggcctgggcg accccgacg ccgtggccgc ggtccgcgcc cttctcaccg     4020
acgccgccac cgagggaccc gggccgctgg acgccgaccg ggcccggcac caggcgctcg    4080
cctcgctcgt cttcgagggg accaccgtcc gccaggtcaa caccgccctc ggggacaccg    4140
gcatcacctg gacgcgcgcc ttcctcgacg accgggtggt ggaggcggcc ctggccaccc    4200
ggatcgacca gcgcctgctc ggcgggcggt tcaagccgct gctcacctcg gccgcacggg    4260
gtctcgtccc cgcggacatc ctgggccgcc gtgacaaggg cgagttcagc gcggaggcgt    4320
tccggggcct ggcccgcaac cgggcccgga tcctggagct gtgcgaggac tcccagctcg    4380
cccggctcgg cctcatcgac ccggcggcct tccggtccgc ggtgctgaac ccggggccga    4440
```

```
tgtcccacca tctccagccg atcgacacca cggtggcgtg cgagagctgg ctgcggacgc    4500
atccggagac gtaccccatg ccacccgccc ggaacacgcc tacgggagaa caccgatgaa    4560
gctgaccctc gcccgcgacg tcaccctcac cgtcgtcgac tccggggccg tgctgctcga    4620
cgggcgccgc ggccgctact ggcaactgaa ccactccggc gcgggcgtcc tgcgccaact    4680
gctcgacgga acggcgcccg acgcggccgc cgccggcctc tgcgccgcgg ccccggtcag    4740
cgacgaccag gcacggcagg acgtccaggc cctcatcgac gcgctcagcg cggccaagct    4800
cgtggaggtg gcctcgtgac cacccccgcc gtggccgaac aggccccgcg gctgccctgg    4860
taccggcagc tcgcccccog gtgcgccgcg ggggcggccc gtctgctggt ccggttgccg    4920
ccggcccgac tgcaccgcgt gctgggcgtg gtcagcaagg ggtcccgccc cgccggatac    4980
gccgaggtgg cgcgggcccg ccggtccgtc gtctcggtca gcacccgctg cgcgggactc    5040
ggttgcctcc agcgttccgt ggccaccgtc ctgctgtgcc gggcacacgg caggtgggcc    5100
gactggtgca cggattcag aaccgaaccg ttcggcgcgc acgcctgggt ggaggccgag    5160
gggcggccgg tggacgagcc cggcgaactc agcgtgttcc gcacggtcct ggcggtccgc    5220
cgcccggacg gacgccggag cacctccgac cgtcccctcc gccccctccg agggagccgc    5280
tcatgacagc gatccgggcc gagggcctct acgcgtacta cggcaccgca ccggccgtga    5340
acgggctcga cctgaccgtg cccacgggca gcgtctacgg cttcctcgga ccgaacggcg    5400
cgggcaagac caccaccatc aacatgctga ccaccctgct gcggcccacc gcgggccgtg    5460
cggaggtggc cggcttcgac gtcgccgccc ggcccgccga ggtccgccgc cgtatcggca    5520
tcgtgttcca ggagtcgacc ctcgacctgg acctcaccgc cgcccagaac ctccgcttcc    5580
aggccgacct gtgcggcctg tcccgccgcg cgtcccgcga cgcgatcgcc tcgatgctcg    5640
acctgatgga cctctccgag cgccgcaggg tgcccgtacg gcagttctcc accggactgc    5700
gccgccgcct cgagatcgcc cgtggcctgc tcgccgagcc cagcgtgctg ttcctcgacg    5760
agccgacgac cggactggac gcccagaccc gcgccgccgt ctgggagcac ctggaacggc    5820
tgcgccggga gagggcatc acggtcttcg tcaccaccca tcaactggac gaggccgagc    5880
actgcgaccg gatcgcgatc atcgaccggg gcaaggtggt cacggagggc acaccagcgg    5940
acctcaaatc cgtcatcggg gccgacctcg tcgtcctgcg caccgacgac gaccagcgcg    6000
ccgccgccgt cctcggcgac cggttcggcc tcccggcgga gcccactccg gacggtctgc    6060
tgctccgggt cgagcgcgcg gcggccttgg tgccccgcct gtgcaccgaa ctcggcgtga    6120
ccgtacgcga ggtcgccatc gccccgccca ccctcgacga cgtcttcctg caccacaccg    6180
gtctcgccat ccgggagagc ccgaccggcc gcgcacgct cggcaacctc ggggaaggac    6240
tgcgatgagc cggaccgaca ccgcacccgc cgcactcggc gacgtcagcg ccgcaccctc    6300
accgaccgac cggtcccgca acgcggcgcg cccgtcctg ctgctctggc ggcgggagat    6360
gacccggctg cggcacaacc ccgtgcgcct ggccatggga ctcgtgacac cgctgctgtt    6420
cctcgtcgtc ctcggcaccg gcctcgacgc ggcgtcgtcc agcctcggca aggcccaact    6480
gaacgactac cgggccctact tgttccccgg cacgctggtc atgtccgtgc aggcgccggc    6540
gatcgcggtg ggcatctcgc tggtgtggga ccgcaggctg ggggtgctgc gccagatgct    6600
cgtggcgccg ttccccgcgcg cgtccatcgt gttcggactg gccttcggcg cgccaccac    6660 cggcgcggtc tacggcctca tggtgctgtc cgtcggcggg atcgcgagca tccgctacac    6720
gccgatgctc ctggtcgtcc tcctcgaact cctgctggtc tccctcatgt tcaccgcgct    6780
cgggctgctc gccgccgtca ccatccggca ggtcgacacc ttccaggtcg tggtgaacct    6840
```

```
gagcctgatg ccgctgatgt tcttctccgg cgcgatgttc ccgcccaacg gcctgcccgg    6900
ctggctcgac accgtcgtca agctcaaccc gctgacgtac ggcgtcgacg cggtccgccg    6960
gaccctgcca ggaccgagcg tgctcacctc ggagcagacc cggctgatgc tcggcgactg    7020
gcacccgccc gtggccgccg aactgggtgt cctggccgcc ctcaccgcgg tcgcgctggg    7080
cctcgccggc taccggttct cccgtacgtc atgagccggg gaggacaggg gacggtggac    7140
gcgagcacca cggatgtgac cacgacggcc gccgtccggg ccacgaccgg cactgggcg    7200 ggcgcggcgc ggctcgtggc ccggctgctc ctggcggcga tcctggccta cgccggtctg    7260
gtgaagatcg ggaccctcac ggaggccggg cggacggtcg cgctctaccg catcgtgccc    7320
gccgactcgg cccaactcgt gggcggcgtc ctgccgttcg tcgaggtggc gctcgcgctg    7380
ctgctcgcgg ccgggctggc caccaggcg gcagcggcgg gcgcggccgt actgctggtc    7440
gcctatgcgg cggccatcgc ctcggtgtgg gcacggggca tgtccatcga ctgcggctgt    7500
ttcggcggcg gaggcacgct cagcggtggc gccgcacgcg gctacgcgct cgacctcgcg    7560
cgcgatctgc tgctgctcgg cgcggccgcc ctcctgatcc ggaatccgcg cacccgatac    7620
gcgctggacg gctgggtcct ggacccgaag gagtgagggg catgacgagc acacagacaa    7680
cggacgccac ggtgcgggag atggtgcacc gacggcaccg gcgacggcgc acagtggtgg    7740
tgtctctggt ggccgccctg gtggtggtcg ccgccgcgct ggtgggcgcg gcctggtcc    7800 gggcgaacaa cacggcgccc ggcaaggcac cgagccgcgt accggccggg ctcgccgccg    7860
acaagtcggg cgtggccgcc tccaccggcg ccgtacgcgt cgacgtgtac ctcgactacc    7920
tctgccccga atgccgtcgt accgaacggg cactgaccac cgccctggac agtctgaggg    7980
cgcacggcgg ggtgagcgtc gtctaccacc cggtcgcctt cctcgacagc cgcagcgcac    8040
ccgcgggcta ctcgacccag gcggcctccg cggcggcctg cgcggcggac gcggggaggt    8100
tcgagcagta ctccacggtc ctgttctcga aacagcccgc cgaacagggc cctgggctca    8160
gcgaggccca gctgatcgcg gcgggccggg acgcgggcat caccgcggcg tccttcgccc    8220
gctgcgtcga ggacgccccc tacctgccct gggtacggta cgtctccgat ctcgccgcct    8280
cccgcaaggt ggcgctgacc ccgaccgtca tggtggcggg ccgccgtgtc gacgtcaccg    8340
gctccgatcc gggcggcgcg ctgacccggg cggtcacggc ggcccggcgg tgacccggct    8400
gaccgtggcc ctgtccgggg actgcatggc gacacgggga gcggtgatct cctccgaccc    8460
ggccgccgga cggctccacg aactcctcca cggcgccgac ttcgccgtca ccaacctgga    8520
ggtggtgccc agcgacggac gcggacaccc ggtgcacaac acggccggtg gcggctgtct    8580
gatcgcggac tccggtgtcc tggacgagat cacgtcggcc gggttcaccg tgctgggctg    8640
cgccaacaac cacgccatgg acctgggcac ggagggcgtg ctcggcaccg tggacctgct    8700
gcggtcgagg cggatcccgt tcgccgggat cggcgccgac ctcaccacgg cgcgccggcc    8760
cgtctacgtc gaccggccgg gcggcagcct ggcgctgctc gcctgcaccg cgacgtt      8817
```

<210> SEQ ID NO 39
<211> LENGTH: 129
<212> TYPE: DNA
<213> ORGANISM: Streptomyces sp. strain SKH-2344
<220> FEATURE:
<223> OTHER INFORMATION: SEQ ID 39; siaA-I full sequence   Example 4b-c

<400> SEQUENCE: 39

```
atgtccgcga tctacgagcc ccccatgctc caggaagtcg cgacttcga ggagctcacg     60 aagtgcctcg gcgtcggaag ctgcaacgac ttcgccggct gcggctacgc gatcgtctgc    120
```

<210> SEQ ID NO 40
<211> LENGTH: 1842
<212> TYPE: DNA
<213> ORGANISM: Streptomyces sp. strain SKH-2344
<220> FEATURE:
<223> OTHER INFORMATION: SEQ ID 40; siaB-I full sequence   Example 4b-c

<400> SEQUENCE: 40

| | |
|---|---|
| atggaattcg tggttcttcc ggactgcccg gccggtgccg cggccgtcgg ccggctgcgg | 60 |
| gcgacgcggc gcgtcgacca cgcgtcgggg cggccctgga tcgtcggcga ctggcccgag | 120 |
| gccgaggccg tcgtcgtcga ggcgggccca cggcggatgg tcgtactggg acacacccgg | 180 |
| ctcgacgaga ccgccgcggc ggccgcgctc ggccggctgc gctcgctgca cgacgtggac | 240 |
| tcgatcgcgt cccggctgcc gggagccgtc cacctggcgg tgtcactgga cggcaggacc | 300 |
| agggtgcagg gttcggccgt cggcgtacga cagatcttca ccgccgtcgt cgacggggtg | 360 |
| accgtcgccg cgagcggggt ggaaccgctg ctgcggctga ccggcgccgg cctcgacgag | 420 |
| accgtgctcg ccgcccgcct gctggcgccg gcggaccac cctggccgct cgcccagcgc | 480 |
| cccgtccgcc ggggcgtcga ggcgctcacc accggccact ggctggaact ggacacggac | 540 |
| ggccgggccc ggcagacccg ctggtgggaa ctcccgagc cgtccctcac gctcgcgcag | 600 |
| ggcgcagccg ccgtccgttc ggcgctggac gacgcgatca ccagccgggt cgccgcgggc | 660 |
| ggcacccctca gcgccgacct gtccggcggt ctggactcca cctcactgtg cttcctcgcg | 720 |
| cacgcggccg gcgccgacct ggtcacgtac cacgtgacgc cgatcgacag cgccaacgcg | 780 |
| gacacgatgt gggcccaccg ggccgcggag tgcctgcctg cggcccggca ccacacgctg | 840 |
| tccgccgacc gcgccgagaa cctgttcgac gtcggctaca ccgccgacct cgtgggcgcg | 900 |
| gccccggagg gtccctcgac ctgggcctcc ggactcgccc acatccagga cctggccaag | 960 |
| cgggccacgg cggagggcgc cacactgcac ctgaccggct cggcggtga cgagctgttc | 1020 |
| ggccggatgc ccgcctgcgc ctggtccctg gccgggccca ccggtcgg cgggctgcgg | 1080 |
| ctggtcaacc gctaccggct ggccaatcgc tggccgtggc gggcgaccgt acgtcgctc | 1140 |
| cttgaccgct cgacgttcac gcagaacctc ggtcgggtcg ccgccgcat cgacgccccg | 1200 |
| cccccgcccc tcgacgagcc cgacttcggc tgggtgttcg caccccgcat gcggcctgg | 1260 |
| gcgaccccg acgccgtggc gcggtccgc gccttctca ccgacgccgc caccgaggga | 1320 |
| cccgggccg tggacgccga ccgggcccgg caccaggcgc tcgcctcgct cgtcttcgag | 1380 |
| gggaccaccg tccgccaggt caacaccgcc ctcggggaca ccggcatcac ctgggacgcg | 1440 |
| cccttcctcg acgaccgggt ggtggaggcg ccctgccca ccggatcga ccagcgcctg | 1500 |
| ctcggcgggc ggttcaagcc gctgctcacc tcggccgcac ggggtctcgt cccgcggac | 1560 |
| atcctgggcc gccgtgacaa gggcgagttc agcgcggagg cgttccgggg cctgcccgc | 1620 |
| aaccgggccc ggatcctgga gctgtgcgag gactcccagc tcgcccggct cggcctcatc | 1680 |
| gacccggcgg ccttccggtc cgcggtgctg aacccgggc cgatgtccca ccatctccag | 1740 |
| ccgatcgaca ccacggtggc gtgcgagagc tggctgcgga cgcatccgga gacgtaccc | 1800 |
| atgccacccg ccggaacac gcctacggga gaacaccgat ga | 1842 |

<210> SEQ ID NO 41
<211> LENGTH: 264
<212> TYPE: DNA
<213> ORGANISM: Streptomyces sp. strain SKH-2344
<220> FEATURE:

<223> OTHER INFORMATION: SEQ ID 41; siaC-I full sequence   Example 4b-c

<400> SEQUENCE: 41

| | | | | | |
|---|---|---|---|---|---|
| atgaagctga | ccctcgcccg | cgacgtcacc | ctcaccgtcg | tcgactccgg | ggccgtgctg | 60 |
| ctcgacgggc | gccgcggccg | ctactggcaa | ctgaaccact | ccggcgcggg | cgtcctgcgc | 120 |
| caactgctcg | acggaacggc | gcccgacgcg | gccgccgccg | gcctctgcgc | cgcggccccg | 180 |
| gtcagcgacg | accaggcacg | gcaggacgtc | caggccctca | tcgacgcgct | cagcgcggcc | 240 |
| aagctcgtgg | aggtggcctc | gtga | | | | 264 |

<210> SEQ ID NO 42
<211> LENGTH: 471
<212> TYPE: DNA
<213> ORGANISM: Streptomyces sp. strain SKH-2344
<220> FEATURE:
<223> OTHER INFORMATION: SEQ ID 42; siaD-I full sequence   Example 4b-c

<400> SEQUENCE: 42

| | | | | | |
|---|---|---|---|---|---|
| gtgaccaccc | ccgccgtggc | cgaacaggcc | ccgcggctgc | cctggtaccg | gcagctcgcc | 60 |
| ccccggtgcg | ccgcggggc | ggcccgtctg | ctggtccggt | tgccgccggc | ccgactgcac | 120 |
| cgcgtgctgg | gcgtggtcag | caaggggtcc | cgccccgccg | gatacgccga | ggtggcgcgg | 180 |
| gcccgccggt | ccgtcgtctc | ggtcagcacc | cgctgcgcgg | gactcggttg | cctccagcgt | 240 |
| tccgtggcca | ccgtcctgct | gtgccgggca | cacggcaggt | gggccgactg | gtgcacggga | 300 |
| ttcagaaccg | aaccgttcgg | cgcgcacgcc | tgggtggagg | ccgaggggcg | gccggtggac | 360 |
| gagcccggcg | aactcagcgt | gttccgcacg | gtcctggcgg | tccgccgccc | ggacggacgc | 420 |
| cggagcacct | ccgaccgtcc | cctccgcccc | tcccgaggga | gccgctcatg | a | 471 |

<210> SEQ ID NO 43
<211> LENGTH: 966
<212> TYPE: DNA
<213> ORGANISM: Streptomyces sp. strain SKH-2344
<220> FEATURE:
<223> OTHER INFORMATION: SEQ ID 43; siaE-I full sequence   Example 4b-c

<400> SEQUENCE: 43

| | | | | | |
|---|---|---|---|---|---|
| atgacagcga | tccgggccga | gggcctctac | gcgtactacg | gcaccgcacc | ggccgtgaac | 60 |
| gggctcgacc | tgaccgtgcc | cacgggcagc | gtctacggct | tcctcggacc | gaacggcgcg | 120 |
| ggcaagacca | ccaccatcaa | catgctgacc | accctgctgc | ggcccaccgc | gggccgtgcg | 180 |
| gaggtggccg | gcttcgacgt | cgccgcccgg | cccgccgagg | tccgccgccg | tatcggcatc | 240 |
| gtgttccagg | agtcgaccct | cgacctggac | ctcaccgccg | cccagaacct | ccgcttccag | 300 |
| gccgacctgt | gcggcctgtc | ccgccgcgcg | tcccgcgacg | cgatcgcctc | gatgctcgac | 360 |
| ctgatggacc | tctccgagcg | ccgcagggtg | cccgtacggc | agttctccac | cggactgcgc | 420 |
| cgccgcctcg | agatcgcccg | tggcctgctc | gccgagccca | gcgtgctgtt | cctcgacgag | 480 |
| ccgacgaccg | gactggacgc | ccagacccgc | gccgccgtct | gggagcacct | ggaacggctg | 540 |
| cgccggggaga | ggggcatcac | ggtcttcgtc | accaccatc | aactggacga | ggccgagcac | 600 |
| tgcgaccgga | tcgcgatcat | cgaccggggc | aaggtggtca | cggagggcac | accagcggac | 660 |
| ctcaaatccg | tcatcggggc | cgacctcgtc | gtcctgcgca | ccgacgacga | ccagcgcgcc | 720 |
| gccgccgtcc | tcggcgaccg | gttcggcctc | ccggcggagc | ccactccgga | cggtctgctg | 780 |
| ctccgggtcg | agcgcgcggc | ggccttggtg | ccccgcctgt | gcaccgaact | cggcgtgacc | 840 |
| gtacgcgagg | tcgccatcgc | cccgcccacc | ctcgacgacg | tcttcctgca | ccacaccggt | 900 |

```
ctcgccatcc gggagagccc gaccggcccg cgcacgctcg gcaacctcgg ggaaggactg    960
cgatga                                                               966
```

<210> SEQ ID NO 44
<211> LENGTH: 870
<212> TYPE: DNA
<213> ORGANISM: Streptomyces sp. strain SKH-2344
<220> FEATURE:
<223> OTHER INFORMATION: SEQ ID 44; siaF-I full sequence  Example 4b-c

<400> SEQUENCE: 44

```
atgagccgga ccgacaccgc acccgccgca ctcggcgacg tcagcgccgc accctcaccg     60
accgaccggt cccgcaacgc ggcgcgcccc gtcctgctgc tctggcggcg ggagatgacc    120
cggctgcggc acaacccccgt gcgcctggcc atgggactcg tgacaccgct gctgttcctc   180
gtcgtcctcg gcaccggcct cgacgcggcg tcgtccagcc tcggcaaggc ccaactgaac    240
gactaccggg cctacttgtt ccccggcacg ctggtcatgt ccgtgcaggc gccggcgatc    300
gcggtgggca tctcgctggt gtgggaccgc aggctggggg tgctgcgcca gatgctcgtg    360
gcgccgttcc cgcgcgcgtc catcgtgttc ggactggcct tcggcggcgc caccaccggc    420
gcggtctacg gcctcatggt gctgtccgtc ggcgggatcg cgagcatccg ctacacgccg    480
atgctgctgg tcgtcctcct cgaactcctg ctggtctccc tcatgttcac cgcgctcggg    540
ctgctcgccg ccgtcaccat ccggcaggtc gacaccttcc aggtcgtggt gaacctgagc    600
ctgatgccgc tgatgttctt ctccggcgcg atgttcccgc caacggcct gcccggctgg     660 ctcgacaccg tcgtcaagct caacccgctg acgtacggcg tcgacgcggt ccgccggacc    720
ctgccaggac cgagcgtgct cacctcggag cagaccccggc tgatgctcgg cgactggcac   780
ccgcccgtgg ccgccgaact gggtgtcctg gccgccctca ccgcggtcgc gctgggcctc    840
gccggctacc ggttctcccg tacgtcatga                                     870
```

<210> SEQ ID NO 45
<211> LENGTH: 546
<212> TYPE: DNA
<213> ORGANISM: Streptomyces sp. strain SKH-2344
<220> FEATURE:
<223> OTHER INFORMATION: SEQ ID 45; siaG-1 full sequence  Example 4b-c

<400> SEQUENCE: 45

```
atgagccggg gaggacaggg gacggtggac gcgagcacca cggatgtgac cacgacggcc     60
gccgtccggg ccacgaccgg gcactgggcg ggcgcgcgc ggctcgtggc ccggctgctc     120
ctggcggcga tcctggccta cgccggtctg gtgaagatcg ggacctcac ggaggccggg     180 cggacggtcg cgctctaccg catcgtgccc gccgactcgg cccaactcgt gggcggcgtc    240
ctgccgttcg tcgaggtggc gctcgcgctg ctgctcgcgg ccgggctggc caccagggcg    300
gcagcggcgg gcgcggccgt actgctggtc gcctatgcgg cggccatcgc ctcggtgtgg    360
gcacggggca tgtccatcga ctgcggctgt ttcgcggcg gaggcacgct cagcggtggc    420
gccgcacgcg gctacgcgct cgacctcgcg cgcgatctgc tgctgctcgg cgcggccgcc    480
ctcctgatcc ggaatccgcg caccgatac gcgctggacg gctgggtcct ggacccgaag    540
gagtga                                                               546
```

<210> SEQ ID NO 46
<211> LENGTH: 732
<212> TYPE: DNA
<213> ORGANISM: Streptomyces sp. strain SKH-2344
<220> FEATURE:

<223> OTHER INFORMATION: SEQ ID 46; siaH-I full sequence  Example 4b-c

<400> SEQUENCE: 46

| | | | | | |
|---|---|---|---|---|---|
| atgacgagca | cacagacaac | ggacgccacg | gtgcgggaga | tggtgcaccg | acggcaccgg | 60 |
| cgacggcgca | cagtggtggt | gtctctggtg | gccgccctgg | tggtggtcgc | cgccgcgctg | 120 |
| gtgggcgcgg | gcctggtccg | ggcgaacaac | acggcgcccg | gcaaggcacc | gagccgcgta | 180 |
| ccggccgggc | tcgccgccga | caagtcgggc | gtggccgcct | ccaccggcgc | cgtacgcgtc | 240 |
| gacgtgtacc | tcgactacct | ctgccccgaa | tgccgtcgta | ccgaacgggc | actgaccacc | 300 |
| gccctggaca | gtctgagggc | gcacggcggg | gtgagcgtcg | tctaccaccc | ggtcgccttc | 360 |
| ctcgacagcc | gcagcgcacc | cgcgggctac | tcgacccagg | cggcctccgc | ggcggcctgc | 420 |
| gcggcggacg | cggggaggtt | cgagcagtac | tccacggtcc | tgttctcgaa | acagcccgcc | 480 |
| gaacagggcc | ctgggctcag | cgaggcccag | ctgatcgcgg | cgggccggga | cgcgggcatc | 540 |
| accgcggcgt | ccttcgcccg | ctgcgtcgag | gacgcccct | acctgccctg | gtacgcgtac | 600 |
| gtctccgatc | tcgccgcctc | ccgcaaggtg | gcgctgaccc | cgaccgtcat | ggtggcgggc | 660 |
| cgccgtgtcg | acgtcaccgg | ctccgatccg | ggcggcgcgc | tgacccgggc | ggtcacggcg | 720 |
| gcccggcggt | ga | | | | | 732 |

<210> SEQ ID NO 47
<211> LENGTH: 5875
<212> TYPE: DNA
<213> ORGANISM: Artificial Sequence
<220> FEATURE:
<223> OTHER INFORMATION: SEQ ID 47; synthetic sia-I locus full sequence
      Example 5b

<400> SEQUENCE: 47

| | | | | | |
|---|---|---|---|---|---|
| tctagaaata | attttgttta | actttaagaa | ggagatatac | atatgtccgc | tatctatgag | 60 |
| ccacctatgc | tgcaggaagt | tggcgacttt | gaagaactga | ccaaatgcct | gggcgtcggc | 120 |
| agttgtaacg | actttgcagg | ctgcgggtac | gcgattgtgt | gcttctggtg | aagctttaag | 180 |
| aaggagatat | accatggaat | tcgtagtgct | cccagactgt | cctgcgggcg | ccgccgcggt | 240 |
| agggcgtctg | cgtgccactc | gtcgcgtcga | ccatgccagc | ggacgcccct | tggattgtagg | 300 |
| tgattggccg | gaggccgagg | ccgtagtcgt | ggaagccgga | ccgcgccgca | tggtggtttt | 360 |
| gggtcacaca | cgcctggatg | aaacggccgc | agcggcggcc | ctcggtcgtc | tgcgtagcct | 420 |
| gcatgatgtg | gatagcattg | cgtcgcgttt | gccaggggca | gtacacctgg | ccgtgtctct | 480 |
| cgatggccgt | accgtgtac | agggctcggc | agttggtgtg | cggcagattt | tcacagccgt | 540 |
| agtagacggc | gtgaccgtcg | cggcctctgg | cgtcgaacct | ctgctgcgtc | tgacgggcgc | 600 |
| cggtctcgac | gaaacagttc | tggcggcacg | ccttctcgca | ccgggtggcc | ctccctggcc | 660 |
| gctggcgcag | cgtccggtcc | gccgcggtgt | ggaagcgctc | acaactggtc | attggttaga | 720 |
| actggacacc | gacgggcgcg | ctcgccagac | acgttggtgg | gaattaccag | agccgtctct | 780 |
| gacccctcgcc | caaggcgcag | cggccgtccg | cagtgcctta | gatgacgcga | ttaccagccg | 840 |
| tgtggctgca | ggtggcaccc | tctcggccga | tctgagcggg | ggcttggata | gcacctcgtt | 900 |
| gtgctttctt | gcgcatgcgg | cggggcgga | cttagttacc | tatcatgtta | cgccaattga | 960 |
| tagcgcgaat | gcagatacta | tgtgggctca | ccgcgcggca | gagtgcttac | cggcagcgcg | 1020 |
| tcaccatacc | ctgagcgccc | atcgcgccga | aaacttgttt | gatgtgggct | acactgccga | 1080 |
| cctggtgggc | gcagccccgg | agggccctag | cacctgggcg | agcggactgg | ctcacattca | 1140 |
| agacctggcg | aaacgcgcaa | ccgcggaagg | tgccaccctg | catctgaccg | gctttggcgg | 1200 |

```
tgacgagctt tttggccgta tgccggcgtg cgcgtggtct ctggcacgtg caacccagt   1260 cggaggtctc cgcctggtca atcgctaccg cttggcgaat cggtggccgt ggcgtgcaac   1320
ggtccgctcg ctgctggacc gcagcacctt tacccaaaat ttgggccgtg tcgcagcgcg   1380
tattgatgca cctccacctc cagttgacga accagatttc ggttgggtct ttgcgccgcg   1440
catgccggcc tgggcgactc cggatgcagt ggcggccgtt cgtgccctgc tgacagatgc   1500
ggcgactgag ggtccaggtc cgttagacgc agatcgtgcg cggcaccaag cgctggcgtc   1560
cctggtcttt gagggcacga ctgtgcgcca ggtcaacacg cgttaggcg acactggcat    1620 tacttgggac gcaccgttct tagatgaccg cgtggtggag gccgcgctgg cgacgcgtat   1680
tgatcagcgc ctgttgggcg gtcgctttaa accgttgctg acgtccgcgg cgcgcggcct   1740
ggtacccgcc gacattctgg ggcgtcgtga taaaggggaa tttagcgcgg aagcatttcg   1800
tggtctcgcg cgtaaccgtg cccgtatcct cgaactttgc gaagattcgc aacttgcccg   1860
cttgggcttg attgaccctg ctgccttccg cagtgctgtt cttaaccctg gtccgatgtc   1920
tcaccatctg caaccgattg acaccactgt agcttgcgaa tcctggctgc ggacccatcc   1980
ggaaacttac ccgatgcctc cggcccgcaa cacgcctacg ggagaacacc gatgaagtta   2040
accttagccc gtgatgtgac cttaacggtg gtagattccg gggcagtctt gctggacggc   2100
cgtcgtgggc gttattggca actgaaccat agtggggcgg cgttcttcg ccagctgctg     2160 gatggcaccg ctccagacgc cgcggcagcg gggttgtgcg ccgccgctcc ggtgtccgat   2220
gatcaggccc gtcaggacgt ccaggccctg attgatgccc tgtcagctgc aaagctcgtg   2280
gaggtggcct catgacaacg ccggctgttg ccgaacaggc accccgtttg ccttggtacc   2340
gccagcttgc accgcgctgc gcggctggtg cggcgcgctt actcgttcgt ttgccgccgg   2400
cgcgtctgca tcgtgtgctc ggggtggtga gcaaaggtag ccgtccggcg ggatacgctg   2460
aagtcgctcg cgcacggcgc tccgttgttt cggtttcgac acgctgcgcg ggtctgggct   2520
gtctgcagcg ctccgtggcg acggttctgt tatgtcgcgc tcatgggcgt tgggcagatt   2580
ggtgtacagg gttccgcaca gaaccgttcg gcgcccacgc ctgggtcgag gcggagggcc   2640
ggccggtgga tgaaccaggt gaactgtcag ttttccgtac cgtccttgca gtacgtcgtc   2700
cggatggacg tcgcagcacg agtgaccgcc ctctccgtcc ttcccgaggg agccgctcat   2760
gaccgctatt cgcgccgaag gcctgtatgc atattatggc accgccctg cggttaatgg     2820 actggacctt acagtgccca cgggtagcgt gtatggattc ctcggcccga atggcgcggg   2880
gaaaacgacc accattaaca tgttaacgac tcttctgcgc ccgacggcgg tcgtgcgga     2940 agttgcagga ttcgacgtag ctgcccgtcc tgcggaagtg cgccgtcgca ttggtattgt   3000
tttccaggaa agtacattag atctggacct gactgccgct cagaacctgc gctttcaagc   3060
tgatctttgc gggctgtccc gtcgcgccag ccgcgatgcg atcgcgagta tgttggacct   3120
gatggatctc tcggagcgtc gtcgcgtgcc ggttcgccag tttagtacgg gcctgcgtcg   3180
ccgcttggaa attgctcgcg gccttctggc ggagccttca gttctgtttc tggatgaacc   3240
cacaacgggt ttagatgcac agacccgggc tgccgtctgg gaacatctgg aacgcttgcg   3300
ccgtgagcgt ggtattacgg ttttcgtgac gactcaccag ctggacgagg ccgagcattg   3360
cgatcgcatc gcaatcatcg atcgcggtaa agtcgtgacg gagggtaccc cggcggacct   3420
gaaatccgtt attggggcgg atctggtggt attacggacg gatgacgatc agcgtgcagc   3480
agccgtgctt ggcgatcgct tcggtctccc ggcggaaccc acgccagacg ggctgctgct   3540
gcgtgtcgag cgtgccgcgg cactggtccc tcgcctgtgc actgaactgg gggtaacagt   3600
```

```
tcgcgaggtg gccattgcgc cgcctactct ggatgatgta ttttttgcatc acacaggctt    3660 ggccatccgc gagtccccca ctgggccgcg cacactgggc aacctcgggg aaggactgcg    3720
atgagccgca cagacactgc tcccgcagcg ctggggatg tttctgccgc gccatcgcca    3780
acagaccgct cccgtaacgc agctcgtccg gtgctgttac tgtggcgccg tgaaatgacc    3840
cgtttacgtc ataatcctgt acgcttagct atgggtctgg tgacgccgct cctgttcctt    3900
gttgtgctcg gcactggact ggatgccgca agctccagtt taggcaaagc gcagctgaac    3960
gattatcgcg cgtatctgtt cccgggaaca ctggtaatgt cagtgcaggc accagcgatt    4020
gcagttggca ttagcctggt atgggatcgc cgtctgggtg ttctgcgtca gatgctggtt    4080
gcgccgttcc cacgcgccag cattgtcttt ggtctggcgt tcggtggggc gaccaccgga    4140
gctgtttatg gtctgatggt gcttagcgtc ggaggcatcg cgtctatccg ctataccca    4200 atgttactcg tcgttttact tgagctgctg ctggtatcac tgatgtttac cgcgctggga    4260
ctcctcgcgg cggtgaccat ccgccaagtc gacaccttcc aggtggttgt caacctgtcg    4320
ctgatgccgc tgatgttctt tagcggagct atgtttccgc gaatggatt gccaggttgg    4380 cttgatacag tggtgaaact gaacccgctt acgtacggtg tcgatgcggt acgccgcact    4440
cttcctggtc ctagtgttct gacgtctgaa cagacacgtc tcatgctggg tgactggcat    4500
ccgcctgtcg cggcggaact cggtgtcctg gcggcgttga ccgcagtggc gttgggcctc    4560
gcaggctacc ggttctcccg tacgtcatga ccgtggcgg tcagggcaca gtcgacgcaa    4620
gtaccacgga cgtgacgaca acagcggccg tacgcgcgac caccgggcat gggcggtg    4680 cggcccgtct tgtcgcccgt ctgctgctgg ccgcaattct ggcgtacgca gggttagtta    4740
aaatcggtga tctgacggag gccggccgta ccgtcgccct gtaccgcatc gtcccggccg    4800
acagtgccca gctggtgggt ggtgtgctgc cgttcgtcga ggtagccctt gcgcttcttt    4860
tagccgctgg tctggccacc cgcgctgccg cggccggagc ggcggtcctt cttgtggcgt    4920
acgctgcagc gattgcttcg gtttgggccc gtgggatgag cattgactgc ggttgcttcg    4980
gaggtggcgg tacactgagc gggggagcag cgcgcggtta tgcgctggat ctggctcgcg    5040
atctgttatt gctgggtgca gccgccctgt tgattcgtaa tcctcgcacc cgttatgcct    5100
tggatggttg ggtcctggac ccgaaggagt gagggggcatg acgagtacgc aaaccacaga    5160
tgcaactgtg cgtgagatgg ttcatcgtcg gcaccgccgt cgtcgtacgg tagttgtgag    5220
cttagttgcg gccttggttg tcgttgcggc agccctggtc ggcgcaggcc tggtgcgcgc    5280
caacaacacg gccccgggga aggctccgtc acgcgtcccg gcaggccttg cagcggataa    5340
gtccggtgtg gctgcgagta ccggtgccgt gcgcgttgac gtgtaccttg attacctgtg    5400
tcccgagtgt cgtcgtacgg aacgtgcgtt gaccactgcg ctggactctc ttcgcgctca    5460
cggcggtgtt tctgtagtgt accatcctgt tgcgtttctc gatagtcgca gtgcacctgc    5520
aggttactca acccaggcag cctccgcggc cgcgtgtgca gcagatgccg gtcgtttcga    5580
acagtacagc accgtcctct tctctaaaca acctgctgaa caaggtccgg gactgagtga    5640
agcccaactc atcgccgcgg gccgcgatgc tgggattacc gctgcatcct tcgcacgttg    5700
tgtcgaagat gccccgtacc ttccgtgggt acgttacgta tcagatctcg cagcatcccg    5760
gaaagtagct ctgaccccga ccgtgatggt ggccggtcgc cgtgttgatg ttaccggttc    5820
ggacccgggt ggcgcgctca cccgcgcagt cactgcagca cgtcgctgac tcgag         5875
```

<210> SEQ ID NO 48
<211> LENGTH: 129

```
<212> TYPE: DNA
<213> ORGANISM: Artificial Sequence
<220> FEATURE:
<223> OTHER INFORMATION: SEQ ID 48; synthetic siaA-I full sequence
      Example 5b

<400> SEQUENCE: 48
atgtccgcta tctatgagcc acctatgctg caggaagttg gcgactttga agaactgacc     60
aaatgcctgg gcgtcggcag ttgtaacgac tttgcaggct gcgggtacgc gattgtgtgc    120
ttctggtga                                                            129

<210> SEQ ID NO 49
<211> LENGTH: 1842
<212> TYPE: DNA
<213> ORGANISM: Artificial Sequence
<220> FEATURE:
<223> OTHER INFORMATION: SEQ ID 49; synthetic siaB-I full sequence
      Example 5b

<400> SEQUENCE: 49
atggaattcg tagtgctccc agactgtcct gcgggcgccg ccgcggtagg gcgtctgcgt     60
gccactcgtc gcgtcgacca tgccagcgga cgcccttgga ttgtaggtga ttggccggag    120
gccgaggccg tagtcgtgga agccggaccg cgccgcatgg tggttttggg tcacacacgc    180
ctggatgaaa cggccgcagc ggcggccctc ggtcgtctgc gtagcctgca tgatgtggat    240
agcattgcgt cgcgtttgcc aggggcagta cacctggccg tgtctctcga tggccgtacc    300
cgtgtacagg gctcggcagt tggtgtgcgg cagattttca cagccgtagt agacggcgtg    360
accgtcgcgg cctctggcgt cgaacctctg ctgcgtctga cgggcgccgg tctcgacgaa    420
acagttctgg cggcacgcct tctcgcaccg ggtggccctc cctggccgct ggcgcagcgt    480
ccggtccgcc gcggtgtgga agcgctcaca actggtcatt ggttagaact ggacaccgac    540
gggcgcgctc gccagacacg ttggtgggaa ttaccagagc cgtctctgac cctcgcccaa    600
ggcgcagcgg ccgtccgcag tgccttagat gacgcgatta ccagccgtgt ggctgcaggt    660
ggcaccctct cggccgatct gagcggggc ttggatagca cctcgttgtg ctttcttgcg    720
catgcggcgg gggcggactt agttacctat catgttacgc caattgatag cgcgaatgca    780
gatactatgt gggctcaccg cgcggcagag tgcttaccgg cagcgcgtca ccataccctg    840
agcgccgatc gcgccgaaaa cttgtttgat gtgggctaca ctgccgacct ggtgggcgca    900
gccccggagg gccctagcac ctgggcgagc ggactggctc acattcaaga cctggcgaaa    960
cgcgcaaccg cggaaggtgc caccctgcat ctgaccggct ttggcggtga cgagcttttt   1020
ggccgtatgc cggcgtgcgc gtggtctctg gcacgtgcaa ccccagtcgg aggtctccgc   1080
ctggtcaatc gctaccgctt ggcgaatcgg tggccgtggc gtgcaacggt ccgctcgctg   1140
ctggaccgca gcaccttttac ccaaaatttg ggccgtgtcg cagcgcgtat tgatgcacct   1200
ccacctccag ttgacgaacc agatttcggt tgggtctttg cgccgcgcat gccggcctgg   1260
gcgactccgg atgcagtggc ggccgttcgt gccctgctga cagatgcggc gactgagggt   1320
ccaggtccgt tagacgcaga tcgtgcgcgg caccaagcgc tggcgtccct ggtctttgag   1380
ggcacgactg tgcgccaggt caacacggcg ttaggcgaca ctggcattac ttgggacgca   1440
ccgttcttag atgaccgcgt ggtggaggcc gcgctggcga cgcgtattga tcagcgcctg   1500
ttgggcggtc gctttaaacc gttgctgacg tccgcggcgc gcggcctggt acccgccgac   1560
attctggggc gtcgtgataa aggggaattt agcgcggaag catttcgtgg tctcgcgcgt   1620
aaccgtgccc gtatcctcga actttgcgaa gattcgcaac ttgcccgctt gggcttgatt   1680
```

-continued

| | |
|---|---|
| gaccctgctg ccttccgcag tgctgttctt aaccctggtc cgatgtctca ccatctgcaa | 1740 |
| ccgattgaca ccactgtagc ttgcgaatcc tggctgcgga cccatccgga aacttacccg | 1800 |
| atgcctccgg cccgcaacac gcctacggga gaacaccgat ga | 1842 |

<210> SEQ ID NO 50
<211> LENGTH: 264
<212> TYPE: DNA
<213> ORGANISM: Artificial Sequence
<220> FEATURE:
<223> OTHER INFORMATION: SEQ ID 50; synthetic siaC-I full sequence Example 5b

<400> SEQUENCE: 50

| | |
|---|---|
| atgaagttaa ccttagcccg tgatgtgacc ttaacggtgg tagattccgg ggcagtcttg | 60 |
| ctggacggcc gtcgtgggcg ttattggcaa ctgaaccata gtggggcggg cgttcttcgc | 120 |
| cagctgctgg atggcaccgc tccagacgcc gcggcagcgg ggttgtgcgc cgccgctccg | 180 |
| gtgtccgatg atcaggcccg tcaggacgtc caggccctga ttgatgccct gtcagctgca | 240 |
| aagctcgtgg aggtggcctc atga | 264 |

<210> SEQ ID NO 51
<211> LENGTH: 471
<212> TYPE: DNA
<213> ORGANISM: Artificial Sequence
<220> FEATURE:
<223> OTHER INFORMATION: SEQ ID 51; synthetic siaD-I full sequence Example 5b

<400> SEQUENCE: 51

| | |
|---|---|
| atgacaacgc cggctgttgc cgaacaggca ccccgtttgc cttggtaccg ccagcttgca | 60 |
| ccgcgctgcg cggctggtgc ggcgcgctta ctcgttcgtt tgccgccggc cgtctgcat | 120 |
| cgtgtgctcg gggtggtgag caaaggtagc cgtccggcgg gatacgctga agtcgctcgc | 180 |
| gcacggcgct ccgttgtttc ggtttcgaca cgctgcgcgg gtctgggctg tctgcagcgc | 240 |
| tccgtggcga cggttctgtt atgtcgcgct catgggcgtt gggcagattg gtgtacaggg | 300 |
| ttccgcacag aaccgttcgg cgcccacgcc tgggtcgagg cggagggccg gccggtggat | 360 |
| gaaccaggtg aactgtcagt tttccgtacc gtccttgcag tacgtcgtcc ggatggacgt | 420 |
| cgcagcacga gtgaccgccc tctccgtcct tcccgaggga gccgctcatg a | 471 |

<210> SEQ ID NO 52
<211> LENGTH: 966
<212> TYPE: DNA
<213> ORGANISM: Artificial Sequence
<220> FEATURE:
<223> OTHER INFORMATION: SEQ ID 52; synthetic siaE-1 full sequence Example 5b

<400> SEQUENCE: 52

| | |
|---|---|
| atgaccgcta ttcgcgccga aggcctgtat gcatattatg gcaccgcccc tgcggttaat | 60 |
| ggactggacc ttacagtgcc cacgggtagc gtgtatggat tcctcggccc gaatggcgcg | 120 |
| gggaaaacga ccaccattaa catgttaacg actcttctgc gcccgacggc gggtcgtgcg | 180 |
| gaagttgcag gattcgacgt agctgcccgt cctgcggaag tgcgccgtcg cattggtatt | 240 |
| gttttccagg aaagtacatt agatctggac ctgactgccg ctcagaacct gcgctttcaa | 300 |
| gctgatcttt gcgggctgtc ccgtcgcgcc agccgcgatg cgatcgcgag tatgttggac | 360 |
| ctgatggatc tctcggagcg tcgtcgcgtg ccggttcgcc agtttagtac gggcctgcgt | 420 |

```
cgccgcttgg aaattgctcg cggccttctg gcggagcctt cagttctgtt tctggatgaa    480
cccacaacgg gtttagatgc acagacccgg gctgccgtct gggaacatct ggaacgcttg    540
cgccgtgagc gtggtattac ggttttcgtg acgactcacc agctggacga ggccgagcat    600
tgcgatcgca tcgcaatcat cgatcgcggt aaagtcgtga cggagggtac cccggcggac    660
ctgaaatccg ttattggggc ggatctggtg gtattacgga cggatgacga tcagcgtgca    720
gcagccgtgc ttggcgatcg cttcggtctc ccggcgaaac ccacgccaga cgggctgctg    780
ctgcgtgtcg agcgtgccgc ggcactggtc cctcgcctgt gcactgaact gggggtaaca    840
gttcgcgagg tggccattgc gccgcctact ctggatgatg tattttttgca tcacacaggc    900 ttggccatcc gcgagtcccc cactgggccg cgcacactgg gcaacctcgg ggaaggactg    960
cgatga                                                                966

<210> SEQ ID NO 53
<211> LENGTH: 870
<212> TYPE: DNA
<213> ORGANISM: Artificial Sequence
<220> FEATURE:
<223> OTHER INFORMATION: SEQ ID 53; synthetic siaF-1 full sequence
      Example 5b

<400> SEQUENCE: 53
atgagccgca cagacactgc tcccgcagcg ctggggggatg tttctgccgc gccatcgcca     60
acagaccgct cccgtaacgc agctcgtccg gtgctgttac tgtggcgccg tgaaatgacc    120
cgtttacgtc ataatcctgt acgcttagct atgggtctgg tgacgccgct cctgttcctt    180
gttgtgctcg gcactggact ggatgccgca agctccagtt taggcaaagc gcagctgaac    240
gattatcgcg cgtatctgtt cccgggaaca ctggtaatgt cagtgcaggc accagcgatt    300
gcagttggca ttagcctggt atgggatcgc cgtctgggtg ttctgcgtca gatgctggtt    360
gcgccgttcc cacgcgccag cattgtcttt ggtctggcgt tcggtggggc gaccaccgga    420
gctgtttatg gtctgatggt gcttagcgtc ggaggcatcg cgtctatccg ctataccccca    480 atgttactcg tcgttttact tgagctgctg ctggtatcac tgatgtttac cgcgctggga    540
ctcctcgcgg cggtgaccat ccgccaagtc gacaccttcc aggtggttgt caacctgtcg    600
ctgatgccgc tgatgttctt tagcggagct atgtttccgc cgaatggatt gccaggttgg    660
cttgatacag tggtgaaact gaacccgctt acgtacggtg tcgatgcggt acgccgcact    720
cttcctggtc ctagtgttct gacgtctgaa cagacacgtc tcatgctggg tgactggcat    780
ccgcctgtcg cggcggaact cggtgtcctg gcggcgttga ccgcagtggc gttgggcctc    840
gcaggctacc ggttctcccg tacgtcatga                                      870

<210> SEQ ID NO 54
<211> LENGTH: 546
<212> TYPE: DNA
<213> ORGANISM: Artificial Sequence
<220> FEATURE:
<223> OTHER INFORMATION: SEQ ID 54; synthetic siaG-I full sequence
      Example 5b

<400> SEQUENCE: 54
atgagccgtg cggtcaggg cacagtcgac gcaagtacca cggacgtgac gacaacagcg      60
gccgtacgcg cgaccaccgg gcattgggcg ggtgcggccc gtcttgtcgc ccgtctgctg    120
ctggccgcaa ttctggcgta cgcagggtta gttaaaatcg gtgatctgac ggaggccggc    180
cgtaccgtcg ccctgtaccg catcgtcccg gccgacagtg cccagctggt gggtggtgtg    240
```

```
ctgccgttcg tcgaggtagc ccttgcgctt cttttagccg ctggtctggc cacccgcgct      300
gccgcggccg gagcggcggt ccttcttgtg gcgtacgctg cagcgattgc ttcggtttgg      360
gcccgtggga tgagcattga ctgcggttgc ttcggaggtg gcggtacact gagcggggga      420
gcagcgcgcg gttatgcgct ggatctggct cgcgatctgt tattgctggg tgcagccgcc      480
ctgttgattc gtaatcctcg cacccgttat gccttggatg gttgggtcct ggacccgaag      540
gagtga                                                                546

<210> SEQ ID NO 55
<211> LENGTH: 732
<212> TYPE: DNA
<213> ORGANISM: Artificial Sequence
<220> FEATURE:
<223> OTHER INFORMATION: SEQ ID 55; synthetic siaH-I full sequence
      Example 5b

<400> SEQUENCE: 55
atgacgagta cgcaaaccac agatgcaact gtgcgtgaga tggttcatcg tcggcaccgc       60
cgtcgtcgta cggtagttgt gagcttagtt gcggccttgg ttgtcgttgc ggcagccctg      120
gtcggcgcag gcctggtgcg cgccaacaac acggccccgg ggaaggctcc gtcacgcgtc      180
ccggcaggcc ttgcagcgga taagtccggt gtggctgcga gtaccggtgc cgtgcgcgtt      240
gacgtgtacc ttgattacct gtgtcccgag tgtcgtcgta cggaacgtgc gttgaccact      300
gcgctggact ctcttcgcgc tcacggcggt gtttctgtag tgtaccatcc tgttgcgttt      360
ctcgatagtc gcagtgcacc tgcaggttac tcaacccagg cagcctccgc ggccgcgtgt      420
gcagcagatg ccggtcgttt cgaacagtac agcaccgtcc tcttctctaa caacctgct       480 gaacaaggtc cgggactgag tgaagcccaa ctcatcgccg cgggccgcga tgctgggatt      540
accgctgcat ccttcgcacg ttgtgtcgaa gatgccccgt accttccgtg gtacgttac      600 gtatcagatc tcgcagcatc ccggaaagta gctctgaccc cgaccgtgat ggtggccggt      660
cgccgtgttg atgttaccgg ttcggacccg ggtggcgcgc tcacccgcgc agtcactgca      720
gcacgtcgct ga                                                         732

<210> SEQ ID NO 56
<211> LENGTH: 5875
<212> TYPE: DNA
<213> ORGANISM: Artificial Sequence
<220> FEATURE:
<223> OTHER INFORMATION: SEQ ID 56; synthetic sia-II locus full sequence
      Example 5b

<400> SEQUENCE: 56
tctagaaata attttgttta actttaagaa ggagatatac atatgtccgc tatctatgag       60
ccacctatgc tgcaggaagt tggcgacttt gaagaactga ccaaatgcct gggcatcggc      120
agttgtaacg actttgcagg ctgcgggtac gcgattgtgt gcttctggtg aagctttaag      180
aaggagatat accatggaat tcgtagtgct cccagactgt cctgcgggcg ccgccgcggt      240
agggcgtctg cgtgccactc gtcgcgtcga ccatgccagc ggacgccctt ggattgtagg      300
tgattggccg gaggccgagg ccgtagtcgt ggaagccgga ccgcgccgca tggtggtttt      360
gggtcacaca cgcctggatg aaacggccgc agcggcggcc tcggtcgtc tgcgtagcct      420 gcatgatgtg gatagcattg cgtcgcgttt gccagggggca gtacacctgg ccgtgtctct      480
cgatggccgt acccgtgtac agggctcggc agttggtgtg cggcagattt tcacagccgt      540
agtagacggc gtgaccgtcg cggcctctgg cgtcgaacct ctgctgcgtc tgacgggcgc      600
```

```
cggtctcgac gaaacagttc tggcggcacg ccttctcgca ccgggtggcc ctccctggcc    660
gctggcgcag cgtccggtcc gccgcggtgt ggaagcgctc acaactggtc attggttaga    720
actggacacc gacgggcgcg ctcgccagac acgttggtgg gaattaccag agccgtctct    780
gaccctcgcc caaggcgcag cggccgtccg cagtgcctta gatgacgcga ttaccagccg    840
tgtggctgca ggtggcaccc tctcggccga tctgagcggg gcttggata gcacctcgtt     900
gtgctttctt gcgcatgcgg cggggcgga cttagttacc tatcatgtta cgccaattga     960
tagcgcgaat gcagatacta tgtgggctca ccgcgcggca gagtgcttac cggcagcgcg   1020
tcaccatacc ctgagcgccg atcgcgccga aaacttgttt gatgtgggct acactgccga   1080
cctggtgggc gcagccccgg agggccctag cacctgggcg agcggactgg ctcacattca   1140
agacctggcg aaacgcgcaa ccgcggaagg tgccaccctg catctgaccg gctttggcgg   1200
tgacgagctt tttggccgta tgccggcgtg cgcgtggtct ctggcacgtg caaccccagt   1260
cggaggtctc cgcctggtca atcgctaccg cttggcgaat cggtgccgt ggcgtgcaac    1320
ggtccgctcg ctgctggacc gcagcacctt tacccaaaat ttgggccgtg tcgcagcgcg   1380
tattgatgca cctccacctc cagttgacga accagatttc ggttgggtct ttgcgccgcg   1440
catgccggcc tgggcgactc cggatgcagt ggcggccgtt cgtgccctgc tgacagatgc   1500
ggcgactgag ggtccaggtc cgttagacgc agatcgtgcg cggcaccaag cgctggcgtc   1560
cctggtcttt gagggcacga ctgtgcgcca ggtcaacacg gcgttaggcg acactggcat   1620
tacttgggac gcaccgttct tagatgaccg cgtggtggag gccgcgctgg cgacgcgtat   1680
tgatcagcgc ctgttgggcg gtcgctttaa accgttgctg acgtccgcgg cgcgcggcct   1740
ggtacccgcc gacattctgg ggcgtcgtga taaaggggaa tttagcgcgg aagcatttcg   1800
tggtctcgcg cgtaaccgtg cccgtatcct cgaactttgc gaagattcgc aacttgcccg   1860
cttgggcttg attgaccctg ctgccttccg cagtgctgtt cttaaccctg gtccgatgtc   1920
tcaccatctg caaccgattg acaccactgt agcttgcgaa tcctggctgc ggacccatcc   1980
ggaaacttac ccgatgcctc cggcccgcaa cacgcctacg ggagaacacc gatgaagtta   2040
accttagccc gtgatgtgac cttaacggtg gtagattccg gggcagtctt gctggacggc   2100
cgtcgtgggc gttattggca actgaaccat agtggggcgg gcgttcttcg ccagctgctg   2160
gatggcaccc tccagacgc gcggcagcg gggttgtgcg ccgccgctcc ggtgtccgat    2220
gatcaggccc gtcaggacgt ccaggccctg attgatgccc tgtcagctgc aaagctcgtg   2280
gaggtggcct catgacaacg ccggctgttg ccgaacaggc accccgtttg ccttggtacc   2340
gccagcttgc accgcgctgc gcggctggtg cggcgcgctt actcgttcgt ttgccgccgg   2400
cgcgtctgca tcgtgtgctc ggggtggtga gcaaaggtag ccgtccggcg ggatacgctg   2460
aagtcgctcg cgcacggcgc tccgttgttt cggtttcgac acgctgcgcg ggtctgggct   2520
gtctgcagcg ctccgtggcg acggttctgt tatgtcgcgc tcatgggcgt tgggcagatt   2580
ggtgtacagg gttccgcaca gaaccgttcg gcgcccacgc ctgggtcgag gcggagggcc   2640
ggccggtgga tgaaccaggt gaactgtcag ttttccgtac cgtccttgca gtacgtcgtc   2700
cggatggacg tcgcagcacg agtgaccgcc ctctccgtcc ttcccgaggg agccgctcat   2760
gaccgctatt cgcgccgaag gcctgtatgc atattatggc accgcccctg cggttaatgg   2820
actggacctt acagtgccca cgggtagcgt gtatggattc ctcggcccga atggcgcggg   2880
gaaaacgacc accattaaca tgttaacgac tcttctgcgc ccgacggcgg gtcgtgcgga   2940
agttgcagga ttcgacgtag ctgcccgtcc tgcggaagtg cgccgtcgca ttggtattgt   3000
```

```
tttccaggaa agtacattag atctggacct gactgccgct cagaacctgc gctttcaagc    3060
tgatctttgc gggctgtccc gtcgcgccag ccgcgatgcg atcgcgagta tgttggacct    3120
gatggatctc tcggagcgtc gtcgcgtgcc ggttcgccag tttagtacgg gcctgcgtcg    3180
ccgcttggaa attgctcgcg gccttctggc ggagccttca gttctgtttc tggatgaacc    3240
cacaacgggt ttagatgcac agacccgggc tgccgtctgg aacatctgg aacgcttgcg     3300
ccgtgagcgt ggtattacgg ttttcgtgac gactcaccag ctggacgagg ccgagcattg    3360
cgatcgcatc gcaatcatcg atcgcggtaa agtcgtgacg gagggtaccc cggcggacct    3420
gaaatccgtt attggggcgg atctggtggt attacggacg gatgacgatc agcgtgcagc    3480
agccgtgctt ggcgatcgct tcggtctccc ggcggaaccc acgccagacg ggctgctgct    3540
gcgtgtcgag cgtgccgcgg cactggtccc tcgcctgtgc actgaactgg gggtaacagt    3600
tcgcgaggtg gccattgcgc cgcctactct ggatgatgta tttttgcatc acacaggctt    3660
ggccatccgc gagtccccca ctgggccgcg cacactgggc aacctcgggg aaggactgcg    3720
atgagccgca cagacactgc tcccgcagcg ctggggatg tttctgccgc gccatcgcca     3780
acagaccgct cccgtaacgc agctcgtccg gtgctgttac tgtggcgccg tgaaatgacc    3840
cgtttacgtc ataatcctgt acgcttagct atgggtctgg tgacgccgct cctgttcctt    3900
gttgtgctcg gcactggact ggatgccgca agctccagtt taggcaaagc gcagctgaac    3960
gattatcgcg cgtatctgtt cccgggaaca ctggtaatgt cagtgcaggc accagcgatt    4020
gcagttggca ttagcctggt atgggatcgc cgtctgggtg ttctgcgtca gatgctggtt    4080
gcgccgttcc cacgcgccag cattgtcttt ggtctggcgt tcggtggggc gaccaccgga    4140
gctgtttatg gtctgatggt gcttagcgtc ggaggcatcg cgtctatccg ctataccca     4200
atgttactcg tcgttttact tgagctgctg ctggtatcac tgatgtttac cgcgctggga    4260
ctcctcgcgg cggtgaccat ccgccaagtc gacaccttcc aggtggttgt caacctgtcg    4320
ctgatgccgc tgatgttctt tagcggagct atgtttccgc cgaatggatt gccaggttgg    4380
cttgatacag tggtgaaact gaacccgctt acgtacggtg tcgatgcggt acgccgcact    4440
cttcctggtc ctagtgttct gacgtctgaa cagacacgtc tcatgctggg tgactggcat    4500
ccgcctgtcg cggcggaact cggtgtcctg gcggcgttga ccgcagtggc gttgggcctc    4560
gcaggctacc ggttctcccg tacgtcatga gccgtggcgg tcagggcaca gtcgacgcaa    4620
gtaccacgga cgtgacgaca acagcggccg tacgcgcgac caccgggcat gggcgggtg     4680
cggcccgtct tgtcgcccgt ctgctgctgg ccgcaattct ggcgtacgca gggttagtta    4740
aaatcggtga tctgacggag gccggccgta ccgtcgccct gtaccgcatc gtcccggccg    4800
acagtgccca gctggtgggt ggtgtgctgc gttcgtcga ggtagccctt gcgcttcttt     4860
tagccgctgg tctggccacc cgcgctgccg cggccggagc ggcggtcctt cttgtggcgt    4920
acgctgcagc gattgcttcg gtttgggccc gtgggatgag cattgactgc ggttgcttcg    4980
gaggtggcgg tacactgagc gggggagcag cgcgcggtta tgcgctggat ctggctcgcg    5040
atctgttatt gctgggtgca gccgccctgt tgattcgtaa tcctcgcacc cgttatgcct    5100
tggatggttg ggtcctggac ccgaaggagt gaggggcatg acgagtacgc aaaccacaga    5160
tgcaactgtg cgtgagatgg ttcatcgtcg gcaccgccgt cgtcgtacgg tagttgtgag    5220
cttagttgcg gccttggttg tcgttgcggc agccctggtc ggcgcaggcc tggtgcgcgc    5280
caacaacacg gccccgggga aggctccgtc acgcgtcccg gcaggccttg cagcggataa    5340
gtccggtgtg gctgcgagta ccggtgccgt gcgcgttgac gtgtaccttg attacctgtg    5400
```

```
tcccgagtgt cgtcgtacgg aacgtgcgtt gaccactgcg ctggactctc ttcgcgctca   5460
cggcggtgtt tctgtagtgt accatcctgt tgcgtttctc gatagtcgca gtgcacctgc   5520
aggttactca acccaggcag cctccgcggc cgcgtgtgca gcagatgccg gtcgtttcga   5580
acagtacagc accgtcctct tctctaaaca acctgctgaa caaggtccgg gactgagtga   5640
agcccaactc atcgccgcgg gccgcgatgc tgggattacc gctgcatcct tcgcacgttg   5700
tgtcgaagat gccccgtacc ttccgtgggt acgttacgta tcagatctcg cagcatcccg   5760
gaaagtagct ctgaccccga ccgtgatggt ggccggtcgc cgtgttgatg ttaccggttc   5820
ggacccgggt ggcgcgctca cccgcgcagt cactgcagca cgtcgctgac tcgag        5875
```

<210> SEQ ID NO 57
<211> LENGTH: 129
<212> TYPE: DNA
<213> ORGANISM: Artificial Sequence
<220> FEATURE:
<223> OTHER INFORMATION: SEQ ID 57; synthetic siaA-II full sequence
      Example 5b

<400> SEQUENCE: 57

```
atgtccgcta tctatgagcc acctatgctg caggaagttg gcgactttga agaactgacc    60
aaatgcctgg gcatcggcag ttgtaacgac tttgcaggct gcgggtacgc gattgtgtgc   120
ttctggtga                                                           129
```

<210> SEQ ID NO 58
<211> LENGTH: 5875
<212> TYPE: DNA
<213> ORGANISM: Artificial Sequence
<220> FEATURE:
<223> OTHER INFORMATION: SEQ ID 58; synthetic sia-III locus full
      sequence   Example 5b

<400> SEQUENCE: 58

```
tctagaaata attttgttta actttaagaa ggagatatac atatgtccgc tatctatgag     60
ccacctatgc tgcaggaagt tggcgacttt gaagaactga ccaaatgcct gggcatcggc    120
agttgtaacg actttgcagg ctgcgggtac gcggttgtgt gcttctggtg aagctttaag   180
aaggagatat accatggaat tcgtagtgct cccagactgt cctgcgggcg ccgccgcggt   240
agggcgtctg cgtgccactc gtcgcgtcga ccatgccagc ggacgccctt ggattgtagg   300
tgattggccg gaggccgagg ccgtagtcgt ggaagccgga ccgcgccgca tggtggtttt   360
gggtcacaca cgcctggatg aaacggccgc agcggcggcc ctcggtcgtc tgcgtagcct   420
gcatgatgtg gatagcattg cgtcgcgttt gccaggggca gtacacctgg ccgtgtctct   480
cgatggccgt acccgtgtac agggctcggc agttggtgtg cggcagattt tcacagccgt   540
agtagacggc gtgaccgtcg cggcctctgg cgtcgaacct ctgctgcgtc tgacgggcgc   600
cggtctcgac gaaacagttc tggcggcacg ccttctcgca ccgggtggcc ctccctggcc   660
gctggcgcag cgtccggtcc gccgcggtgt ggaagcgctc acaactggtc attggttaga   720
actggacacc gacgggcgcg ctcgccagac acgttggtgg gaattaccag agccgtctct   780
gaccctcgcc caaggcgcag cggccgtccg cagtgcctta gatgacgcga ttaccagccg   840
tgtggctgca ggtggcaccc tctcggccga tctgagcggg gcttggata gcacctcgtt   900 gtgcttctt gcgcatgcgg cggggcgga cttagttacc tatcatgtta cgccaattga   960
tagcgcgaat gcagatacta tgtgggctca ccgcgcggca gagtgcttac cggcagcgcg   1020
tcaccatacc ctgagcgccg atcgcgccga aaacttgttt gatgtgggct acactgccga  1080
```

```
cctggtgggc gcagcccgg agggccctag cacctgggcg agcggactgg ctcacattca    1140
agacctggcg aaacgcgcaa ccgcggaagg tgccaccctg catctgaccg gctttggcgg    1200
tgacgagctt tttggccgta tgccggcgtg cgcgtggtct ctggcacgtg caaccccagt    1260
cggaggtctc cgcctggtca atcgctaccg cttggcgaat cggtggccgt ggcgtgcaac    1320
ggtccgctcg ctgctggacc gcagcacctt tacccaaaat ttgggccgtg tcgcagcgcg    1380
tattgatgca cctccacctc cagttgacga accagatttc ggttgggtct ttgcgccgcg    1440
catgccggcc tgggcgactc cggatgcagt ggcggccgtt cgtgccctgc tgacagatgc    1500
ggcgactgag ggtccaggtc cgttagacgc agatcgtgcg cggcaccaag cgctggcgtc    1560
cctggtcttt gagggcacga ctgtgcgcca ggtcaacacg gcgttaggcg cactggcat    1620 tacttgggac gcaccgttct tagatgaccg cgtggtggag gccgcgctgg cgacgcgtat    1680
tgatcagcgc ctgttgggcg gtcgctttaa accgttgctg acgtccgcgg cgcgcggcct    1740
ggtacccgcc gacattctgg ggcgtcgtga taaaggggaa tttagcgcgg aagcatttcg    1800
tggtctcgcg cgtaaccgtg cccgtatcct cgaactttgc gaagattcgc aacttgcccg    1860
cttgggcttg attgaccctg ctgccttccg cagtgctgtt cttaaccctg gtccgatgtc    1920
tcaccatctg caaccgattg acaccactgt agcttgcgaa tcctggctgc ggacccatcc    1980
ggaaacttac ccgatgcctc cggcccgcaa cacgcctacg ggagaacacc gatgaagtta    2040
accttagccc gtgatgtgac cttaacggtg gtagattccg gggcagtctt gctggacggc    2100
cgtcgtgggc gttattggca actgaaccat agtggggcgg cgttcttcg ccagctgctg    2160 gatggcaccg ctccagacgc cgcggcagcg gggttgtgcg ccgccgctcc ggtgtccgat    2220
gatcaggccc gtcaggacgt ccaggccctg attgatgccc tgtcagctgc aaagctcgtg    2280
gaggtggcct catgacaacg ccggctgttg ccgaacaggc accccgtttg ccttggtacc    2340
gccagcttgc accgcgctgc gcggctggtg cggcgcgctt actcgttcgt ttgccgccgg    2400
cgcgtctgca tcgtgtgctc ggggtggtga gcaaaggtag ccgtccggcg ggatacgctg    2460
aagtcgctcg cgcacggcgc tccgttgttt cggtttcgac acgctgcgcg ggtctgggct    2520
gtctgcagcg ctccgtggcg acggttctgt tatgtcgcgc tcatgggcgt tgggcagatt    2580
ggtgtacagg gttccgcaca gaaccgttcg gcgcccacgc ctgggtcgag gcggagggcc    2640
ggccggtgga tgaaccaggt gaactgtcag ttttccgtac cgtccttgca gtacgtcgtc    2700
cggatggacg tcgcagcacg agtgaccgcc ctctccgtcc ttcccgaggg agccgctcat    2760
gaccgctatt cgcgccgaag gcctgtatgc atattatggc accgcccctg cggttaatgg    2820
actggacctt acagtgccca cgggtagcgt gtatggattc ctcggcccga atggcgcggg    2880
gaaaacgacc accattaaca tgttaacgac tcttctgcgc ccgacggcgg tcgtgcgga    2940 agttgcagga ttcgacgtag ctgcccgtcc tgcggaagtg cgccgtcgca ttggtattgt    3000
tttccaggaa agtacattag atctggacct gactgccgct cagaacctgc gctttcaagc    3060
tgatctttgc gggctgtccc gtcgcgccag ccgcgatgcg atcgcgagta tgttggacct    3120
gatggatctc tcggagcgtc gtcgcgtgcc ggttcgccag tttagtacgg gcctgcgtcg    3180
ccgcttggaa attgctcgcg gccttctggc ggagccttca gttctgtttc tggatgaacc    3240
cacaacgggt ttagatgcac agacccgggc tgccgtctgg aacatctgg aacgcttgcg    3300 ccgtgagcgt ggtattacgg ttttcgtgac gactcaccag ctggacgagg ccgagcattg    3360
cgatcgcatc gcaatcatcg atcgcggtaa agtcgtgacg gagggtaccc cggcggacct    3420
gaaatccgtt attggggcgg atctggtggt attacggacg gatgacgatc agcgtgcagc    3480
```

```
agccgtgctt ggcgatcgct tcggtctccc ggcggaaccc acgccagacg ggctgctgct   3540
gcgtgtcgag cgtgccgcgg cactggtccc tcgcctgtgc actgaactgg gggtaacagt   3600
tcgcgaggtg gccattgcgc cgcctactct ggatgatgta tttttgcatc acacaggctt   3660
ggccatccgc gagtccccca ctgggccgcg cacactgggc aacctcgggg aaggactgcg   3720
atgagccgca cagacactgc tcccgcagcg ctgggggatg tttctgccgc gccatcgcca   3780
acagaccgct cccgtaacgc agctcgtccg gtgctgttac tgtggcgccg tgaaatgacc   3840
cgtttacgtc ataatcctgt acgcttagct atgggtctgg tgacgccgct cctgttcctt   3900
gttgtgctcg gcactggact ggatgccgca agctccagtt taggcaaagc gcagctgaac   3960
gattatcgcg cgtatctgtt cccgggaaca ctggtaatgt cagtgcaggc accagcgatt   4020
gcagttggca ttagcctggt atgggatcgc cgtctgggtg ttctgcgtca gatgctggtt   4080
gcgccgttcc cacgcgccag cattgtcttt ggtctggcgt tcggtggggc gaccaccgga   4140
gctgtttatg gtctgatggt gcttagcgtc ggaggcatcg cgtctatccg ctataccccca   4200
atgttactcg tcgtttttact tgagctgctg ctggtatcac tgatgtttac cgcgctggga   4260
ctcctcgcgg cggtgaccat ccgccaagtc gacaccttcc aggtggttgt caacctgtcg   4320
ctgatgccgc tgatgttctt tagcggagct atgtttccgc gaatggatt gccaggttgg   4380
cttgatacag tggtgaaact gaacccgctt acgtacggtg tcgatgcggt acgccgcact   4440
cttcctggtc ctagtgttct gacgtctgaa cagacacgtc tcatgctggg tgactggcat   4500
ccgcctgtcg cggcggaact cggtgtcctg gcggcgttga ccgcagtggc gttgggcctc   4560
gcaggctacc ggttctcccg tacgtcatga gccgtggcgg tcagggcaca gtcgacgcaa   4620
gtaccacgga cgtgacgaca acagcggccg tacgcgcgac caccgggcat gggcgggtg   4680
cggcccgtct tgtcgcccgt ctgctgctgg ccgcaattct ggcgtacgca gggttagtta   4740
aaatcggtga tctgacggag gccggccgta ccgtcgccct gtaccgcatc gtcccggccg   4800
acagtgccca gctggtgggt ggtgtgctgc cgttcgtcga ggtagcccctt gcgcttcttt   4860
tagccgctgg tctggccacc cgcgctgccg cggccggagc ggcggtcctt cttgtggcgt   4920
acgctgcagc gattgcttcg gtttgggccc gtgggatgag cattgactgc ggttgcttcg   4980
gaggtggcgg tacactgagc gggggagcag cgcgcggtta tgcgctggat ctggctcgcg   5040
atctgttatt gctgggtgca gccgcccgt tgattcgtaa tcctcgcacc cgttatgcct   5100
tggatggttg ggtcctggac ccgaaggagt gaggggcatg acgagtacgc aaaccacaga   5160
tgcaactgtg cgtgagatgg ttcatcgtcg gcaccgccgt cgtcgtacgg tagttgtgag   5220
cttagttgcg gccttggttg tcgttgcggc agccctggtc ggcgcaggcc tggtgcgcgc   5280
caacaacacg gccccgggga aggctccgtc acgcgtcccg gcaggccttg cagcggataa   5340
gtccggtgtg gctgcgagta ccggtgccgt gcgcgttgac gtgtaccttg attacctgtg   5400
tcccgagtgt cgtcgtacgg aacgtgcgtt gaccactgcg ctggactctc ttcgcgctca   5460
cggcggtgtt tctgtagtgt accatcctgt tgcgtttctc gatagtcgca gtgcacctgc   5520
aggttactca acccaggcag cctccgcggc cgcgtgtgca gcagatgccg gtcgtttcga   5580
acagtacagc accgtcctct tctctaaaca acctgctgaa caaggtccgg gactgagtga   5640
agcccaactc atcgccgcgg gccgcgatgc tgggattacc gctgcatcct tcgcacgttg   5700
tgtcgaagat gccccgtacc ttccgtgggt acgttacgta tcagatctcg cagcatcccg   5760
gaaagtagct ctgaccccga ccgtgatggt ggccggtcgc cgtgttgatg ttaccggttc   5820
ggacccgggt ggcgcgctca cccgcgcagt cactgcagca cgtcgctgac tcgag        5875
```

<210> SEQ ID NO 59
<211> LENGTH: 129
<212> TYPE: DNA
<213> ORGANISM: Artificial Sequence
<220> FEATURE:
<223> OTHER INFORMATION: SEQ ID 59; synthetic siaA-III full sequence
      Example 5b

<400> SEQUENCE: 59

| | | |
|---|---|---|
| atgtccgcta tctatgagcc acctatgctg caggaagttg gcgactttga agaactgacc | 60 | |
| aaatgcctgg gcatcggcag ttgtaacgac tttgcaggct gcgggtacgc ggttgtgtgc | 120 | |
| ttctggtga | 129 | |

<210> SEQ ID NO 60
<211> LENGTH: 5875
<212> TYPE: DNA
<213> ORGANISM: Artificial Sequence
<220> FEATURE:
<223> OTHER INFORMATION: SEQ ID 60; synthetic sia-IV locus full
      sequence  Example 5b

<400> SEQUENCE: 60

| | |
|---|---|
| tctagaaata attttgttta actttaagaa ggagatatac atatgtccgc tatctatgag | 60 |
| ccacctatgc tgcaggaagt tggcgacttt gaagaactga ccaaatgcct gggcgtcggc | 120 |
| agttgtaacg actttgcagg ctgcgggtac gcggttgtgt gcttctggtg aagctttaag | 180 |
| aaggagatat accatggaat tcgtagtgct cccagactgt cctgcgggcg ccgccgcggt | 240 |
| agggcgtctg cgtgccactc gtcgcgtcga ccatgccagc ggacgccctt ggattgtagg | 300 |
| tgattggccg gaggccgagg ccgtagtcgt ggaagccgga ccgcgccgca tggtggtttt | 360 |
| gggtcacaca cgcctggatg aaacggccgc agcggcggcc ctcggtcgtc tgcgtagcct | 420 |
| gcatgatgtg gatagcattg cgtcgcgttt gccaggggca gtacacctgg ccgtgtctct | 480 |
| cgatggccgt acccgtgtac agggctcggc agttggtgtg cggcagattt tcacagccgt | 540 |
| agtagacggc gtgaccgtcg cggcctctgg cgtcgaacct ctgctgcgtc tgacgggcgc | 600 |
| cggtctcgac gaaacagttc tggcggcacg ccttctcgca ccgggtggcc ctccctggcc | 660 |
| gctggcgcag cgtccggtcc gccgcggtgt ggaagcgctc acaactggtc attggttaga | 720 |
| actggacacc gacgggcgcg ctcgccagac acgttggtgg gaattaccag agccgtctct | 780 |
| gacccctcgc caaggcgcag cggccgtccg cagtgccttg atgacgcga ttaccagccg | 840 |
| tgtggctgca ggtggcaccc tctcggccga tctgagcggg gcttggata gcacctcgtt | 900 |
| gtgctttctt gcgcatgcgg cggggggcgga cttagttacc tatcatgtta cgccaattga | 960 |
| tagcgcgaat gcagatacta tgtgggctca ccgcgcggca gagtgcttac cggcagcgcg | 1020 |
| tcaccatacc ctgagcgccg atcgcgccga aaacttgttt gatgtgggct acactgccga | 1080 |
| cctggtgggc gcagcccgg agggccctag cacctgggcg agcggactgg ctcacattca | 1140 |
| agacctggcg aaacgcgcaa ccgcggaagg tgccaccctg catctgaccg gctttggcgg | 1200 |
| tgacgagctt tttggccgta tgccggcgtg cgcgtggtct ctggcacgtg caaccccagt | 1260 |
| cggaggtctc cgcctggtca atcgctaccg cttggcgaat cggtggccgt ggcgtgcaac | 1320 |
| ggtccgctcg ctgctggacc gcagcacctt tacccaaaat ttgggccgtg tcgcagcgcg | 1380 |
| tattgatgca cctccaccctc cagttgacga accagatttc ggttgggtct ttgcgccgcg | 1440 |
| catgccggcc tggcgactc cggatgcagt ggcggccgtt cgtgccctgc tgacagatgc | 1500 |
| ggcgactgag ggtccaggtc cgttagacgc agatcgtgcg cggcaccaag cgctggcgtc | 1560 |

```
cctggtctttt gagggcacga ctgtgcgcca ggtcaacacg gcgttaggcg acactggcat    1620
tacttgggac gcaccgttct tagatgaccg cgtggtggag gccgcgctgg cgacgcgtat    1680
tgatcagcgc ctgttgggcg gtcgctttaa accgttgctg acgtccgcgg cgcgcggcct    1740
ggtacccgcc gacattctgg ggcgtcgtga taaaggggaa tttagcgcgg aagcatttcg    1800
tggtctcgcg cgtaaccgtg cccgtatcct cgaactttgc gaagattcgc aacttgcccg    1860
cttgggcttg attgaccctg ctgccttccg cagtgctgtt cttaaccctg gtccgatgtc    1920
tcaccatctg caaccgattg acaccactgt agcttgcgaa tcctggctgc ggacccatcc    1980
ggaaacttac ccgatgcctc cggcccgcaa cacgcctacg ggagaacacc gatgaagtta    2040
accttagccc gtgatgtgac cttaacggtg gtagattccg gggcagtctt gctggacggc    2100
cgtcgtgggc gttattggca actgaaccat agtggggcgg gcgttcttcg ccagctgctg    2160
gatggcaccg ctccagacgc cgcggcagcg gggttgtgcg ccgccgctcc ggtgtccgat    2220
gatcaggccc gtcaggacgt ccaggccctg attgatgccc tgtcagctgc aaagctcgtg    2280
gaggtggcct catgacaacg ccggctgttg ccgaacaggc accccgtttg ccttggtacc    2340
gccagcttgc accgcgctgc gcggctggtg cggcgcgctt actcgttcgt ttgccgccgg    2400
cgcgtctgca tcgtgtgctc ggggtggtga gcaaaggtag ccgtccggcg ggatacgctg    2460
aagtcgctcg cgcacggcgc tccgttgttt cggtttcgac acgctgcgcg ggtctgggct    2520
gtctgcagcg ctccgtggcg acggttctgt tatgtcgcgc tcatgggcgt tgggcagatt    2580
ggtgtacagg gttccgcaca gaaccgttcg gcgcccacgc ctgggtcgag gcggagggcc    2640
ggccggtgga tgaaccaggt gaactgtcag ttttccgtac cgtccttgca gtacgtcgtc    2700
cggatggacg tcgcagcacg agtgaccgcc ctctccgtcc ttcccgaggg agccgctcat    2760
gaccgctatt cgcgccgaag gcctgtatgc atattatggc accgccctg cggttaatgg    2820 actggacctt acagtgccca cgggtagcgt gtatggattc ctcggcccga atggcgcggg    2880
gaaaacgacc accattaaca tgttaacgac tcttctgcgc ccgacggcgg gtcgtgcgga    2940
agttgcagga ttcgacgtag ctgcccgtcc tgcggaagtg cgccgtcgca ttggtattgt    3000
tttccaggaa agtacattag atctggacct gactgccgct cagaacctgc gctttcaagc    3060
tgatctttgc gggctgtccc gtcgcgccag ccgcgatgcg atcgcgagta tgttggacct    3120
gatggatctc tcggagcgtc gtcgcgtgcc ggttcgccag tttagtacgg gcctgcgtcg    3180
ccgcttggaa attgctcgcg gccttctggc ggagccttca gttctgtttc tggatgaacc    3240
cacaacgggt ttagatgcac agacccgggc tgccgtctgg aacatctgg aacgcttgcg    3300 ccgtgagcgt ggtattacgg ttttcgtgac gactcaccag ctggacgagg ccgagcattg    3360
cgatcgcatc gcaatcatcg atcgcggtaa agtcgtgacg gagggtaccc cggcggacct    3420
gaaatccgtt attggggcgg atctggtggt attacggacg gatgacgatc agcgtgcagc    3480
agccgtgctt ggcgatcgct tcggtctccc ggcggaaccc acgccagacg ggctgctgct    3540
gcgtgtcgag cgtgccgcgg cactggtccc tcgcctgtgc actgaactgg gggtaacagt    3600
tcgcgaggtg gccattgcgc cgcctactct ggatgatgta ttttttgcatc acacaggctt    3660 ggccatccgc gagtccccca ctgggccgcg cacactgggc aacctcgggg aaggactgcg    3720
atgagccgca cagacactgc tcccgcagcg ctggggatg tttctgccgc gccatcgcca    3780
acagaccgct cccgtaacgc agctcgtccg gtgctgttac tgtggcgccg tgaaatgacc    3840
cgtttacgtc ataatcctgt acgcttagct atgggtctgg tgacgccgct cctgttcctt    3900
gttgtgctcg gcactggact ggatgccgca agctccagtt taggcaaagc gcagctgaac    3960
```

-continued

```
gattatcgcg cgtatctgtt cccgggaaca ctggtaatgt cagtgcaggc accagcgatt    4020
gcagttggca ttagcctggt atgggatcgc cgtctgggtg ttctgcgtca gatgctggtt    4080
gcgccgttcc cacgcgccag cattgtcttt ggtctggcgt tcggtggggc gaccaccgga    4140
gctgtttatg gtctgatggt gcttagcgtc ggaggcatcg cgtctatccg ctatacccca    4200
atgttactcg tcgttttact tgagctgctg ctggtatcac tgatgtttac cgcgctggga    4260
ctcctcgcgg cggtgaccat ccgccaagtc gacaccttcc aggtggttgt caacctgtcg    4320
ctgatgccgc tgatgttctt tagcggagct atgtttccgc cgaatggatt gccaggttgg    4380
cttgatacag tggtgaaact gaacccgctt acgtacggtg tcgatgcggt acgccgcact    4440
cttcctggtc ctagtgttct gacgtctgaa cagacacgtc tcatgctggg tgactggcat    4500
ccgcctgtcg cggcggaact cggtgtcctg cggcgttga ccgcagtggc gttgggcctc    4560
gcaggctacc ggttctcccg tacgtcatga ccgtggcgg tcagggcaca gtcgacgcaa    4620
gtaccacgga cgtgacgaca acagcggccg tacgcgcgac caccgggcat tgggcgggtg    4680
cggcccgtct tgtcgcccgt ctgctgctgg ccgcaattct ggcgtacgca gggttagtta    4740
aaatcggtga tctgacggag gccggccgta ccgtcgccct gtaccgcatc gtcccggccg    4800
acagtgccca gctggtgggt ggtgtgctgc cgttcgtcga ggtagccctt gcgcttcttt    4860
tagccgctgg tctggccacc cgcgctgccg cggccggagc ggcggtcctt cttgtggcgt    4920
acgctgcagc gattgcttcg gtttgggccc gtgggatgag cattgactgc ggttgcttcg    4980
gaggtggcgg tacactgagc gggggagcag cgcgcggtta tgcgctggat ctggctcgcg    5040
atctgttatt gctgggtgca gccgccctgt tgattcgtaa tcctcgcacc cgttatgcct    5100
tggatggttg ggtcctggac ccgaaggagt gaggggcatg acgagtacgc aaaccacaga    5160
tgcaactgtg cgtgagatgg ttcatcgtcg gcaccgccgt cgtcgtacgg tagttgtgag    5220
cttagttgcg gccttggttg tcgttgcggc agccctggtc ggcgcaggcc tggtgcgcgc    5280
caacaacacg gccccgggga aggctccgtc acgcgtcccg gcaggccttg cagcggataa    5340
gtccggtgtg gctgcgagta ccggtgccgt gcgcgttgac gtgtaccttg attacctgtg    5400
tcccgagtgt cgtcgtacgg aacgtgcgtt gaccactgcg ctggactctc ttcgcgctca    5460
cggcggtgtt tctgtagtgt accatcctgt tgcgtttctc gatagtcgca gtgcacctgc    5520
aggttactca acccaggcag cctccgcggc cgcgtgtgca gcagatgccg gtcgtttcga    5580
acagtacagc accgtcctct tctctaaaca acctgctgaa caaggtccgg gactgagtga    5640
agcccaactc atcgccgcgg gccgcgatgc tgggattacc gctgcatcct tcgcacgttg    5700
tgtcgaagat gccccgtacc ttccgtgggt acgttacgta tcagatctcg cagcatcccg    5760
gaaagtagct ctgaccccga ccgtgatggt ggccggtcgc cgtgttgatg ttaccggttc    5820
ggacccgggt ggcgcgctca cccgcgcagt cactgcagca cgtcgctgac tcgag         5875
```

<210> SEQ ID NO 61
<211> LENGTH: 129
<212> TYPE: DNA
<213> ORGANISM: Artificial Sequence
<220> FEATURE:
<223> OTHER INFORMATION: SEQ ID 61; synthetic siaA-IV full sequence Example 5b

<400> SEQUENCE: 61

```
atgtccgcta tctatgagcc acctatgctg caggaagttg gcgactttga agaactgacc      60
aaatgcctgg gcgtcggcag ttgtaacgac tttgcaggct gcgggtacgc ggttgtgtgc     120
ttctggtga                                                              129
```

-continued

```
<210> SEQ ID NO 62
<211> LENGTH: 21
<212> TYPE: PRT
<213> ORGANISM: Escherichia coli
<220> FEATURE:
<223> OTHER INFORMATION: bacteriocidal peptide microcin J25
<220> FEATURE:
<221> NAME/KEY: MISC_FEATURE
<222> LOCATION: (13)..(13)
<223> OTHER INFORMATION: Xaa denotes any amino acid

<400> SEQUENCE: 62

Gly Gly Ala Gly His Val Pro Glu Tyr Phe Val Gly Xaa Gly Thr Pro
1               5                   10                  15

Ile Ser Phe Tyr Gly
            20

<210> SEQ ID NO 63
<211> LENGTH: 21
<212> TYPE: PRT
<213> ORGANISM: Streptomyces griseoflavus
<220> FEATURE:
<223> OTHER INFORMATION: siamcyin III linear sequence
<220> FEATURE:
<221> NAME/KEY: MISC_FEATURE
<222> LOCATION: (13)..(13)
<223> OTHER INFORMATION: Xaa denotes any amino acid

<400> SEQUENCE: 63

Cys Leu Gly Ile Gly Ser Cys Asn Asp Phe Ala Gly Cys Gly Tyr Ala
1               5                   10                  15

Val Val Cys Phe Trp
            20

<210> SEQ ID NO 64
<211> LENGTH: 9
<212> TYPE: PRT
<213> ORGANISM: Streptomyces griseoflavus
<220> FEATURE:
<223> OTHER INFORMATION: siamycin III precursor partial sequence

<400> SEQUENCE: 64

Cys Gly Tyr Ala Val Val Cys Phe Trp
1               5

<210> SEQ ID NO 65
<211> LENGTH: 9
<212> TYPE: PRT
<213> ORGANISM: Streptomyces griseoflavus
<220> FEATURE:
<223> OTHER INFORMATION: siamycin III precursor partial sequence

<400> SEQUENCE: 65

Cys Leu Gly Ile Gly Ser Cys Asn Asp
1               5

<210> SEQ ID NO 66
<211> LENGTH: 21
<212> TYPE: PRT
<213> ORGANISM: Streptomyces griseoflavus
<220> FEATURE:
<223> OTHER INFORMATION: siamycin III precursor partial sequence

<400> SEQUENCE: 66

Cys Leu Gly Ile Gly Ser Cys Asn Asp Phe Ala Gly Cys Gly Tyr Ala
1               5                   10                  15
```

```
Val Val Cys Phe Trp
            20

<210> SEQ ID NO 67
<211> LENGTH: 21
<212> TYPE: PRT
<213> ORGANISM: Streptomyces griseoflavus
<220> FEATURE:
<223> OTHER INFORMATION: siamycin III precursor partial sequence

<400> SEQUENCE: 67

Cys Leu Gly Ile Gly Ser Cys Asn Asp Phe Ala Gly Cys Gly Tyr Ala
1               5                   10                  15

Val Val Cys Phe Trp
            20

<210> SEQ ID NO 68
<211> LENGTH: 21
<212> TYPE: PRT
<213> ORGANISM: Streptomyces sp.
<220> FEATURE:
<223> OTHER INFORMATION: siamycin I precursor partial sequence

<400> SEQUENCE: 68

Cys Leu Gly Val Gly Ser Cys Asn Asp Phe Ala Gly Cys Gly Tyr Ala
1               5                   10                  15

Ile Val Cys Phe Trp
            20

<210> SEQ ID NO 69
<211> LENGTH: 21
<212> TYPE: PRT
<213> ORGANISM: Streptomyces sp.
<220> FEATURE:
<223> OTHER INFORMATION: siamycin I linear sequence

<400> SEQUENCE: 69

Cys Leu Gly Val Gly Ser Cys Asn Asp Phe Ala Gly Cys Gly Tyr Ala
1               5                   10                  15

Ile Val Cys Phe Trp
            20
```